US012590973B2

(12) United States Patent
Hernandez Ruiz et al.

(10) Patent No.: US 12,590,973 B2
(45) Date of Patent: Mar. 31, 2026

(54) USES OF IL-40 AND METHODS FOR DETECTING IL-40 ACTIVITY

(71) Applicant: BIOLEGEND, INC., San Diego, CA (US)

(72) Inventors: Marcela Hernandez Ruiz, San Diego, CA (US); Gerardo Arrevillaga Boni, San Diego, CA (US); David Michael Soper, San Diego, CA (US)

(73) Assignee: BioLegend, Inc., San Diego, CA (US)

( * ) Notice: Subject to any disclaimer, the term of this patent is extended or adjusted under 35 U.S.C. 154(b) by 1238 days.

(21) Appl. No.: 17/393,340

(22) Filed: Aug. 3, 2021

(65) Prior Publication Data

US 2022/0043004 A1 Feb. 10, 2022

Related U.S. Application Data

(63) Continuation of application No. PCT/US2020/016778, filed on Feb. 5, 2020.

(60) Provisional application No. 62/803,037, filed on Feb. 8, 2019.

(51) Int. Cl.
*G01N 33/68* (2006.01)

(52) U.S. Cl.
CPC . *G01N 33/6869* (2013.01); *G01N 2333/5428* (2013.01)

(58) Field of Classification Search
CPC ....... G01N 33/6869; G01N 2333/5428; G01N 33/6863; G01N 33/6866; G01N 33/6872; G01N 33/6893; G01N 33/74; G01N 2333/475; G01N 2333/49; G01N 2333/505; G01N 2333/521; G01N 2333/54; G01N 2333/545; G01N 2333/57; G01N 2800/26; G01N 2800/60; C12N 5/0645; C12N 2501/23; C12N 2506/115
See application file for complete search history.

(56) References Cited

U.S. PATENT DOCUMENTS

2016/0297860 A1 10/2016 Zlotnik et al.

FOREIGN PATENT DOCUMENTS

| CN | 105764527 A | 7/2016 |
| WO | 2015077506 | 5/2015 |

OTHER PUBLICATIONS

Zhou et al., Effect of IFN-γ and IL-10 on the Expression of B-Cell Activating Factor in HL-60 Cells, Modern Immunology, No. 1, Jan. 30, 2009, pp. 50-53. English Abstract on p. 1.
Catalan-Dibene et al., Identification of IL-40, a Novel B Cell-Associated Cytokine, The Journal of Immunology, vol. 199, No. 9, Oct. 4, 2017, pp. 3326-3335.
Danis et al., Cytokine Regulation of Human Monocyte Interleukin-1 (IL-1) Production in Vitro. Enhancement of IL-1 Production by Interferon (IFN) Gamma, Tumour Necrosis Factor-Alpha, IL-2 and IL-1, and Inhibition by IFN-Alpha, Clinical and Experimental Immunology, vol. 80, No. 3, Jun. 1, 1990, pp. 435-443.
Jovanovic et al., IL-17 Stimulates the Production and Expression of Proinflammatory Cytokines, IL-β and TNF-α, by Human Macrophages, The Journal of Immunology, vol. 160, No. 7, Apr. 1, 1998, pp. 3513-3521.
Luu et al., B Cells Participate in Tolerance and Autoimmunity Through Cytokine Production, Journal Autoimmunity, vol. 47, No. 1, Feb. 18, 2014, pp. 1-12. (Abstract).
International Application No. PCT/US2020/016778, International Search Report and Written Opinion mailed on Aug. 31, 2020, 16 pages.
Chinese Application No. 202080026267.1, Office Action mailed on Jan. 26, 2024, 10 pages.
European Application No. 20709880.7, Office Action mailed on Jan. 3, 2024, 5 pages.
International Application No. PCT/US2020/016778, International Preliminary Report on Patentability mailed on Aug. 19, 2021, 11 pages.
International Application No. PCT/US2020/016778, Invitation to Pay Addition Fees and Where Applicable, Protest Fee mailed on Jul. 3, 2020, 11 pages.
Chinese Application No. 202080026267.1, Notice of Decision to Grant mailed on Jan. 1, 2025, 4 pages (2 pages of Original Document and 2 pages of English Translation).
Dabbagh-Gorjani, A Comprehensive Review on the Role of Interleukin-40 as a Biomarker for Diagnosing Inflammatory Diseases, Auto-immune Diseases, vol. 2024, No. 1, Mar. 1, 2024, pp. 1-8.
Guggino et al., Possible Role for IL-40 and IL-40-Producing Cells in the Lymphocytic Infiltrated Salivary Glands of Patients with Primary Sjogren's Syndrome, Rheumatic & Musculoskeletal Diseases Open, vol. 9, No. 2, May 1, 2023, pp. 1-13.

*Primary Examiner* — Gregory S Emch
*Assistant Examiner* — Mckenzie A Dunn
(74) *Attorney, Agent, or Firm* — Kilpatrick Townsend & Stockton LLP

(57) ABSTRACT

The technology relates in part to methods for detecting the activity of IL-40 and modified versions thereof. The technology also relates in part to uses of IL-40 for promoting cell differentiation.

17 Claims, 10 Drawing Sheets
Specification includes a Sequence Listing.

USES OF IL-40 AND METHODS FOR DETECTING IL-40 ACTIVITY

RELATED PATENT APPLICATION(S)

This patent application is a continuation application of PCT/US2020/016778, filed Feb. 5, 2020, which application claims the benefit of priority to U.S. provisional patent application No. 62/803,037 filed on Feb. 8, 2019, entitled USES OF IL-40 AND METHODS FOR DETECTING IL-40 ACTIVITY, naming Marcela Hernandez RUIZ et al. as inventors. The entire contents of the foregoing applications are incorporated herein by reference, including all text, tables and drawings.

SEQUENCE LISTING

The instant application contains a Sequence Listing which has been submitted electronically in ASCII format and is hereby incorporated by reference in its entirety. Said ASCII copy, created on Feb. 24, 2020, is named BLD-2001-PC_SL.txt and is 85,143 bytes in size.

FIELD

The technology relates in part to methods for detecting the activity of IL-40 and modified versions thereof. The technology also relates in part to uses of IL-40 for promoting cell differentiation.

BACKGROUND

Cytokines are small secreted proteins involved in immune responses, host defense, inflammation, and immune system development. Cytokines generally exert their effects by binding specific receptors on the membrane of target cells. Examples of cytokines include interleukins, chemokines, interferons, and members of the tumor necrosis factor super-family. Certain cytokines are involved in autoimmune diseases, cancer, endocrine disorders, and other ailments; and may be useful for immunotherapy.

IL-40 is generally considered a B cell-associated cytokine, and may be useful for certain research applications (e.g., studying the pathogenesis of certain diseases; studying immune cell activation and differentiation), diagnostics, and/or certain types of immunotherapy. Provided herein are methods for detecting the activity of IL-40 (e.g., recombinant IL-40, and modified versions thereof). IL-40 may be involved in promoting differentiation of certain immune cells. Provided herein are methods for inducing immune cell differentiation using IL-40.

SUMMARY

Provided herein, in some aspects, are methods for assessing activity of an IL-40 polypeptide comprising a) contacting a cell with a first composition comprising an IL-40 polypeptide; b) measuring production by the cell of one or more cytokines, chemokines, and/or growth factors chosen from CCL2, CCL3, CCL4, CCL5, CCL11, CXCL8, CXCL10, IL-1RA, erythropoietin, PDGF-AA, and VEGF, thereby measuring cytokine, chemokine, and/or growth factor production; and c) detecting the activity of the IL-40 polypeptide in the first composition according to the cytokine, chemokine, and/or growth factor production measured in (b).

Also provided herein, in some aspects, are methods for assessing activity of an IL-40 polypeptide comprising a) contacting a cell with a first composition comprising an IL-40 polypeptide and a second composition comprising a co-stimulant; b) measuring production by the cell of one or more cytokines, chemokines, and/or growth factors chosen from CCL2, CCL3, CCL4, CCL5, CCL11, CCL17, CCL20, CXCL1, CXCL5, CXCL8, CXCL9, CXCL10, CXCL11, IL-1RA, IL-6, erythropoietin, PDGF-AA, and VEGF, thereby measuring cytokine, chemokine, and/or growth factor production; and c) detecting the activity of the IL-40 polypeptide in the first composition according to the cytokine, chemokine, and/or growth factor production measured in (b).

Also provided herein, in some aspects, are methods for assessing activity of an IL-40 polypeptide comprising a) contacting a population of monocytes with a first composition comprising an IL-40 polypeptide; b) detecting monocyte to macrophage differentiation and/or monocyte activation in the population; and c) assessing the activity of the IL-40 polypeptide in the first composition according to the monocyte to macrophage differentiation and/or monocyte activation detected in (b).

Also provided herein, in some aspects, are methods for inducing differentiation of a monocyte to a macrophage, comprising contacting a monocyte with a first composition comprising an IL-40 polypeptide.

Also provided herein, in some aspects, are kits, comprising a) a first composition comprising one or more polypeptides chosen from IFN-γ, GM-CSF, IFN-α, IL-1β, IL-4, IL-10, IL-13, M-CSF, TGF-β, and TNF-α; b) one or more components for measuring cytokine, chemokine, and/or growth factor production, where the cytokines, chemokines and/or growth factors are chosen from one or more of CCL2, CCL3, CCL4, CCL5, CCL11, CCL17, CCL20, CXCL1, CXCL5, CXCL8, CXCL9, CXCL10, CXCL11, IL-1RA, IL-6, erythropoietin, PDGF-AA, and VEGF; and c) instructions for use.

Also provided herein, in some aspects, are methods for detecting the presence of IL-40 receptor on a cell comprising a) contacting the cell with a first composition comprising a stimulant and a second composition comprising recombinant human IL-40 polypeptide; b) incubating the cell with a labeled anti-IL-40 antibody; and c) measuring the amount of labeled anti-IL-40 antibody that binds the cell, thereby detecting the presence of the IL-40 receptor.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

(Panel J), CXCL1 (Panel K), CXCL11 (Panel L), and CCL4 (Panel M) were observed in PBMCs. Results are shown as the media±SEM.

Figure 14:
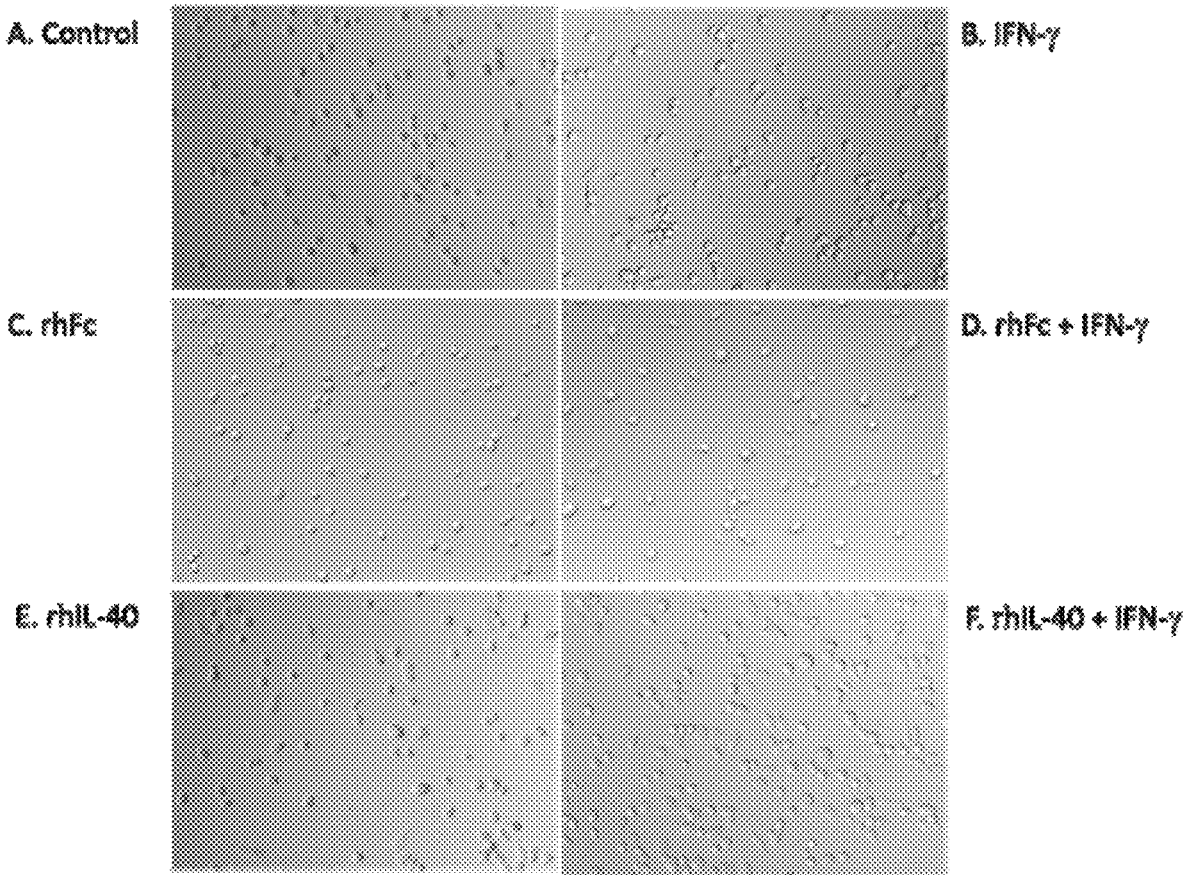

FIG. 14, panels A-F, shows THP-1 morphological changes induced by rhIL-40, in the presence or absence of IFN-γ.

Figure 15:
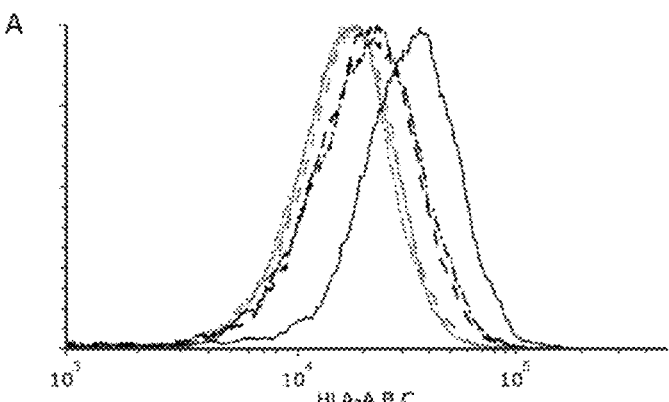
Figure 15:
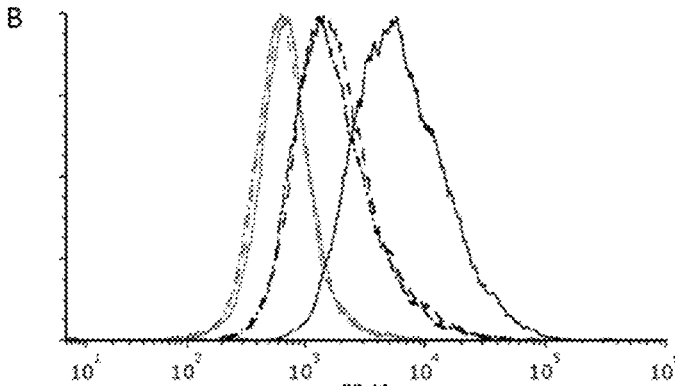
Figure 15:
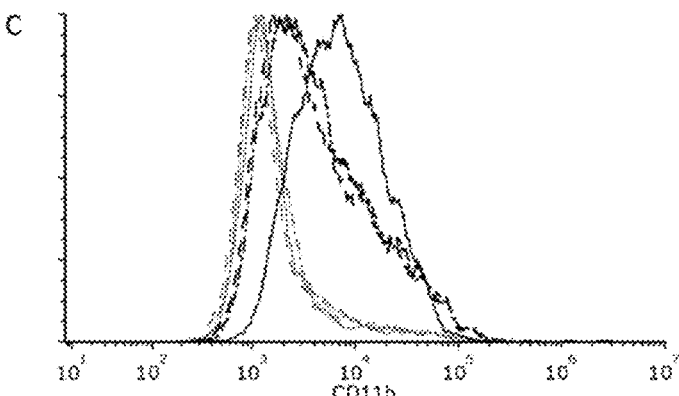

FIG. 15, panels A-C, shows an effect of rhIL-40 plus IFN-γ on the expression of HLA-A, B, C (Panel A), CD40 (Panel B), and CD11 b (Panel C) on the surface of THP-1 monocytes. Results are shown as histograms, and stimuli are represented as follows: unstimulated cells (dotted gray line), Fc fraction (dashed gray line), rhIL-40 (solid gray line), IFN-γ (dotted black line), Fc fraction plus IFN-γ (dashed black line), and rhIL-40 plus IFN-γ (solid black line).

Figure 16:
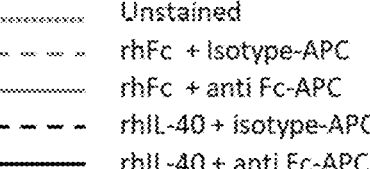
Figure 16:
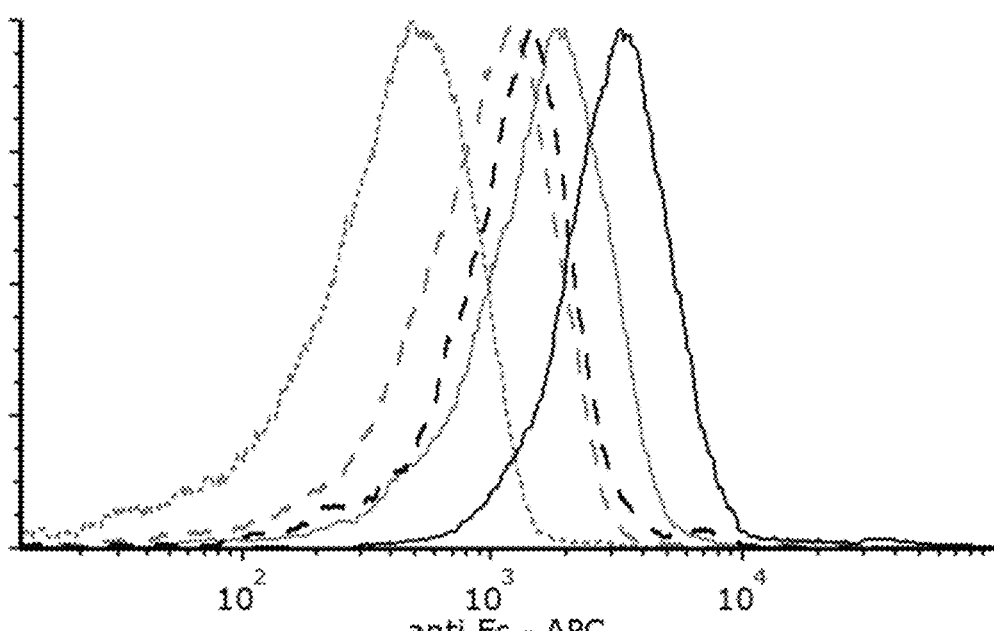

FIG. 16 shows an effect of rhIL40 on the expression of IL40 receptor on THP-1 cells. Results are shown as histograms, and represented as follows: unstained cells (dotted gray line), rhFc fraction+isotype–APC (dashed gray line), rhFc fraction+anti Fc–APC (solid gray line), rhIL40+isotype–APC (dashed black line), rhIL40+anti Fc–APC (solid black line).

DETAILED DESCRIPTION

IL-40 may useful for certain research applications, diagnostics, and/or immunotherapy. Accordingly, bioassays for assessing the activity of IL-40, recombinant IL-40, IL-40 variants, IL-40 fragments, and other modified versions of IL-40 would be useful for developing practical applications for IL-40. Provided herein are methods for assessing the activity of IL-40. Also provided herein are methods for inducing cell differentiation using IL-40.

IL-40

Provided herein are methods for assessing the activity of an interleukin-40 (IL-40) polypeptide. Also provided herein are methods for inducing cell differentiation using interleukin-40 (IL-40). Interleukin-40, which may be referred to as IL-40, IL40, C17orf99 (chromosome 17 open reading frame 99), GLPG464, or UNQ464, is a cytokine involved in the regulation of humoral immunity and is generally associated with B cells. IL-40 is expressed in bone marrow, fetal liver, and certain human B cell lymphomas, and IL-40 expression may be induced in peripheral B cells upon activation. IL-40 is present in mammalian genomes, and the IL-40 gene (C17orf99) encodes a small (~27-kDa) secreted protein unrelated to other cytokine families, indicating a function in mammalian immune responses. Naive B cells can express IL-40 upon activation, and production increases following culture with various cytokines, such as IL-4 and TGF-β1.

IL-40 generally is present in mammals, including human, mouse, rat, and chimpanzee. An example human IL-40 nucleic acid sequence is provided herein as SEQ ID NO: 2 (GENBANK Accession No. NM_001163075.1), and an example human IL-40 amino acid sequence is provided herein as SEQ ID NO: 1 (GENBANK Accession No. NP_001156547.1). An example mouse IL-40 nucleic acid sequence is provided herein as SEQ ID NO: 4 (GENBANK Accession No. NM_029964.1), and an example mouse IL-40 amino acid sequence is provided herein as SEQ ID NO: 3 (GENBANK Accession No. NP_084240.1).

An IL-40 polypeptide may refer to a precursor IL-40 polypeptide (includes the signal peptide) or a mature IL-40 polypeptide (excludes the signal peptide). In some embodiments, an IL-40 polypeptide is a precursor IL-40 polypeptide (e.g., a precursor human IL-40 polypeptide comprising amino acids 1-265 of SEQ ID NO: 1; a precursor mouse IL-40 polypeptide comprising amino acids 1-252 of SEQ ID NO: 3). In some embodiments, an IL-40 polypeptide is a mature IL-40 polypeptide (e.g., a mature human IL-40 polypeptide comprising amino acids 21-265 of SEQ ID NO: 1; a mature mouse IL-40 polypeptide comprising amino acids 19-252 of SEQ ID NO: 3).

In some embodiments, an IL-40 polypeptide is a recombinant IL-40 polypeptide. A recombinant IL-40 polypeptide typically is an IL-40 polypeptide encoded by DNA (i.e., IL-40 nucleic acid sequence) that has been cloned in a vector or system that supports expression of the DNA and translation of messenger RNA. In some embodiments, an IL-40 polypeptide is a recombinant human IL-40 polypeptide (rhIL-40). In some embodiments, an IL-40 polypeptide is a recombinant mouse IL-40 polypeptide (rmIL-40).

An IL-40 polypeptide herein may refer to an unmodified IL-40 polypeptide. An unmodified polypeptide generally refers to a native or wild-type full-length (precursor or mature) polypeptide having no amino acid substitutions, no insertions, no deletions, no chemical modifications, no amino acid side-chain modifications, no tags, no detectable labels, no fusions, and the like.

An IL-40 polypeptide herein may refer to a modified IL-40 polypeptide. A modified polypeptide generally refers to a polypeptide comprising one or more amino acid substitutions, one or more insertions, one or more deletions, one or more chemical modifications, one or more amino acid side-chain modifications, one or more tags, one or more detectable labels, one or more fusions, and the like and combinations thereof. Modifications may include, for example, addition of one or more fluorophores, glycosylation, prenylation, PEGylation, attachment to a solid surface, biotinylation, antibody conjugation, conjugation to a therapeutic agent, chemical modifications at cysteine (e.g., aminoethylation, iodoacetamides, maleimides, Dha formation, disulfide formation, reaction of Dha with thiols, and desulfurization of disulfides), incorporation of one or more unnatural amino acids, and the like and combinations thereof.

In some embodiments, an IL-40 polypeptide refers to an IL-40 variant or mutant. Such variants include, for example, deletions from, and/or insertions into and/or substitutions of, residues within the amino acid sequences of an IL-40 polypeptide. An IL-40 variant may include any combination of deletion, insertion, and substitution. In some embodiments, an IL-40 polypeptide comprises one or more amino acid substitutions. These variants have at least one amino acid residue removed from the IL-40 polypeptide and a different residue inserted in its place. For example, an IL-40 variant may comprise 1, 2, 3, 4, 5, 6, 7, 8, 9, 10 or more amino acid substitutions. An IL-40 variant may include conservative substitutions and/or non-conservative substitutions, and the variants may be screened using one or more bioassays described herein for assessing IL-40 activity. Examples of substitutions are listed below:

Example Amino Acid Residue Substitutions

Ala (A) val; leu; ile; val
Arg (R) lys; gln; asn; lys
Asn (N) gln; his; asp, lys; gln; arg
Asp (D) glu; asn
Cys (C) ser; ala
Gln (Q) asn; glu
Glu (E) asp; gln
Gly (G) ala
His (H) asn; gln; lys; arg
Ile (I) leu; val; met; ala; leu; phe; norleucine
Leu (L) norleucine; ile; val; ile; met; ala; phe Lys (K) arg; gln; asn
Met (M) leu; phe; ile
Phe (F) leu; val; ile; ala; tyr
Pro (P) ala
Ser (S) thr
Thr (T) ser
Trp (VV) tyr; phe
Tyr (Y) trp; phe; thr; ser
Val (V) ile; leu; met; phe; ala; norleucine Substantial modifications in the biological properties of an IL-40 polypeptide may be accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, and/or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions typically entail exchanging a member of one of these classes for another class.

In some embodiments, an IL-40 polypeptide comprises one or more insertions. In some embodiments, an IL-40 polypeptide comprises one or more insertions, where each insertion comprises one or more amino acids. For example, each insertion may comprise 1, 2, 3, 4, 5, 6, 7, 8, 9, 10 or more inserted amino acids. In some embodiments, an IL-40 polypeptide comprises one or more deletions. In some embodiments, an IL-40 polypeptide comprises one or more deletions, where each deletion removes one or more amino acids from the full length amino acid sequence. For example, each deletion may remove 1, 2, 3, 4, 5, 6, 7, 8, 9, 10 or more amino acids.

In some embodiments, an IL-40 polypeptide comprises a fused polypeptide. A fused polypeptide may be referred to as a fusion protein or chimeric protein. Fused polypeptides typically are created through the joining of two or more genes that code for separate proteins. Translation of this fusion construct may result in a single or multiple polypeptides with functional properties derived from each of the original proteins. Recombinant fusion proteins may be created artificially by recombinant DNA technology for use in biological research or therapeutics. Examples of fused polypeptides include IL-40 fused with a fluorescent protein tag (e.g., green fluorescent protein (GFP)), therapeutic protein (e.g., antibody), or any protein tag described herein. In some embodiments a fused polypeptide comprises a linker (e.g., flexible linker, rigid linker, cleavable linker).

In some embodiments, an IL-40 polypeptide comprises one or more tags (e.g., one or more amino acid or peptide tags; one or more affinity tags). Tags may facilitate detection, isolation and/or purification of an IL-40 polypeptide. A tag sometimes specifically binds a molecule or moiety of a solid phase or a detectable label, for example, thereby having utility for isolating, purifying and/or detecting an IL-40 polypeptide. In some embodiments, a tag comprises one or more of the following elements: Fc (derived from immunoglobulin Fc domain), FLAG (e.g., DYKDDDDKG (SEQ ID NO: 48)), V5 (e.g., GKPIPNPLLGLDST (SEQ ID NO: 49)), c-MYC (e.g., EQKLISEEDL (SEQ ID NO: 50)), HSV (e.g., QPELAPEDPED (SEQ ID NO: 51)), influenza hemagglutinin, HA (e.g., YPYDVPDYA (SEQ ID NO: 52)), VSV-G (e.g., YTDIEMNRLGK (SEQ ID NO: 53)), bacterial glutathione-S-transferase, maltose binding protein, a streptavidin- or avidin-binding tag (e.g., pcDNA™6 BioEase™ Gateway® Biotinylation System (Invitrogen)), thioredoxin, β-galactosidase, VSV-glycoprotein, a fluorescent protein (e.g., green fluorescent protein or one of its many color variants (e.g., yellow, red, blue)), a polylysine or polyarginine sequence, a polyhistidine sequence (e.g., His6 (SEQ ID NO: 54)) or other sequence that chelates a metal (e.g., cobalt, zinc, copper), and/or a cysteine-rich sequence that binds to an arsenic-containing molecule. In certain embodiments, a cysteine-rich tag comprises the amino acid sequence CC-Xn-CC (SEQ ID NO: 55), where X is any amino acid and n is 1 to 3, and the cysteine-rich sequence sometimes is CCPGCC (SEQ ID NO: 56). In certain embodiments, the tag comprises a cysteine-rich element and a polyhistidine element (e.g., CCPGCC (SEQ ID NO: 56) and His6 (SEQ ID NO: 54)).

A tag may bind to a binding partner. For example, some tags bind to an antibody (e.g., FLAG) and sometimes specifically bind to a small molecule. For example, a polyhistidine tag specifically chelates a bivalent metal, such as copper, zinc and cobalt; a polylysine or polyarginine tag specifically binds to a zinc finger; a glutathione S-transferase tag binds to glutathione; and a cysteine-rich tag specifically binds to an arsenic-containing molecule. Arsenic-containing molecules include LUMIO™ agents (Invitrogen, California), such as FlAsH™ (EDT2[4',5'-bis(1,3,2-dithioarsolan-2-yl)fluorescein-(1,2-ethanedithiol)2]) and ReAsH reagents. Such antibodies and small molecules sometimes are linked to a solid phase for isolation of the target protein or target peptide.

In some embodiments, an IL-40 polypeptide comprises one or more detectable markers or labels. In some embodiments, an IL-40 polypeptide is conjugated to a detectable marker or label. For example, for research and diagnostic applications, a modified IL-40 polypeptide may be labeled with a detectable moiety. Numerous labels are available which generally include radioisotopes (e.g., $^{35}$S, $^{14}$C, $^{125}$I, $^{3}$H, and $^{131}$I), fluorescent labels (e.g., rare earth chelates (europium chelates) or fluorescein and its derivatives, rhodamine and its derivatives, dansyl, Lissamine, phycoerythrin, Texas Red and Brilliant Violet™), and enzyme-substrate labels (e.g., described in U.S. Pat. No. 4,275,149, which is incorporated by reference herein, luciferases (e.g., firefly luciferase and bacterial luciferase; U.S. Pat. No. 4,737,456, which is incorporated by reference herein), luciferin, 2,3-dihydrophthalazinediones, malate dehydrogenase, urease, peroxidase such as horseradish peroxidase (HRP), alkaline phosphatase, beta-galactosidase, glucoamylase, lysozyme, saccharide oxidases (e.g., glucose oxidase, galactose oxidase, and glucose-6-phosphate dehydrogenase), heterocyclicoxidases (such as uricase and xanthine oxidase), lactoperoxidase, microperoxidase, and the like).

In certain instances, a label is indirectly conjugated to an IL-40 polypeptide. For example, an IL-40 polypeptide may be conjugated with biotin and any suitable label mentioned above may be conjugated with avidin, or vice versa. Biotin binds selectively to avidin and thus, the label can be conjugated with an IL-40 polypeptide in this indirect manner. Alternatively, to achieve indirect conjugation of a label with an IL-40 polypeptide, the IL-40 polypeptide is conjugated with a small hapten (e.g., digoxin) and one of the types of labels mentioned above is conjugated with an anti-hapten antibody (e.g., anti-digoxin antibody).

In some embodiments, an IL-40 polypeptide refers to a fragment of an IL-40 polypeptide. Generally, an IL-40 fragment contains fewer amino acids than a full-length mature IL-40. For example, an IL-40 fragment may include a portion of the mature human IL-40 polypeptide (i.e., a portion of amino acids 21-265 of SEQ ID NO: 1), or a portion of the mature mouse IL-40 polypeptide (i.e. a portion of amino acids 19-252 of SEQ ID NO: 3). Full-length mature human IL-40 is 245 amino acids in length. Accordingly, fragments of human IL-40 may be 244 amino acids in length or shorter. Full-length mature mouse IL-40 is 234 amino acids in length. Accordingly, fragments of mouse IL-40 may be 233 amino acids in length or shorter.

In some embodiments, an IL-40 polypeptide refers to a functional fragment of an IL-40 polypeptide. Methods for assessing the activity of IL-40 polypeptides and functional fragments of IL-40 are provided herein. In some embodiments, a functional fragment of IL-40 is a fragment that exhibits at least 50% of the activity of a full-length mature IL-40. For example, a functional fragment of IL-40 is a fragment that exhibits at least 50%, at least 60%, at least 70%, at least 80%, at least 90%, at least 95%, or more of the activity of a full-length mature IL-40.

In some embodiments, an IL-40 polypeptide is immobilized on a solid support or substrate. In some embodiments, an IL-40 polypeptide is non-diffusively immobilized on a solid support (e.g., the IL-40 polypeptide does not detach from the solid support). A solid support or substrate can be any physically separable solid to which an IL-40 polypeptide can be directly or indirectly attached including, but not limited to, surfaces provided by microarrays and wells, and particles such as beads (e.g., paramagnetic beads, magnetic beads, microbeads, nanobeads), microparticles, and nanoparticles. Solid supports also can include, for example, chips, columns, optical fibers, wipes, filters (e.g., flat surface filters), one or more capillaries, glass and modified or functionalized glass (e.g., controlled-pore glass (CPG)), quartz, mica, diazotized membranes (paper or nylon), polyformaldehyde, cellulose, cellulose acetate, paper, ceramics, metals, metalloids, semiconductive materials, quantum dots, coated beads or particles, other chromatographic materials, magnetic particles; plastics (including acrylics, polystyrene, copolymers of styrene or other materials, polybutylene, polyurethanes, TEFLON™, polyethylene, polypropylene, polyamide, polyester, polyvinylidenedifluoride (PVDF), and the like), polysaccharides, nylon or nitrocellulose, resins, silica or silica-based materials including silicon, silica gel, and modified silicon, Sephadex®, Sepharose®, carbon, metals (e.g., steel, gold, silver, aluminum, silicon and copper), inorganic glasses, conducting polymers (including polymers such as polypyrole and polyindole); micro or nanostructured surfaces such as nucleic acid tiling arrays, nanotube, nanowire, or nanoparticulate decorated surfaces; or porous surfaces or gels such as methacrylates, acrylamides, sugar polymers, cellulose, silicates, or other fibrous or stranded polymers. In some embodiments, the solid support or substrate may be coated using passive or chemically-derivatized coatings with any number of materials, including polymers, such as dextrans, acrylamides, gelatins or agarose. Beads and/or particles may be free or in connection with one another (e.g., sintered). In some embodiments, a solid support or substrate can be a collection of particles. In some embodiments, the particles can comprise silica, and the silica may comprise silica dioxide. In some embodiments the silica can be porous, and in certain embodiments the silica can be nonporous. In some embodiments, the particles further comprise an agent that confers a paramagnetic property to the particles. In certain embodiments, the agent comprises a metal, and in certain embodiments the agent is a metal oxide, (e.g., iron or iron oxides, where the iron oxide contains a mixture of Fe2+ and Fe3+). An IL-40 polypeptide may be linked to a solid support by covalent bonds or by non-covalent interactions and may be linked to a solid support directly or indirectly (e.g., via an intermediary agent such as a spacer molecule or biotin).

Stimulants and Co-Stimulants

Certain methods provided herein include use of a stimulant or co-stimulant. Use of stimulants and co-stimulants may be included, for example, in methods for assessing the activity of an IL-40 polypeptide, and/or in methods for inducing cell differentiation (e.g., inducing differentiation of a monocyte to a macrophage). A stimulant may be used in certain instances (e.g., to stimulate a cell prior to exposure to IL-40). A co-stimulant may be used in certain instances (e.g., to co-stimulate a cell during IL-40 exposure). In some embodiments, a cell or population of cells is contacted with a stimulant/co-stimulant. In some embodiments, a cell or population of cells is simultaneously contacted with a stimulant/co-stimulant and an IL-40 polypeptide. In some embodiments, a cell or population of cells is contacted with a stimulant/co-stimulant prior to being contacted with an IL-40 polypeptide.

In certain instances, a stimulant/co-stimulant can strengthen or enhance the effect of IL-40 on a cell or a population of cells. For example, a stimulant/co-stimulant can enhance production of certain cytokines, chemokines, and/or growth factors in response to IL-40 stimulation. A stimulant/co-stimulant also can enhance certain types of cell differentiation in response to IL-40 stimulation. In certain instances, a stimulant/co-stimulant can provide a synergistic enhancement when combined with IL-40. For example, a stimulant/co-stimulant can synergistically enhance production of certain cytokines, chemokines, and/or growth factors in response to IL-40 stimulation. A stimulant/co-stimulant also can synergistically enhance certain types of cell differentiation in response to IL-40 stimulation. An enhancement afforded by a stimulant or co-stimulant may be additive, multiplicative, or exponential.

Any suitable stimulant/co-stimulant may be used in conjunction with the methods provided herein. In some embodiments, a stimulant/co-stimulant comprises a soluble/secreted protein. In some embodiments, a stimulant/co-stimulant comprises a cytokine. In some embodiments, a stimulant/co-stimulant comprises a chemokine. Non-limiting examples of stimulants/co-stimulants include interferon-γ (IFN-γ), interferon-α (IFN-α), lipopolysaccharides (LPS), granulocyte-macrophage colony-stimulating factor (GM-CSF), interleukin 1 beta (IL-1β), interleukin 4 (IL-4), interleukin 13 (IL-13), macrophage colony-stimulating factor (M-CSF), infection (e.g., fungal infection, helminth infection), immune complexes, interleukin-1 receptor (IL-1R), interleukin 10 (IL-10), transforming growth factor beta (TGF-β), glucocorticoids, interleukin 6 (IL-6), leukemia inhibitory factor (LIF), tumor necrosis factor alpha (TNF-α), adenosine, complement components, and interleukin 32 (IL-32).

IFN-γ

Certain methods provided herein include use of interferon-γ (IFN-γ) as a stimulant or co-stimulant. Interferon-γ (also referred to as IFN-γ, IFNγ, IFN-g, IFNg, IFN-gamma, interferon gamma, immune interferon, type II interferon) is a dimerized soluble cytokine and a type II class of interferon. IFN-γ generally is involved in innate and adaptive immunity against certain viral, bacterial, and protozoal infections. IFN-γ can function as an activator of macrophages and inducer of Class II major histocompatibility complex (MHC) molecule expression. IFN-γ can inhibit viral replication directly, and can provide immunostimulatory and immunomodulatory effects. Aberrant IFN-γ expression often is associated with a number of autoinflammatory and autoimmune diseases. IFN-γ typically is produced by natural killer (NK) and natural killer T (NKT) cells as part of the innate immune response; by CD4 Th1 and CD8 cytotoxic T lymphocyte (CTL) effector T cells once antigen-specific immunity develops; and by non-cytotoxic innate lymphoid cells (ILC).

Any suitable IFN-γ, or functional fragment, or modified version thereof, may be used in conjunction with the methods described herein (e.g., as a co-stimulant with IL-40; as a stimulant prior to IL-40 exposure). In some embodiments, IFN-γ is a human IFN-γ. An example human IFN-γ nucleic acid sequence is provided herein as SEQ ID NO: 6 (GENBANK Accession No. NM_000619.3), and an example human IFN-γ amino acid sequence is provided herein as SEQ ID NO: 5 (GENBANK Accession No. NP_000610.2). In some embodiments, IFN-γ is a mouse IFN-γ. An example mouse IFN-γ nucleic acid sequence is provided herein as SEQ ID NO: 8 (GENBANK Accession No. NM_008337.4), and an example mouse IFN-γ amino acid sequence is provided herein as SEQ ID NO: 7 (GENBANK Accession No. NP_032363.1).

IFN-γ may refer to a precursor IFN-γ polypeptide (includes the signal peptide) or a mature IFN-γ polypeptide (excludes the signal peptide). In some embodiments, IFN-γ is a precursor IFN-γ polypeptide (e.g., a precursor human IFN-γ polypeptide comprising amino acids 1-166 of SEQ ID NO: 5; a precursor human IFN-γ polypeptide comprising amino acids 1-161 of SEQ ID NO: 5; a precursor mouse IFN-γ polypeptide comprising amino acids 1-155 of SEQ ID NO: 7). In some embodiments, an IFN-γ polypeptide is a mature IFN-γ polypeptide (e.g., a mature human IFN-γ polypeptide comprising amino acids 24-166 of SEQ ID NO: 5; a mature human IFN-γ polypeptide comprising amino acids 24-161 of SEQ ID NO: 5; a mature mouse IFN-γ polypeptide comprising amino acids 23-155 of SEQ ID NO: 7).

In some embodiments, IFN-γ is a recombinant IFN-γ polypeptide. A recombinant IFN-γ polypeptide typically is an IFN-γ polypeptide encoded by DNA (i.e., IFN-γ nucleic acid sequence) that has been cloned in a vector or system that supports expression of the DNA and translation of messenger RNA. In some embodiments, IFN-γ is a recombinant human IFN-γ polypeptide (rhIFN-γ). In some embodiments, IFN-γ is a recombinant mouse IFN-γ polypeptide (rmIFN-γ).). In some embodiments, IFN-γ is a commercially available recombinant human IFN-γ (e.g., BioLegend cat #570202). In some embodiments, IFN-γ is a commercially available recombinant mouse IFN-γ (e.g., BioLegend cat #575302).

IFN-γ may refer to an unmodified IFN-γ polypeptide, a modified IFN-γ polypeptide, an IFN-γ variant, an IFN-γ mutant; or a fragment thereof or a functional fragment thereof. Unmodified polypeptides, modified polypeptides, mutants, variants, and fragments are described herein. In some embodiments, IFN-γ refers to a polypeptide comprising an amino acid sequence that is at least about 75% identical to SEQ ID NO: 5 or SEQ ID NO: 7. For example, IFN-γ may refer to a polypeptide comprising an amino acid sequence that is at least about 75%, 80%, 85%, 90%, 91%, 92%, 93%, 94%, 95%, 96%, 97%, 98%, or 99% identical to SEQ ID NO: 5 or SEQ ID NO: 7.

In some embodiments, IFN-γ refers to a fragment of an IFN-γ polypeptide. Generally, an IFN-γ fragment contains fewer amino acids than a full-length mature IFN-γ. For example, an IFN-γ fragment may include a portion of the mature human IFN-γ polypeptide (e.g., a portion of amino acids 24-166 of SEQ ID NO: 5; a portion of amino acids 24-161 of SEQ ID NO: 5), or a portion of the mature mouse IFN-γ polypeptide (i.e. a portion of amino acids 23-155 of SEQ ID NO: 7). One example full-length mature human IFN-γ is 143 amino acids in length. Accordingly, fragments of human IFN-γ may be 142 amino acids in length or shorter. Another example full-length mature human IFN-γ is 138 amino acids in length. Accordingly, fragments of human IFN-γ may be 137 amino acids in length or shorter. Full-length mature mouse IFN-γ is 133 amino acids in length. Accordingly, fragments of mouse IFN-γ may be 132 amino acids in length or shorter.

In some embodiments, IFN-γ refers to a functional fragment of an IFN-γ polypeptide. Any suitable method for assessing the activity of IFN-γ and functional fragments of IFN-γ may be used to determine whether an IFN-γ fragment is a functional fragment. For example, one assay for assessing IFN-γ activity is the induction of an antiviral state in target cells, sometimes referred to as a cytopathic protection effect (CPE) assay. An example CPE assay uses A549 human lung carcinoma cells challenged with encephalomyocarditis virus (EMCV) and the effects are compared to a standard for human IFN-γ (e.g., Gxg01-902-535, BEI Resources). In some embodiments, a functional fragment of IFN-γ is a fragment that exhibits at least 50% of the activity of an IFN-γ standard or a full-length mature IFN-γ. For example, a functional fragment of IFN-γ is a fragment that exhibits at least 50%, at least 60%, at least 70%, at least 80%, at least 90%, at least 95%, or more of the activity of an IFN-γ standard or a full-length mature IFN-γ.

IL-4

Certain methods provided herein include use of interleukin 4 (IL-4) as a stimulant or co-stimulant. Interleukin 4 (also referred to as IL-4, B cell growth factor 1 (BCGF-1), B-cell stimulatory factor 1 (BSF-1), interleukin-4, lymphocyte stimulatory factor 1, MGC79402) is the primary cytokine implicated in the development of Th2-mediated responses, which is associated with allergy and asthma. The Type I receptor comprises IL-4Rα and the common gamma-chain (γc), which is also shared by the cytokines IL-2, -7, -9, -15 and -21 and is present in hematopoietic cells. IL-4 can use the type II complex, comprising IL-4Rα and IL-13Rα1, which is present in non-hematopoietic cells. This second receptor complex is a functional receptor for IL-13, which shares approximately 25% homology with IL-4. The type I receptor complex can be formed only by IL-4 and is active in Th2 development. In contrast, the type II receptor complex formed by either IL-4 or IL-13 is more active during airway hypersensitivity and mucus secretion and is not found in T cells.

Any suitable IL-4, or functional fragment, or modified version thereof, may be used in conjunction with the methods described herein (e.g., as a co-stimulant with IL-40; as a stimulant prior to IL-40 exposure). In some embodiments, IL-4 is a human IL-4. An example human IL-4 nucleic acid sequence is provided herein as SEQ ID NO: 13 (full mRNA sequence provided as GEN BANK Accession No. NM_000589), and an example human IL-4 amino acid sequence is provided herein as SEQ ID NO: 12 (GENBANK Accession No. NP_000580.1). In some embodiments, IL-4 is a mouse IL-4. An example mouse IL-4 nucleic acid sequence is provided herein as SEQ ID NO: 15 (full mRNA sequence provided as GENBANK Accession No. NM_021283), and an example mouse IL-4 amino acid sequence is provided herein as SEQ ID NO: 14 (GENBANK Accession No. NP_067258.1).

IL-4 may refer to a precursor IL-4 polypeptide (includes the signal peptide) or a mature IL-4 polypeptide (excludes the signal peptide). In some embodiments, IL-4 is a precursor IL-4 polypeptide (e.g., a precursor human IL-4 polypeptide comprising amino acids 1-153 of SEQ ID NO: 12; a precursor mouse IL-4 polypeptide comprising amino acids 1-140 of SEQ ID NO: 14). In some embodiments, an IL-4 polypeptide is a mature IL-4 polypeptide (e.g., a mature human IL-4 polypeptide comprising amino acids 25-153 of SEQ ID NO: 12; a mature mouse IL-4 polypeptide comprising amino acids 21-140 of SEQ ID NO: 14; a mature mouse IL-4 polypeptide comprising amino acids 23-140 of SEQ ID NO: 14).

In some embodiments, IL-4 is a recombinant IL-4 polypeptide. A recombinant IL-4 polypeptide typically is an IL-4 polypeptide encoded by DNA (i.e., IL-4 nucleic acid sequence) that has been cloned in a vector or system that supports expression of the DNA and translation of messenger RNA. In some embodiments, IL-4 is a recombinant human IL-4 polypeptide (rhIL-4). In some embodiments, IL-4 is a recombinant mouse IL-4 polypeptide (rmIL-4). In some embodiments, IL-4 is a commercially available recombinant human IL-4 (e.g., BioLegend cat #574002). In some embodiments, IL-4 is a commercially available recombinant mouse IL-4 (e.g., BioLegend cat #574302).

IL-4 may refer to an unmodified IL-4 polypeptide, a modified IL-4 polypeptide, an IL-4 variant, an IL-4 mutant; or a fragment thereof or a functional fragment thereof. Unmodified polypeptides, modified polypeptides, mutants, variants, and fragments are described herein. In some embodiments, IL-4 refers to a polypeptide comprising an amino acid sequence that is at least about 75% identical to SEQ ID NO: 12 or SEQ ID NO: 14. For example, IL-4 may refer to a polypeptide comprising an amino acid sequence that is at least about 75%, 80%, 85%, 90%, 91%, 92%, 93%, 94%, 95%, 96%, 97%, 98%, or 99% identical to SEQ ID NO: 12 or SEQ ID NO: 14.

In some embodiments, IL-4 refers to a fragment of an IL-4 polypeptide. Generally, an IL-4 fragment contains fewer amino acids than a full-length mature IL-4. For example, an IL-4 fragment may include a portion of the mature human IL-4 polypeptide (i.e., a portion of amino acids 25-153 of SEQ ID NO: 12), or a portion of the mature mouse IL-4 polypeptide (i.e. a portion of amino acids 21-140 of SEQ ID NO: 14). An example full-length mature human IL-4 is 129 amino acids in length. Accordingly, fragments of human IL-4 may be 128 amino acids in length or shorter. An example full-length mature mouse IL-4 is 120 amino acids in length. Accordingly, fragments of mouse IL-4 may be 119 amino acids in length or shorter. Another example full-length mature mouse IL-4 is 118 amino acids in length. Accordingly, fragments of mouse IL-4 may be 117 amino acids in length or shorter.

In some embodiments, IL-4 refers to a functional fragment of an IL-4 polypeptide. Any suitable method for assessing the activity of IL-4 and functional fragments of IL-4 may be used to determine whether an IL-4 fragment is a functional fragment. For example, one assay for assessing IL-4 activity is a cell proliferation assay. An example cell proliferation assay measures $ED_{50}$ of IL-4 according to dose-dependent stimulation of TF-1 cell proliferation. Another example cell proliferation assay measures $ED_{50}$ of IL-4 according to dose-dependent stimulation of CTLL-2 cell proliferation. In some embodiments, a functional fragment of IL-4 is a fragment that exhibits at least 50% of the activity of an IL-4 standard (e.g., WHO International Standard for Human IL-4 (NIBSC code: 88/656)) or a full-length mature IL-4. For example, a functional fragment of IL-4 is a fragment that exhibits at least 50%, at least 60%, at least 70%, at least 80%, at least 90%, at least 95%, or more of the activity of an IL-4 standard or a full-length mature IL-4.

IL-10

Certain methods provided herein include use of interleukin 10 (IL-10) as a stimulant or co-stimulant. Interleukin 10 (also referred to as IL-10, B-TCGF, CSIF, TGIF) was first described as a cytokine that is produced by T helper 2 (Th2) cell clones. It inhibits interferon (IFN)-γ synthesis in Th1 cells, and therefore it was initially called cytokine synthesis inhibiting factor (CSIF). Macrophages are the main source of IL-10 and its secretion can be stimulated by endotoxin (via Toll-like receptor 4, NF-κB dependent), tumor necrosis factor TNF-α (via TNF receptor p55, NF-κB-dependent), catecholamines, and IL-1. IL-10 controls inflammatory processes by suppressing the expression of proinflammatory cytokines, chemokines, adhesion molecules, as well as antigen-presenting and costimulatory molecules in monocytes/macrophages, neutrophils, and T cells. IL-10 inhibits the production of proinflammatory mediators by monocytes and macrophages such as endotoxin- and IFN-γ-induced release of IL-1α, IL-6, IL-8, G-CSF, GM-CSF, and TNF-α. In addition, it enhances the production of anti-inflammatory mediators such as IL-1RA and soluble TNFα receptors. IL-10 inhibits the capacity of monocytes and macrophages to present antigen to T cells. This is realized by downregulation of constitutive and IFNγ-induced cell surface levels of MHC class II, of costimulatory molecules such as CD86 and of some adhesion molecules such as CD58.

Any suitable IL-10, or functional fragment, or modified version thereof, may be used in conjunction with the methods described herein (e.g., as a co-stimulant with IL-40; as a stimulant prior to IL-40 exposure). In some embodiments, IL-10 is a human IL-10. An example human IL-10 nucleic acid sequence is provided herein as SEQ ID NO: 17 (full mRNA sequence provided as GENBANK Accession No. NM_000572), and an example human IL-10 amino acid sequence is provided herein as SEQ ID NO: 16 (GENBANK Accession No. NP_000563.1). In some embodiments, IL-10 is a mouse IL-10. An example mouse IL-10 nucleic acid sequence is provided herein as SEQ ID NO: 19 (full mRNA sequence provided as GENBANK Accession No. NM_010548), and an example mouse IL-10 amino acid sequence is provided herein as SEQ ID NO: 18 (GENBANK Accession No. NP_034678.1).

IL-10 may refer to a precursor IL-10 polypeptide (includes the signal peptide) or a mature IL-10 polypeptide (excludes the signal peptide). In some embodiments, IL-10 is a precursor IL-10 polypeptide (e.g., a precursor human IL-10 polypeptide comprising amino acids 1-178 of SEQ ID NO: 16; a precursor mouse IL-10 polypeptide comprising amino acids 1-178 of SEQ ID NO: 18). In some embodiments, an IL-10 polypeptide is a mature IL-10 polypeptide (e.g., a mature human IL-10 polypeptide comprising amino acids 19-178 of SEQ ID NO: 16; a mature mouse IL-10 polypeptide comprising amino acids 19-178 of SEQ ID NO: 18).

In some embodiments, IL-10 is a recombinant IL-10 polypeptide. A recombinant IL-10 polypeptide typically is an IL-10 polypeptide encoded by DNA (i.e., IL-10 nucleic acid sequence) that has been cloned in a vector or system that supports expression of the DNA and translation of messenger RNA. In some embodiments, IL-10 is a recombinant human IL-10 polypeptide (rhIL-10). In some embodiments, IL-10 is a recombinant mouse IL-10 polypeptide (rmIL-10). In some embodiments, IL-10 is a commercially available recombinant human IL-10 (e.g., BioLegend cat #715602; BioLegend cat #571002). In some embodiments, IL-10 is a commercially available recombinant mouse IL-10 (e.g., BioLegend cat #575802).

IL-10 may refer to an unmodified IL-10 polypeptide, a modified IL-10 polypeptide, an IL-10 variant, an IL-10 mutant; or a fragment thereof or a functional fragment thereof. Unmodified polypeptides, modified polypeptides, mutants, variants, and fragments are described herein. In some embodiments, IL-10 refers to a polypeptide comprising an amino acid sequence that is at least about 75% identical to SEQ ID NO: 16 or SEQ ID NO: 18. For example, IL-10 may refer to a polypeptide comprising an amino acid sequence that is at least about 75%, 80%, 85%, 90%, 91%, 92%, 93%, 94%, 95%, 96%, 97%, 98%, or 99% identical to SEQ ID NO: 16 or SEQ ID NO: 18.

In some embodiments, IL-10 refers to a fragment of an IL-10 polypeptide. Generally, an IL-10 fragment contains fewer amino acids than a full-length mature IL-10. For example, an IL-10 fragment may include a portion of the mature human IL-10 polypeptide (i.e., a portion of amino acids 19-178 of SEQ ID NO: 16), or a portion of the mature mouse IL-10 polypeptide (i.e. a portion of amino acids 19-178 of SEQ ID NO: 18). An example full-length mature human IL-10 is 160 amino acids in length. Accordingly, fragments of human IL-10 may be 159 amino acids in length or shorter. An example full-length mature mouse IL-10 is 160 amino acids in length. Accordingly, fragments of mouse IL-10 may be 159 amino acids in length or shorter.

In some embodiments, IL-10 refers to a functional fragment of an IL-10 polypeptide. Any suitable method for assessing the activity of IL-10 and functional fragments of IL-10 may be used to determine whether an IL-10 fragment is a functional fragment. For example, one assay for assessing IL-10 activity is an IFN-γ inhibition assay. An example IFN-γ inhibition assay measures the extent to which IL-10 inhibits the induction of INF-γ in PHA activated human PBMC. Another assay for assessing IL-10 activity involves dose dependent stimulation MC/9 cell proliferation. In some embodiments, a functional fragment of IL-10 is a fragment that exhibits at least 50% of the activity of an IL-10 standard or a full-length mature IL-10. For example, a functional fragment of IL-10 is a fragment that exhibits at least 50%, at least 60%, at least 70%, at least 80%, at least 90%, at least 95%, or more of the activity of an IL-10 standard or a full-length mature IL-10.

TGF-β

Certain methods provided herein include use of transforming growth factor beta (TGF-β) as a stimulant or co-stimulant. Transforming growth factor beta (also referred to as TGF-β, TGF-β1, TGFB, DPD1, transforming growth factor, Transforming Growth Factor Beta 1, TGF-Beta-1) is synthesized in cells as a 390-amino acid polypeptide. Furin cleaves the protein at residue 278, yielding an N-terminal cleavage product which corresponds to the latency-associated peptide (LAP), and the 25-kD C-terminal portion of the precursor constitutes the mature TGF-β1. TGF-β activators can release TGF-β from LAP. These activators include proteases that degrade LAP, thrombospondin-1, reactive oxygen species, and integrins avb6 and avb8. Mouse TGF-β converts naïve T cells into regulatory T (Treg) cells that prevent autoimmunity. Although human TGF-β1 is widely used for inducing FOXP3+ in vitro, it might not be an essential factor for human Treg differentiation. Th17 murine can be induced from naïve CD4+ T cells by the combination of TGF-β1 and IL-6 or IL-21. Nevertheless, the regulation of human Th17 differentiation is distinct. TGF-β1 seems to have dual effects on human Th17 differentiation in a dose-dependent manner. While TGF-β1 is required for the expression of RORγt, in human naïve CD4+ T cells from cord blood, TGF-β1 can inhibit the function of RORγt at high doses. By using serum-free medium, it has been clarified that the optimum conditions for human Th17 differentiation are TGF-β1, IL-1β, and IL-2 in combination with IL-6, IL-21 or IL-23.

Any suitable TGF-β, or functional fragment, or modified version thereof, may be used in conjunction with the methods described herein (e.g., as a co-stimulant with IL-40; as a stimulant prior to IL-40 exposure). In some embodiments, TGF-β is a human TGF-β. An example human TGF-β nucleic acid sequence is provided herein as SEQ ID NO: 21 (full mRNA sequence provided as GENBANK Accession No. NM_000660.7), and an example human TGF-β amino acid sequence is provided herein as SEQ ID NO: 20 (GENBANK Accession No. NP_000651.3). Another example human TGF-β nucleic acid sequence is provided as GENBANK Accession No. BC000125.1, and another example human TGF-β amino acid sequence is provided GEN BANK Accession No. P01137. In some embodiments, TGF-β is a mouse TGF-β. An example mouse TGF-β nucleic acid sequence is provided herein as SEQ ID NO: 23 (full mRNA sequence provided as GEN BANK Accession No. NM_011577.2), and an example mouse TGF-β amino acid sequence is provided herein as SEQ ID NO: 22 (GENBANK Accession No. NP_035707).

TGF-β may refer to a precursor TGF-β polypeptide (includes the signal peptide) or a mature TGF-β polypeptide (excludes the signal peptide; or excludes the signal peptide and the latency-associated peptide). In some embodiments, TGF-β is a precursor TGF-β polypeptide (e.g., a precursor human TGF-β polypeptide comprising amino acids 1-390 of SEQ ID NO: 20; a precursor mouse TGF-β polypeptide comprising amino acids 1-390 of SEQ ID NO: 22). In some embodiments, a TGF-β polypeptide is a mature TGF-β polypeptide (e.g., a mature human TGF-β polypeptide comprising amino acids 30-390 of SEQ ID NO: 20; a mature human TGF-β polypeptide comprising amino acids 279-390 of SEQ ID NO: 20; a mature mouse TGF-β polypeptide comprising amino acids 29-390 of SEQ ID NO: 22; a mature mouse TGF-β polypeptide comprising amino acids 279-390 of SEQ ID NO: 22).

In some embodiments, TGF-β is a recombinant TGF-β polypeptide. A recombinant TGF-β polypeptide typically is a TGF-β polypeptide encoded by DNA (i.e., TGF-β nucleic acid sequence) that has been cloned in a vector or system that supports expression of the DNA and translation of messenger RNA. In some embodiments, TGF-β is a recombinant human TGF-β polypeptide (rhTGF-β). In some embodiments, TGF-β is a recombinant mouse TGF-β polypeptide (rmTGF-β). In some embodiments, TGF-β is a commercially available recombinant human TGF-β (e.g., BioLegend cat #580704; BioLegend cat #781802). In some embodiments, TGF-β is a commercially available recombinant mouse TGF-β (e.g., BioLegend cat #763102).

TGF-β may refer to an unmodified TGF-β polypeptide, a modified TGF-β polypeptide, a TGF-β variant, a TGF-β mutant; or a fragment thereof or a functional fragment thereof. Unmodified polypeptides, modified polypeptides, mutants, variants, and fragments are described herein. In some embodiments, TGF-β refers to a polypeptide comprising an amino acid sequence that is at least about 75% identical to SEQ ID NO: 20 or SEQ ID NO: 22. For example, TGF-β may refer to a polypeptide comprising an amino acid sequence that is at least about 75%, 80%, 85%, 90%, 91%, 92%, 93%, 94%, 95%, 96%, 97%, 98%, or 99% identical to SEQ ID NO: 20 or SEQ ID NO: 22.

In some embodiments, TGF-β refers to a fragment of a TGF-β polypeptide. Generally, a TGF-β fragment contains fewer amino acids than a full-length mature TGF-β. For example, a TGF-β fragment may include a portion of the mature human TGF-β polypeptide (e.g., a portion of amino acids 30-390 of SEQ ID NO: 20; a portion of amino acids 279-390 of SEQ ID NO: 20), or a portion of the mature mouse TGF-β polypeptide (e.g., a portion of amino acids 29-390 of SEQ ID NO: 22; a portion of amino acids 279-390 of SEQ ID NO: 22). An example full-length mature human TGF-β is 112 amino acids in length. Accordingly, fragments of human TGF-β may be 111 amino acids in length or shorter. An example full-length mature mouse TGF-β is 112 amino acids in length. Accordingly, fragments of mouse TGF-β may be 111 amino acids in length or shorter.

In some embodiments, TGF-β refers to a functional fragment of a TGF-β polypeptide. Any suitable method for assessing the activity of TGF-β and functional fragments of TGF-β may be used to determine whether a TGF-β fragment is a functional fragment. For example, one assay for assessing TGF-β activity is a cell proliferation inhibition assay. An example cell proliferation inhibition assay measures the extent to which TGF-β inhibits the proliferation of mouse HT-2 cells induced by recombinant mouse IL-4. In some embodiments, a functional fragment of TGF-β is a fragment that exhibits at least 50% of the activity of a TGF-β standard or a full-length mature TGF-β. For example, a functional fragment of TGF-β is a fragment that exhibits at least 50%, at least 60%, at least 70%, at least 80%, at least 90%, at least 95%, or more of the activity of a TGF-β standard or a full-length mature TGF-β.

GM-CSF

Certain methods provided herein include use of granulocyte-macrophage colony-stimulating factor (GM-CSF) as a stimulant or co-stimulant. Granulocyte-macrophage colony-stimulating factor (also referred to as GM-CSF, colony stimulating factor 2, CSF2, CSF-α, Pluripoietin-α, Eosinophil colony stimulating factor (Eo-CSF), burst promoting activity (BPA)) plays a role in signaling emergency hemopoiesis (predominantly myelopoiesis) in response to infection, including the production of granulocytes and macrophages in the bone marrow and their maintenance, survival, and functional activation at sites of injury or insult. The receptor for GM-CSF is a heterodimer that comprises a major binding subunit (GMRα) and a major signaling subunit (βc). The receptor subunits are coexpressed on the surface of leukocytes, with βc being expressed at lower levels than GMRα.

Certain nonhemopoietic cell types also have been reported to express the GM-CSF receptor and to respond to GM-CSF stimulation in vitro.

Any suitable GM-CSF, or functional fragment, or modified version thereof, may be used in conjunction with the methods described herein (e.g., as a co-stimulant with IL-40; as a stimulant prior to IL-40 exposure). In some embodiments, GM-CSF is a human GM-CSF. An example human GM-CSF nucleic acid sequence is provided herein as SEQ ID NO: 25 (full mRNA sequence provided as GENBANK Accession No. NM_000758), and an example human GM-CSF amino acid sequence is provided herein as SEQ ID NO: 24 (GENBANK Accession No. NP_000749.2). In some embodiments, GM-CSF is a mouse GM-CSF. An example mouse GM-CSF nucleic acid sequence is provided herein as SEQ ID NO: 27 (full mRNA sequence provided as GEN BANK Accession No. NM_009969), and an example mouse GM-CSF amino acid sequence is provided herein as SEQ ID NO: 26 (GENBANK Accession No. NP_034099.2).

GM-CSF may refer to a precursor GM-CSF polypeptide (includes the signal peptide) or a mature GM-CSF polypeptide (excludes the signal peptide). In some embodiments, GM-CSF is a precursor GM-CSF polypeptide (e.g., a precursor human GM-CSF polypeptide comprising amino acids 1-144 of SEQ ID NO: 24; a precursor mouse GM-CSF polypeptide comprising amino acids 1-141 of SEQ ID NO: 26). In some embodiments, a GM-CSF polypeptide is a mature GM-CSF polypeptide (e.g., a mature human GM-CSF polypeptide comprising amino acids 18-144 of SEQ ID NO: 24; a mature mouse GM-CSF polypeptide comprising amino acids 18-141 of SEQ ID NO: 26).

In some embodiments, GM-CSF is a recombinant GM-CSF polypeptide. A recombinant GM-CSF polypeptide typically is a GM-CSF polypeptide encoded by DNA (i.e., GM-CSF nucleic acid sequence) that has been cloned in a vector or system that supports expression of the DNA and translation of messenger RNA. In some embodiments, GM-CSF is a recombinant human GM-CSF polypeptide (rhGM-CSF). In some embodiments, GM-CSF is a recombinant mouse GM-CSF polypeptide (rmGM-CSF). In some embodiments, GM-CSF is a commercially available recombinant human GM-CSF (e.g., BioLegend cat #572902). In some embodiments, GM-CSF is a commercially available recombinant mouse GM-CSF (e.g., BioLegend cat #576302).

GM-CSF may refer to an unmodified GM-CSF polypeptide, a modified GM-CSF polypeptide, a GM-CSF variant, a GM-CSF mutant; or a fragment thereof or a functional fragment thereof. Unmodified polypeptides, modified polypeptides, mutants, variants, and fragments are described herein. In some embodiments, GM-CSF refers to a polypeptide comprising an amino acid sequence that is at least about 75% identical to SEQ ID NO: 24 or SEQ ID NO: 26. For example, GM-CSF may refer to a polypeptide comprising an amino acid sequence that is at least about 75%, 80%, 85%, 90%, 91%, 92%, 93%, 94%, 95%, 96%, 97%, 98%, or 99% identical to SEQ ID NO: 24 or SEQ ID NO: 26.

In some embodiments, GM-CSF refers to a fragment of a GM-CSF polypeptide. Generally, a GM-CSF fragment contains fewer amino acids than a full-length mature GM-CSF. For example, a GM-CSF fragment may include a portion of the mature human GM-CSF polypeptide (i.e., a portion of amino acids 18-144 of SEQ ID NO: 24), or a portion of the mature mouse GM-CSF polypeptide (i.e. a portion of amino acids 18-141 of SEQ ID NO: 26). An example full-length mature human GM-CSF is 127 amino acids in length. Accordingly, fragments of human GM-CSF may be 126 amino acids in length or shorter. An example full-length mature mouse GM-CSF is 124 amino acids in length. Accordingly, fragments of mouse GM-CSF may be 123 amino acids in length or shorter.

In some embodiments, GM-CSF refers to a functional fragment of a GM-CSF polypeptide. Any suitable method for assessing the activity of GM-CSF and functional fragments of GM-CSF may be used to determine whether a GM-CSF fragment is a functional fragment. For example, one assay for assessing GM-CSF activity is a cell proliferation assay. An example cell proliferation assay determines $EC_{50}$ of GM-CSF by dose-dependent stimulation of TF-1 cell proliferation. In some embodiments, a functional fragment of GM-CSF is a fragment that exhibits at least 50% of the activity of a GM-CSF standard (e.g., 1st WHO International Standard for Human GM-CSF (NIBSC code: 88/646)) or a full-length mature GM-CSF. For example, a functional fragment of GM-CSF is a fragment that exhibits at least 50%, at least 60%, at least 70%, at least 80%, at least 90%, at least 95%, or more of the activity of a GM-CSF standard or a full-length mature GM-CSF.

M-CSF

Certain methods provided herein include use of macrophage colony-stimulating factor (M-CSF) as a stimulant or co-stimulant. Macrophage colony-stimulating factor (also referred to as M-CSF, CSF1, CSF-1, MCSF) was first characterized as a glycoprotein that induces monocyte and macrophage colony formation from precursors in murine bone marrow cultures. M-CSF is constitutively present at biologically active concentrations in human serum. It binds CD14+ monocytes and promotes the survival/proliferation of human peripheral blood monocytes. In addition, M-CSF enhances inducible monocyte functions including phagocytic activity, microbial killing, cytotoxicity for tumor cells as well as synthesis of inflammatory cytokines such as IL-1, TNFα, and IFN-γ in monocytes. M-CSF induces RANKL production in mature human osteoclasts; consequently, M-CSF is a potent stimulator of mature osteoclast resorbing activity. Also, M-CSF induces VEGF in human monocytes in human tumors; high levels of M-CSF, mononuclear phagocytes, and VEGF are associated with poor prognosis in patients with cancer. High levels of M-CSF may be associated with different pathologies such as pulmonary fibrosis and atherosclerosis. M-CSF binds to its receptor M-CSFR, and this receptor is shared by a second ligand, IL-34. Human M-CSF and IL-34 exhibit cross-species specificity—both bind to human and mouse M-CSF receptors.

Any suitable M-CSF, or functional fragment, or modified version thereof, may be used in conjunction with the methods described herein (e.g., as a co-stimulant with IL-40; as a stimulant prior to IL-40 exposure). In some embodiments, M-CSF is a human M-CSF. An example human M-CSF nucleic acid sequence is provided herein as SEQ ID NO: 29 (full mRNA sequence provided as GENBANK Accession Nos. NM_172212.2 and NM_172212.3), and an example human M-CSF amino acid sequence is provided herein as SEQ ID NO: 28 (GENBANK Accession No. NP_757351.2). In some embodiments, M-CSF is a mouse M-CSF. An example mouse M-CSF nucleic acid sequence is provided herein as SEQ ID NO: 31 (full mRNA sequence provided as GENBANK Accession No. NM_001113530.1), and an example mouse M-CSF amino acid sequence is provided herein as SEQ ID NO: 30 (GENBANK Accession No. NP_001107002.1).

M-CSF may refer to a precursor M-CSF polypeptide (includes the signal peptide) or a mature M-CSF polypeptide (excludes the signal peptide). In some embodiments, M-CSF is a precursor M-CSF polypeptide (e.g., a precursor human M-CSF polypeptide comprising amino acids 1-190 of SEQ ID NO: 28; a precursor human M-CSF polypeptide comprising amino acids 1-450 of SEQ ID NO: 28; a precursor human M-CSF polypeptide comprising amino acids 1-554 of SEQ ID NO: 28; a precursor mouse M-CSF polypeptide comprising amino acids 1-262 of SEQ ID NO: 30; a precursor mouse M-CSF polypeptide comprising amino acids 1-552 of SEQ ID NO: 30). In some embodiments, a M-CSF polypeptide is a mature M-CSF polypeptide (e.g., a mature human M-CSF polypeptide comprising amino acids 33-190 of SEQ ID NO: 28; a mature human M-CSF polypeptide comprising amino acids 33-450 of SEQ ID NO: 28; a mature human M-CSF polypeptide comprising amino acids 33-554 of SEQ ID NO: 28; a mature mouse M-CSF polypeptide comprising amino acids 33-262 of SEQ ID NO: 30; a mature mouse M-CSF polypeptide comprising amino acids 33-552 of SEQ ID NO: 30).

In some embodiments, M-CSF is a recombinant M-CSF polypeptide. A recombinant M-CSF polypeptide typically is an M-CSF polypeptide encoded by DNA (i.e., M-CSF nucleic acid sequence) that has been cloned in a vector or system that supports expression of the DNA and translation of messenger RNA. In some embodiments, M-CSF is a recombinant human M-CSF polypeptide (rhM-CSF). In some embodiments, M-CSF is a recombinant mouse M-CSF polypeptide (rmM-CSF). In some embodiments, M-CSF is a commercially available recombinant human M-CSF (e.g., BioLegend cat #574802). In some embodiments, M-CSF is a commercially available recombinant mouse M-CSF (e.g., BioLegend cat #576402).

M-CSF may refer to an unmodified M-CSF polypeptide, a modified M-CSF polypeptide, an M-CSF variant, an M-CSF mutant; or a fragment thereof or a functional fragment thereof. Unmodified polypeptides, modified polypeptides, mutants, variants, and fragments are described herein. In some embodiments, M-CSF refers to a polypeptide comprising an amino acid sequence that is at least about 75% identical to SEQ ID NO: 28 or SEQ ID NO: 30. For example, M-CSF may refer to a polypeptide comprising an amino acid sequence that is at least about 75%, 80%, 85%, 90%, 91%, 92%, 93%, 94%, 95%, 96%, 97%, 98%, or 99% identical to SEQ ID NO: 28 or SEQ ID NO: 30.

In some embodiments, M-CSF refers to a fragment of an M-CSF polypeptide. Generally, an M-CSF fragment contains fewer amino acids than a full-length mature M-CSF. For example, an M-CSF fragment may include a portion of the mature human M-CSF polypeptide (e.g., a portion of amino acids 33-190 of SEQ ID NO: 28; a portion of amino acids 33-450 of SEQ ID NO: 28; a portion of amino acids 33-554 of SEQ ID NO: 28), or a portion of the mature mouse M-CSF polypeptide (e.g., a portion of amino acids 33-262 of SEQ ID NO: 30; a portion of amino acids 33-552 of SEQ ID NO: 30). An example full-length mature human M-CSF is 158 amino acids in length. Accordingly, fragments of human M-CSF may be 157 amino acids in length or shorter. An example full-length mature mouse M-CSF is 230 amino acids in length. Accordingly, fragments of mouse M-CSF may be 229 amino acids in length or shorter.

In some embodiments, M-CSF refers to a functional fragment of an M-CSF polypeptide. Any suitable method for assessing the activity of M-CSF and functional fragments of M-CSF may be used to determine whether an M-CSF fragment is a functional fragment. For example, one assay for assessing M-CSF activity is a cell proliferation assay. An example cell proliferation assay determines $EC_{50}$ of M-CSF by dose-dependent stimulation of M-NFS60 cell proliferation. In some embodiments, a functional fragment of M-CSF is a fragment that exhibits at least 50% of the activity of an M-CSF standard or a full-length mature M-CSF. For example, a functional fragment of M-CSF is a fragment that exhibits at least 50%, at least 60%, at least 70%, at least 80%, at least 90%, at least 95%, or more of the activity of an M-CSF standard or a full-length mature M-CSF.

IFN-α

Certain methods provided herein include use of interferon alpha (IFN-α) as a stimulant or co-stimulant. Interferon alpha also may be referred to as IFN-α, IFN-α2, IFN-alpha 2B, IFN-alphaA, IFNA2, or IFNA2B. Interferons are divided into type I, II, and III. Type I IFNs (IFN-α and IFN-β) are most abundant in number, distribution, and expression. Also, they are highly conserved among mammals in both structure and function. IFN-α2 has been used in the treatment of cancer such as bladder cancer, hepato-cellular carcinoma, and leukemia. IFN-α2 augments the suppressed immune functions in patients with head and neck squamous cell carcinoma (HNSCC). IFN-α2 initiated T and NK cell mediated cytotoxicity of tumor cells through IFNγ dependent and independent mechanisms. IFN-α2 enhances suppressed T cell cytotoxicity by stimulation of the perforin-granzyme B system (IFNγ dependent). Also, IFN-α2 induces the expression of perforin-granzyme B in NK cells (NK mediated cytotoxicity, IFNγ independent). IFN-α2 may be an immunostimulator and may impact the clinical outcome in tongue squamous cell carcinoma patients. IFN-α had been used in the treatment of chronic hepatitis C (CHC); nevertheless, IFN-α is relatively unstable and requires frequent parenteral administration. Pegylation of IFN-α, polyethylene glycol (PEG)-IFN-α, reduces in vitro activity but increase the stability and plasma half-life of IFN-α; therefore, PEG-IFN-α has replaced IFN-α in CHC treatment.

Any suitable IFN-α, or functional fragment, or modified version thereof, may be used in conjunction with the methods described herein (e.g., as a co-stimulant with IL-40; as a stimulant prior to IL-40 exposure). In some embodiments, IFN-α is a human IFN-α. An example human IFN-α nucleic acid sequence is provided herein as SEQ ID NO: 33 (full mRNA sequence provided as GEN BANK Accession No. NM_000605), and an example human IFN-α amino acid sequence is provided herein as SEQ ID NO: 32 (GENBANK Accession No. NP_000596.2). In some embodiments, IFN-α is a mouse IFN-α. An example mouse IFN-α nucleic acid sequence is provided herein as SEQ ID NO: 35 (full mRNA sequence provided as GENBANK Accession No. NM_206870), and an example mouse IFN-α amino acid sequence is provided herein as SEQ ID NO: 34 (GENBANK Accession No. NP_996753.1).

IFN-α may refer to a precursor IFN-α polypeptide (includes the signal peptide) or a mature IFN-α polypeptide (excludes the signal peptide). In some embodiments, IFN-α is a precursor IFN-α polypeptide (e.g., a precursor human IFN-α polypeptide comprising amino acids 1-188 of SEQ ID NO: 32; a precursor mouse IFN-α polypeptide comprising amino acids 1-190 of SEQ ID NO: 34). In some embodiments, an IFN-α polypeptide is a mature IFN-α polypeptide (e.g., a mature human IFN-α polypeptide comprising amino acids 24-188 of SEQ ID NO: 32; a mature mouse IFN-α polypeptide comprising amino acids 24-190 of SEQ ID NO: 34).

In some embodiments, IFN-α is a recombinant IFN-α polypeptide. A recombinant IFN-α polypeptide typically is an IFN-α polypeptide encoded by DNA (i.e., IFN-α nucleic acid sequence) that has been cloned in a vector or system that supports expression of the DNA and translation of messenger RNA. In some embodiments, IFN-α is a recombinant human IFN-α polypeptide (rhIFN-α). In some embodiments, IFN-α is a recombinant mouse IFN-α polypeptide (rmIFN-α). In some embodiments, IFN-α is a commercially available recombinant human IFN-α (e.g., BioLegend cat #592702). In some embodiments, IFN-α is a commercially available recombinant mouse IFN-α (e.g., BioLegend cat #752802).

IFN-α may refer to an unmodified IFN-α polypeptide, a modified IFN-α polypeptide, an IFN-α variant, an IFN-α mutant; or a fragment thereof or a functional fragment thereof. Unmodified polypeptides, modified polypeptides, mutants, variants, and fragments are described herein. In some embodiments, IFN-α refers to a polypeptide comprising an amino acid sequence that is at least about 75% identical to SEQ ID NO: 32 or SEQ ID NO: 34. For example, IFN-α may refer to a polypeptide comprising an amino acid sequence that is at least about 75%, 80%, 85%, 90%, 91%, 92%, 93%, 94%, 95%, 96%, 97%, 98%, or 99% identical to SEQ ID NO: 32 or SEQ ID NO: 34.

In some embodiments, IFN-α refers to a fragment of an IFN-α polypeptide. Generally, an IFN-α fragment contains fewer amino acids than a full-length mature IFN-α. For example, an IFN-α fragment may include a portion of the mature human IFN-α polypeptide (e.g., a portion of amino acids 24-188 of SEQ ID NO: 32), or a portion of the mature mouse IFN-α polypeptide (e.g., a portion of amino acids 24-190 of SEQ ID NO: 34). An example full-length mature human IFN-α is 165 amino acids in length. Accordingly, fragments of human IFN-α may be 164 amino acids in length or shorter. An example full-length mature mouse IFN-α is 167 amino acids in length. Accordingly, fragments of mouse IFN-α may be 166 amino acids in length or shorter.

In some embodiments, IFN-α refers to a functional fragment of an IFN-α polypeptide. Any suitable method for assessing the activity of IFN-α and functional fragments of IFN-α may be used to determine whether an IFN-α fragment is a functional fragment. For example, one assay for assessing IFN-α activity is a cytopathic effect inhibition assay. For example, specific activity of IFN-α may be determined in a cytopathic effect inhibition assay using the EMC virus on L929 or A549 cells. In some embodiments, a functional fragment of IFN-α is a fragment that exhibits at least 50% of the activity of an IFN-α standard or a full-length mature IFN-α. For example, a functional fragment of IFN-α is a fragment that exhibits at least 50%, at least 60%, at least 70%, at least 80%, at least 90%, at least 95%, or more of the activity of an IFN-α standard or a full-length mature IFN-α.

IL-1β

Certain methods provided herein include use of interleukin 1 beta (IL-1β) as a stimulant or co-stimulant. Interleukin 1 beta also may be referred to as IL-1β, catabolin, preinterleukin 1 beta, or pro-interleukin-1-beta. IL-1β in humans and mice does not encode a typical signal peptide and, as a result, newly synthesized pro-IL-1β accumulates within the cytoplasm of activated monocytes and macrophages. Conversion of the inactive pro-IL-1β to its mature form requires the proteolytic action of IL-1β-converting enzyme (ICE), also termed caspase-1. Secretion of mature IL-1β from LPS-activated monocytes/macrophages is not a constitutive process. These cells encounter a secondary stimulus that specifically activates the posttranslational processing events. Moreover, owing to its pro-inflammatory nature, IL-1β is regarded as a tumor-promoting cytokine. Enhanced tumor metastasis and angiogenesis has been observed under the influence of IL-1β. IL-1β is able to facilitate tumor progression in murine models of lung cancer. In addition, upregulation of metastasis and tumor angiogenesis by IL-1β has been associated with increased activity of matrix metalloproteinases and expression of the pro-angiogenic molecule hepatocyte growth factor.

Any suitable IL-1β, or functional fragment, or modified version thereof, may be used in conjunction with the methods described herein (e.g., as a co-stimulant with IL-40; as a stimulant prior to IL-40 exposure). In some embodiments, IL-1β is a human IL-1β. An example human IL-1β nucleic acid sequence is provided herein as SEQ ID NO: 37 (full mRNA sequence provided as GENBANK Accession No. NM_000576), and an example human IL-1β amino acid sequence is provided herein as SEQ ID NO: 36 (GENBANK Accession No. NP_000567.1). In some embodiments, IL-1β is a mouse IL-1β. An example mouse IL-1β nucleic acid sequence is provided herein as SEQ ID NO: 39 (full mRNA sequence provided as GENBANK Accession No. NM_008361), and an example mouse IL-1β amino acid sequence is provided herein as SEQ ID NO: 38 (GENBANK Accession No. NP_032387.1).

IL-1β may refer to a precursor IL-1β polypeptide (includes the propeptide) or a mature IL-1β polypeptide (excludes the propeptide). In some embodiments, IL-1β is a precursor IL-1β polypeptide (e.g., a precursor human IL-1β polypeptide comprising amino acids 1-269 of SEQ ID NO: 36; a precursor mouse IL-1β polypeptide comprising amino acids 1-269 of SEQ ID NO: 38). In some embodiments, an IL-1β polypeptide is a mature IL-1β polypeptide (e.g., a mature human IL-1β polypeptide comprising amino acids 117-269 of SEQ ID NO: 36; a mature mouse IL-1β polypeptide comprising amino acids 118-269 of SEQ ID NO: 38).

In some embodiments, IL-1β is a recombinant IL-1β polypeptide. A recombinant IL-1β polypeptide typically is an IL-1β polypeptide encoded by DNA (i.e., IL-1β nucleic acid sequence) that has been cloned in a vector or system that supports expression of the DNA and translation of messenger RNA. In some embodiments, IL-1β is a recombinant human IL-1β polypeptide (rhIL-1β). In some embodiments, IL-1β is a recombinant mouse IL-1β polypeptide (rmIL-1β). In some embodiments, IL-1β is a commercially available recombinant human IL-1β (e.g., BioLegend cat #579402). In some embodiments, IL-1β is a commercially available recombinant mouse IL-1β (e.g., BioLegend cat #575102).

IL-1β may refer to an unmodified IL-1β polypeptide, a modified IL-1β polypeptide, an IL-1β variant, an IL-1β mutant; or a fragment thereof or a functional fragment thereof. Unmodified polypeptides, modified polypeptides, mutants, variants, and fragments are described herein. In some embodiments, IL-1β refers to a polypeptide comprising an amino acid sequence that is at least about 75% identical to SEQ ID NO: 36 or SEQ ID NO: 38. For example, IL-1β may refer to a polypeptide comprising an amino acid sequence that is at least about 75%, 80%, 85%, 90%, 91%, 92%, 93%, 94%, 95%, 96%, 97%, 98%, or 99% identical to SEQ ID NO: 36 or SEQ ID NO: 38.

In some embodiments, IL-1β refers to a fragment of an IL-1β polypeptide. Generally, an IL-1β fragment contains fewer amino acids than a full-length mature IL-1β. For example, an IL-1β fragment may include a portion of the mature human IL-1β polypeptide (e.g., a portion of amino acids 117-269 of SEQ ID NO: 36), or a portion of the mature mouse IL-1β polypeptide (e.g., a portion of amino acids 118-269 of SEQ ID NO: 38). An example full-length mature human IL-1β is 153 amino acids in length. Accordingly, fragments of human IL-1β may be 152 amino acids in length or shorter. An example full-length mature mouse IL-1β is 152 amino acids in length. Accordingly, fragments of mouse IL-1β may be 151 amino acids in length or shorter.

In some embodiments, IL-1β refers to a functional fragment of an IL-1β polypeptide. Any suitable method for assessing the activity of IL-1β and functional fragments of IL-1β may be used to determine whether an IL-1β fragment is a functional fragment. For example, one assay for assessing IL-1β activity is a cell proliferation assay. For example, the $ED_{50}$ of IL-1β may be determined by dose dependent stimulation of D10.G4.1 cell proliferation. In some embodiments, a functional fragment of IL-1β is a fragment that exhibits at least 50% of the activity of an IL-1β standard or a full-length mature IL-1β. For example, a functional fragment of IL-1β is a fragment that exhibits at least 50%, at least 60%, at least 70%, at least 80%, at least 90%, at least 95%, or more of the activity of an IL-1β standard or a full-length mature IL-1β.

IL-13

Certain methods provided herein include use of inter-leukin 13 (IL-13) as a stimulant or co-stimulant. Interleukin 13 also may be referred to as IL-13, ALRH, BHR1, P600, IL-13, MGC116786, MGC116788, MGC116789, NC30, or IL13. Human IL-13 was initially cloned from cDNA librar-ies of activated T cells. IL-13 is an immunoregulatory cytokine secreted predominantly by activated T(H)2 cells, and it is a mediator in the pathogenesis of allergic inflam-mation. IL-13 shares many functional properties with IL-4, and they share a common receptor subunit, the alpha subunit of the IL-4 receptor (IL-4Ralpha). IL-13 mediates its effects by interacting with a complex receptor system comprised of IL-4Ralpha and two IL-13 binding proteins, IL-13Ralpha1 and IL-13Ralpha2. Ligation of the IL-13 receptor complex results in signaling via the insulin receptor substrate (IRS)-1 and 2 and STAT-6 pathways. IL-13, like IL-4, is a cytokine produced by T(H)2 type helper T cells in response to signaling through the T cell antigen receptor and by mast cells and basophils upon cross-linkage of the high-affinity receptor for immunoglobulin E (IgE). IL-13 has been impli-cated in airway hypersensitivity and mucus hypersecretion, inflammatory bowel disease, and parasitic nematode expul-sion.

Any suitable IL-13, or functional fragment, or modified version thereof, may be used in conjunction with the meth-ods described herein (e.g., as a co-stimulant with IL-40; as a stimulant prior to IL-40 exposure). In some embodiments, IL-13 is a human IL-13. An example human IL-13 nucleic acid sequence is provided herein as SEQ ID NO: 41 (full mRNA sequence provided as GENBANK Accession No. X69079), and an example human IL-13 amino acid sequence is provided herein as SEQ ID NO: 40 (GENBANK Accession No. CAA48823.1 or P35225.2). Another example human IL-13 amino acid sequence is provided as GEN-BANK Accession No. NP_002179.2. In some embodiments, IL-13 is a mouse IL-13. An example mouse IL-13 nucleic acid sequence is provided herein as SEQ ID NO: 43 (full mRNA sequence provided as GENBANK Accession No. NM_008355), and an example mouse IL-13 amino acid sequence is provided herein as SEQ ID NO: 42 (GENBANK Accession No. NP_032381.1).

IL-13 may refer to a precursor IL-13 polypeptide (in-cludes the signal peptide) or a mature IL-13 polypeptide (excludes the signal peptide). In some embodiments, IL-13 is a precursor IL-13 polypeptide (e.g., a precursor human IL-13 polypeptide comprising amino acids 1-132 of SEQ ID NO: 40; a precursor human IL-13 polypeptide comprising amino acids 1-146 of SEQ ID NO: 40; a precursor mouse IL-13 polypeptide comprising amino acids 1-131 of SEQ ID NO: 42). In some embodiments, an IL-13 polypeptide is a mature IL-13 polypeptide (e.g., a mature human IL-13 polypeptide comprising amino acids 21-132 of SEQ ID NO: 40; a mature mouse IL-13 polypeptide comprising amino acids 26-131 of SEQ ID NO: 42).

In some embodiments, IL-13 is a recombinant IL-13 polypeptide. A recombinant IL-13 polypeptide typically is an IL-13 polypeptide encoded by DNA (i.e., IL-13 nucleic acid sequence) that has been cloned in a vector or system that supports expression of the DNA and translation of messenger RNA. In some embodiments, IL-13 is a recom-binant human IL-13 polypeptide (rhIL-13). In some embodi-ments, IL-13 is a recombinant mouse IL-13 polypeptide (rmIL-13). In some embodiments, IL-13 is a commercially available recombinant human IL-13 (e.g., BioLegend cat #571102). In some embodiments, IL-13 is a commercially available recombinant mouse IL-13 (e.g., BioLegend cat #575902).

IL-13 may refer to an unmodified IL-13 polypeptide, a modified IL-13 polypeptide, an IL-13 variant, an IL-13 mutant; or a fragment thereof or a functional fragment thereof. Unmodified polypeptides, modified polypeptides, mutants, variants, and fragments are described herein. In some embodiments, IL-13 refers to a polypeptide compris-ing an amino acid sequence that is at least about 75% identical to SEQ ID NO: 40 or SEQ ID NO: 42. For example, IL-13 may refer to a polypeptide comprising an amino acid sequence that is at least about 75%, 80%, 85%, 90%, 91%, 92%, 93%, 94%, 95%, 96%, 97%, 98%, or 99% identical to SEQ ID NO: 40 or SEQ ID NO: 42.

In some embodiments, IL-13 refers to a fragment of an IL-13 polypeptide. Generally, an IL-13 fragment contains fewer amino acids than a full-length mature IL-13. For example, an IL-13 fragment may include a portion of the mature human IL-13 polypeptide (e.g., a portion of amino acids 21-132 of SEQ ID NO: 40), or a portion of the mature mouse IL-13 polypeptide (e.g., a portion of amino acids 26-131 of SEQ ID NO: 42). An example full-length mature human IL-13 is 112 amino acids in length. Accordingly, fragments of human IL-13 may be 111 amino acids in length or shorter. An example full-length mature mouse IL-13 is 106 amino acids in length. Accordingly, fragments of mouse IL-13 may be 105 amino acids in length or shorter.

In some embodiments, IL-13 refers to a functional frag-ment of an IL-13 polypeptide. Any suitable method for assessing the activity of IL-13 and functional fragments of IL-13 may be used to determine whether an IL-13 fragment is a functional fragment. For example, one assay for assess-ing IL-13 activity is a cell proliferation assay. For example, the $ED_{50}$ of IL-13 may be determined by dose dependent stimulation of TF-1 cell proliferation. In some embodiments, a functional fragment of IL-13 is a fragment that exhibits at least 50% of the activity of an IL-13 standard or a full-length mature IL-13. For example, a functional fragment of IL-13 is a fragment that exhibits at least 50%, at least 60%, at least 70%, at least 80%, at least 90%, at least 95%, or more of the activity of an IL-13 standard or a full-length mature IL-13.

TNF-α

Certain methods provided herein include use of tumor necrosis factor alpha (TNF-α) as a stimulant or co-stimulant. Tumor necrosis factor alpha (TNF-α) also may be referred to as cachectin, necrosin, macrophage cytotoxic factor (MCF), differentiation inducing factor (DIF), or TNFSF2. TNF-α is released from macrophages, monocytes, neutro-phils, T-cells (principally CD4+), NK-cells and many trans-formed cell lines. Soluble homotrimeric TNF-α is released from cells by proteolysis of the integral membrane precursor form of TNF-α. TNF-α binding to some TNF-α receptors induces apoptosis and depending on cell type, receptor expression, and signal transduction status can induce other responses. TNF-α is involved in the inflammatory response.

Any suitable TNF-α, or functional fragment, or modified version thereof, may be used in conjunction with the meth-ods described herein (e.g., as a co-stimulant with IL-40; as a stimulant prior to IL-40 exposure). In some embodiments, TNF-α is a human TNF-α. An example human TNF-α nucleic acid sequence is provided herein as SEQ ID NO: 45 (full mRNA sequence provided as GENBANK Accession No. NM_000594), and an example human TNF-α amino acid sequence is provided herein as SEQ ID NO: 44 (GEN- BANK Accession No. NP_000585.2). In some embodiments, TNF-α is a mouse TNF-α. An example mouse TNF-α nucleic acid sequence is provided herein as SEQ ID NO: 47 (full mRNA sequence provided as GENBANK Accession No. NM_013693), and an example mouse TNF-α amino acid sequence is provided herein as SEQ ID NO: 46 (GENBANK Accession No. NP_038721.1).

TNF-α may refer to a precursor TNF-α polypeptide (integral membrane precursor form) or a mature TNF-α polypeptide (soluble homotrimeric form). In some embodiments, TNF-α is a precursor TNF-α polypeptide (e.g., a precursor human TNF-α polypeptide comprising amino acids 1-233 of SEQ ID NO: 44; a precursor mouse TNF-α polypeptide comprising amino acids 1-235 of SEQ ID NO: 46). In some embodiments, a TNF-α polypeptide is a mature TNF-α polypeptide (e.g., a mature human TNF-α polypeptide comprising amino acids 77-233 of SEQ ID NO: 44; a mature mouse TNF-α polypeptide comprising amino acids 80-235 of SEQ ID NO: 46).

In some embodiments, TNF-α is a recombinant TNF-α polypeptide. A recombinant TNF-α polypeptide typically is a TNF-α polypeptide encoded by DNA (i.e., TNF-α nucleic acid sequence) that has been cloned in a vector or system that supports expression of the DNA and translation of messenger RNA. In some embodiments, TNF-α is a recombinant human TNF-α polypeptide (rhTNF-α). In some embodiments, TNF-α is a recombinant mouse TNF-α polypeptide (rmTNF-α). In some embodiments, TNF-α is a commercially available recombinant human TNF-α (e.g., BioLegend cat #570102). In some embodiments, TNF-α is a commercially available recombinant mouse TNF-α (e.g., BioLegend cat #575202).

TNF-α may refer to an unmodified TNF-α polypeptide, a modified TNF-α polypeptide, a TNF-α variant, a TNF-α mutant; or a fragment thereof or a functional fragment thereof. Unmodified polypeptides, modified polypeptides, mutants, variants, and fragments are described herein. In some embodiments, TNF-α refers to a polypeptide comprising an amino acid sequence that is at least about 75% identical to SEQ ID NO: 44 or SEQ ID NO: 46. For example, TNF-α may refer to a polypeptide comprising an amino acid sequence that is at least about 75%, 80%, 85%, 90%, 91%, 92%, 93%, 94%, 95%, 96%, 97%, 98%, or 99% identical to SEQ ID NO: 44 or SEQ ID NO: 46.

In some embodiments, TNF-α refers to a fragment of a TNF-α polypeptide. Generally, a TNF-α fragment contains fewer amino acids than a full-length mature TNF-α. For example, a TNF-α fragment may include a portion of the mature human TNF-α polypeptide (e.g., a portion of amino acids 77-233 of SEQ ID NO: 44), or a portion of the mature mouse TNF-α polypeptide (e.g., a portion of amino acids 80-235 of SEQ ID NO: 46). An example full-length mature human TNF-α is 157 amino acids in length. Accordingly, fragments of human TNF-α may be 156 amino acids in length or shorter. An example full-length mature mouse TNF-α is 156 amino acids in length. Accordingly, fragments of mouse TNF-α may be 155 amino acids in length or shorter.

In some embodiments, TNF-α refers to a functional fragment of a TNF-α polypeptide. Any suitable method for assessing the activity of TNF-α and functional fragments of TNF-α may be used to determine whether a TNF-α fragment is a functional fragment. For example, one assay for assessing TNF-α activity is a cytotoxicity assay. For example, the $ED_{50}$ of TNF-α may be determined by dose-dependent cytotoxicity of L929 cells stimulated with actinomycin D. In some embodiments, a functional fragment of TNF-α is a fragment that exhibits at least 50% of the activity of a TNF-α standard (e.g., 3rd WHO International Standard for Human TNF-α (NIBSC code: 12/154)) or a full-length mature TNF-α. For example, a functional fragment of TNF-α is a fragment that exhibits at least 50%, at least 60%, at least 70%, at least 80%, at least 90%, at least 95%, or more of the activity of a TNF-α standard or a full-length mature TNF-α.

Cells

Certain methods described herein include stimulating a cell or population of cells (e.g., with IL-40; with a stimulant; with IL-40+a co-stimulant). Cells may be obtained from a subject and/or a cellular source, or may be obtained as an established cell line. A cellular source may include a population of embryonic stem (ES) cells, induced pluripotent stem cells (iPSCs), and the like. Cells may be isolated from an embryo or a stem cell culture derived from an embryo. Cells may be isolated from an induced pluripotent stem cell (iPSC) culture. Cells may be obtained from a subject in a variety of manners (e.g., harvested from living tissue, such as a biopsy, plucked hair follicles, body fluids like urine or body-cavity fluids, or isolated from circulation). A subject may include any animal, including but not limited to any mammal, such as mouse, rat, canine, feline, bovine, equine, porcine, non-human primate and human. In certain embodiments, a subject is a human. In some embodiments, a subject is an animal or human that has gestated longer than an embryo in a uterine environment and often is a post-natal human or a post-natal animal (e.g., neonatal human, neonatal animal, adult human or adult animal). A subject sometimes is a juvenile animal, juvenile human, adult animal or adult human.

In some embodiments, cells are isolated from a sample from a subject. An isolated cell refers to a cell that has been separated from a component of its original environment (e.g., separated from a host and/or purified from a sample), and thus is altered by human intervention (e.g., "by the hand of man") from its original environment. A sample can include any specimen that is isolated or obtained from a subject or part thereof. Non-limiting examples of specimens include fluid or tissue from a subject, including, without limitation, blood or a blood product (e.g., serum, plasma, or the like), umbilical cord blood, bone marrow, chorionic villi, amniotic fluid, cerebrospinal fluid, spinal fluid, lavage fluid (e.g., bronchoalveolar, gastric, peritoneal, ductal, ear, arthroscopic), biopsy sample or tissue biopsy, buccal swab, celocentesis sample, washings of female reproductive tract, urine, feces, sputum, saliva, nasal mucous, prostate fluid, lavage, semen, lymphatic fluid, bile, tears, sweat, breast milk, breast fluid, hard tissues (e.g., liver, spleen, kidney, lung, or ovary), the like or combinations thereof. The term blood encompasses whole blood, blood product or any fraction of blood, such as serum, plasma, buffy coat, or the like as conventionally defined. Blood plasma refers to the fraction of whole blood resulting from centrifugation of blood treated with anticoagulants. Blood serum refers to the watery portion of fluid remaining after a blood sample has coagulated.

In some embodiments, cells comprise normal, healthy cells (e.g., cells that are not diseased). In some embodiments, cells comprise cells that are genetically altered. In some embodiments, cells comprise cells that are not genetically altered. In some embodiments, cells comprise diseased cells. Diseased cells may include cells from a subject carrying disease-causing mutation(s). Diseased cells may include cells from abnormal tissue, such as from a neoplasia, a hyperplasia, a malignant tumor or a benign tumor. In certain embodiments, diseased cells include cells that are not tumor cells. In certain embodiments, diseased cells may include cells isolated from circulation (e.g., circulating tumor cells (CTCs)) of a subject. In certain embodiments, diseased cells may include cells isolated from bodily samples such as, for example, urine, semen, stool (feces), and the like.

In some embodiments, cells comprise primary cells. Primary cells generally are taken directly from living tissue, such as a biopsy, plucked hair follicles, bodily samples such as a stool sample, body fluids like urine, semen or body-cavity fluids, or isolated from circulation. In certain instances, primary cells have not been passaged. In certain instances, primary cells have been passaged one time. Primary cells may be isolated from differentiated tissue. Typically, primary cells have been freshly isolated, for example, through tissue digestion and plated. Primary cells may or may not be frozen and then thawed at a later time. In addition, the tissue from which the primary cells are isolated may or may not have been frozen or preserved in some other manner immediately prior to processing. Typically, cells are no longer primary cells after the cells have been passaged more than once. Cells passaged once or more and immediately frozen after passaging are also not considered as primary cells when thawed. In certain embodiments, cells are initially primary cells and become non-primary cells after passaging. In some embodiments, cells are maintained or proliferated in cell culture after the cells are isolated from differentiated tissue and prior to use in methods described herein.

In some embodiments, cells comprise non-primary cells, such as cells from an established cell line, transformed cells, thawed cells from a previously frozen collection, and the like. Any suitable cell line may be used in conjunction with the methods described herein. Examples of established cell lines include, for example, THP-1 (acute myeloid leukemia), DU145 (prostate cancer), H295R (adrenocortical cancer), HeLa (cervical cancer), KBM-7 (chronic myelogenous leukemia), LNCaP (prostate cancer), MCF-7 (breast cancer), MDA-MB-468 (breast cancer), PC3 (prostate cancer), SaOS-2 (bone cancer), SH-SY5Y (neuroblastoma, cloned from a myeloma), T-47D (breast cancer), U87 (glioblastoma), Vero (African green monkey Chlorocebus kidney epithelial cell line), MC3T3 (embryonic calvarium), GH3 (pituitary tumor), PC12 (pheochromocytoma), CHO (Chinese hamster ovary), MDCK (kidney epithelial), A6 (kidney epithelial), and AB9. In some embodiments, cells comprise THP-1 cells.

In some embodiments, cells comprise immune cells. Immune cells may include, for example, lymphocytes, leukocytes, agranulocytes, monocytes, macrophages, B cells, dendritic cells, granulocytes, neutrophils, innate lymphoid cells (ILC), megakaryocytes, myeloid-derived suppressor cells (MDSC), natural killer cells (NK cells), platelets, red blood cells (RBC), T cells, mast cells, eosinophils, basophils, and thymocytes. In some embodiments, cells comprise, or are derived from, peripheral blood mononuclear cells (PBMCs) which may include, for example, T cells, B cells, natural killer cells, and monocytes.

In some embodiments, cells comprise monocytes. Monocytes are a type of leukocyte, or white blood cell, and can differentiate into macrophages and myeloid lineage dendritic cells. Monocytes are a part of the vertebrate innate immune system and can influence the process of adaptive immunity. There are at least three subclasses of monocytes in human blood, which may be characterized according to certain markers. For example, the classical monocyte is characterized by high level expression of the CD14 cell surface receptor (CD14++ CD16– monocyte); the non-classical monocyte shows low level expression of CD14 and additional co-expression of the CD16 receptor (CD14+ CD16++ monocyte); and the intermediate monocyte is characterized by high level expression of CD14 and low level expression of CD16 (CD14++CD16+ monocytes).

In some embodiments, cells comprise macrophages. Macrophages are a type of white blood cell that engulf and digest foreign proteins and other substances, cellular debris, microbes, and cancer cells. Macrophages may be referred to as phagocytes, histiocytes, Kupffer cells, alveolar macrophages, or microglia, and may be found in nearly all body tissues. Macrophages are involved in nonspecific defense (innate immunity) and can help initiate specific defense mechanisms (adaptive immunity) by recruiting other immune cells such as lymphocytes. Macrophages also have an anti-inflammatory role and can decrease immune reactions through the release of cytokines. Macrophages that encourage inflammation are often referred to as M1 macrophages, and macrophages that decrease inflammation and encourage tissue repair are often referred to as M2 macrophages. Macrophages are produced by the differentiation of monocytes. Macrophages may be identified by their specific expression of proteins such as CD14, CD40, CD11b, CD64, F4/80, EMR1, lysozyme M, MAC-1/MAC-3 and CD68 using flow cytometry and/or immunohistochemical staining. Dysfunctional macrophages may cause diseases such as chronic granulomatous disease that results in frequent infections.

In some embodiments, cells comprise non-immune cells. Non-immune cells may include, for example, epithelial cells (e.g., cells lining body cavities), cells derived from the central nervous system (e.g., nerve cells, neurons, neuroglial cells), stromal cells (e.g., connective tissue cells, fibroblasts, pericytes), stem cells (e.g., embryonic stem cells, adult stem cells), muscle cells (e.g., skeletal, cardiac, smooth), cartilage cells (e.g., chondrocytes), bone cells (e.g., osteoblasts, osteoclasts, osteocytes, lining cells), skin cells (e.g., keratinocytes, melanocytes, merkel cells, langerhans cells), endothelial cells (e.g., cells lining blood vessels), fat cells (e.g., white adipocytes, brown adipocytes), and sex cells (spermatozoa, ova).

In some embodiments, cells comprise epithelial cells. An epithelial cell, or epithelium, typically refers to a cell or cells that line hollow organs, as well as those that make up glands and the outer surface of the body. Epithelial cells can comprise squamous epithelial cells, columnar epithelial cells, adenomatous epithelial cells or transitional epithelial cells. Epithelial cells can be arranged in single layers or can be arranged in multiple layers, depending on the organ and location, and may comprise keratinocyte (KE) epithelial cells or non-keratinocyte (NKE) epithelial cells.

Keratinocytes form the squamous epithelium that is found at anatomic sites such as the skin, ocular surface, oral mucosa, esophagus and cervix. Keratinocytes terminally differentiate into flat, highly keratinized, non-viable cells that help protect against the environment and infection by forming a protective barrier. Examples of keratinocyte epithelial cells include, but are not limited to, dermal keratinocyte, ocular epithelial cells, corneal epithelial cells, oral mucosal epithelial cells, esophagus epithelial cells, and cervix epithelial cells.

Non-keratinocyte (NKE) epithelial cells form the epithelium of the body such as found in the breast, prostate, liver, respiratory tract, retina and gastrointestinal tract. NKE cells typically differentiate into functional, viable cells which function, for example, in absorption and/or secretion. These cells typically do not form highly keratinized structures characteristic of squamous epithelial cells. Examples of NKE cells include, but are not limited to, prostate cells, mammary cells, hepatocytes, liver epithelial cells, biliary epithelial cells, gall bladder cells, pancreatic islet cells, pancreatic beta cells, pancreatic ductal epithelial cells, pulmonary epithelial cells, airway epithelial cells, nasal epithelial cells, kidney cells, bladder cells, urethral epithelial cells, stomach epithelial cells, large intestinal epithelial cells, small intestinal epithelial cells, testicular epithelial cells, ovarian epithelial cells, fallopian tube epithelial cells, thyroid cells, parathyroid cells, adrenal cells, thymus cells, pituitary cells, glandular cells, amniotic epithelial cells, retinal pigmented epithelial cells, sweat gland epithelial cells, sebaceous epithelial cells and hair follicle cells.

Cytokine, Chemokine, and Growth Factor Production

Certain methods described herein include measuring production of one or more cytokines and/or chemokines. Certain methods described herein include measuring production of one or more cytokines, chemokines, and/or growth factors.

Cytokines generally refer to small proteins (generally about 5-20 kDa) that are involved in cell signaling, and a release of cytokines can have an effect on the behavior of cells nearby. Cytokines are often considered as immuno-modulating agents and may be involved in autocrine signaling, paracrine signaling and endocrine signaling. Cytokines may include chemokines, interferons, interleukins, lymphokines, monokines, colony stimulating factors, and tumor necrosis factors. Cytokines may be produced by immune cells (e.g., monocytes, macrophages, B lymphocytes, T lymphocytes, and mast cells), endothelial cells, fibroblasts, and stromal cells.

In some embodiments, a method herein comprises measuring production by a cell of one or more cytokines. In some embodiments, a method herein comprises measuring production by a cell of one or more interleukins. In some embodiments, a method herein comprises measuring production by a cell of one or more IL-6 family cytokines. In some embodiments, a method herein comprises measuring production by a cell of one or more IL-1 family cytokines. A method herein may include measuring production of one or more cytokines provided in Table 1 below. Also provided in Table 1 are corresponding human genes and human receptors, however, cytokines, genes and receptors listed in Table 1 are not limited to human cytokines, genes and receptors. In some embodiments, a method herein comprises measuring production by a cell of a cytokine that binds to one or more receptors provided in Table 1.

TABLE 1

Examples of cytokines

| Cytokine | Human gene | Human receptor(s) |
|---|---|---|
| IL-6 family | | |
| IL-6 | Interleukin 6 | IL6R (CD126), GP130, sIL6R |
| IL-11 | Interleukin 11 | IL11R |
| Oncostatin M | Oncostatin M | LIPR/IL6ST/OSMR |
| Ciliary neurotrophic factor | Ciliary Neurotrophic Factor | CNTFR |
| NNT-1/BSF-3/CLC | Novel Neurotrophin-1/B-Cell Stimulating Factor-3 Cardiotrophin-Like Cytokine Factor 1 | CNTFR |

TABLE 1-continued

Examples of cytokines

| Cytokine | Human gene | Human receptor(s) |
|---|---|---|
| Cardiotrophin-1 | Cardiotrophin 1 | GP130/LIFR |
| Leukemia inhibitory factor | Leukemia inhibitory factor | GP130/LIFR |
| IL-27 | Interleukin 27 | IL27RA/GP130 |
| IL-31 | Interleukin 31 | IL31RA/OSMR |
| IL-1 family | | |
| IL-1RA | Interleukin 1 Receptor Antagonist | IL1R |
| IL-1α | Interleukin 1 Alpha | IL1R |
| IL-1β | Interleukin 1 Beta | |
| IL-18 | Interleukin 18 | IL18RA/IL18RB |
| IL-33 | Interleukin 33 | ST2/IL-1 R4 / IL-1 RAcP |
| IL-36α | Interleukin 36 alpha | IL-1 Rrp2 / IL-1 RAcP |
| IL-36β | Interleukin 36 beta | IL-1 Rrp2 / IL-1 RAcP |
| IL-36γ | Interleukin 36 gamma | IL-1 Rrp2 / IL-1 RAcP |
| IL-36Ra | Interleukin 36 Receptor Antagonist | IL-1 Rrp2 / IL-1 RAcP |
| IL-37 | Interleukin 37 | IL18RA |
| IL-38 | Interleukin 38 | IL-1 RI/ IL1 Rrp2 |

Chemokines generally refer to a sub-family of cytokines (signaling proteins secreted by cells). Chemokines can induce directed chemotaxis in nearby responsive cells, and may be referred to as chemotactic cytokines. Chemokines are small (generally about 8-10 kDa) and typically have four cysteine residues in conserved locations for forming their 3-dimensional shape. Certain chemokines are pro-inflammatory and can be induced during an immune response to recruit cells of the immune system to a site of infection, and certain chemokines are homeostatic and are involved in controlling the migration of cells during normal processes of tissue maintenance or development. Chemokines may be classified into subfamilies (i.e., C, CX3C, CC and CXC), and exert their biological effects by interacting with G protein-linked transmembrane receptors (chemokine receptors), that are found on the surface of target cells.

In some embodiments, a method herein comprises measuring production by a cell of one or more chemokines. In some embodiments, a method herein comprises measuring production by a cell of one or more C-family chemokines. In some embodiments, a method herein comprises measuring production by a cell of one or more CX3C-family chemokines. In some embodiments, a method herein comprises measuring production by a cell of one or more CC-family chemokines. In some embodiments, a method herein comprises measuring production by a cell of one or more CXC-family chemokines. A method herein may include measuring production of one or more chemokines provided in Table 2 below. Also provided in Table 2 are corresponding human genes and human receptors, however, chemokines, genes and receptors herein are not limited to human chemokines, genes and receptors. In some embodiments, a method herein comprises measuring production by a cell of a chemokine that binds to one or more receptors provided in Table 2.

TABLE 2

Examples of chemokines

| Chemokine | Human gene | Human receptor(s) |
|---|---|---|
| C Family | | |
| XCL1 | XCL1 | XCR1 |
| XCL2 | XCL2 | XCR1 |

TABLE 2-continued

Examples of chemokines

| Chemokine | Human gene | Human receptor(s) |
|---|---|---|
| CX3C Family | | |
| CX3CL1 | CX3CL1 | CXCR1 |
| CC Family | | |
| CCL1 | CCL1 | CCR8, DARC |
| CCL2 | CCL2 | CCR2, CCR4, CCR11, D6, DARC |
| CCL3 | CCL3 | CCR1, CCR4, CCR5, D6 |
| CCL3L1 | CCL3L1 | CCR1, CCR3, CCR5, D6 |
| CCL3L3 | CCL3L3 | CCR1, CCR3, CCR5 |
| CCL4 | CCL4 | CCR1, CCR5, CCR8, D6 |
| CCL4L1 | CCL4L1 | CCR1, CCR5 |
| CCL4L2 | CCL4L2 | CCR1, CCR5 |
| CCL5 | CCL5 | CCR1, CCR3, CCR4, CCR5, D6, DARC |
| CCL61 | CCL23 | |
| CCL7 | CCL7 | CCR1, CCR2, CCR3, D6, DARC |
| CCL8 | CCL8 | CCR1, CCR2, CCR3, CCR5, CCR11, D6, DARC |
| CCL11 | CCL11 | CCR3, CCR5, D6, DARC |
| CCL12 | | |
| CCL13 | CCL13 | CCR1, CCR2, CCR3, CCR5, CCR11, D6, DARC |
| CCL14 | CCL14 | CCR1, CCR3, CCR5, D6, DARC |
| CCL15 | CCL15 | CCR1, CCR3 |
| CCL16 | CCL16 | CCR1, CCR2, CCR5, CCR8, DARC, H4 |
| CCL17 | CCL17 | CCR4, CCR8, D6, DARC |
| CCL18 | CCL18 | CCR8, PITPNM3, DARC |
| CCL19 | CCL19 | CCR7, CCR11, CCRL2/ CRAM A/B |
| CCL20 | CCL20 | CCR6 |
| CCL21 | CCL21 | CCR7, CCR11 |
| CCL22 | CCL22 | CCR4, D6 |
| CCL23 | CCL23 | CCR1, FPRL-1 |
| CCL24 | CCL24 | CCR3 |
| CCL25 | CCL25 | CCR9, CCR11 |
| CCL26 | CCL26 | CCR3, CX3CR1 |
| CCL27 | CCL27 | CCR10 |
| CCL28 | CCL28 | CCR3, CCR10 |
| CXC Family | | |
| CXCL1 | CXCL1 | CXCR2, DARC |
| CXCL2 | CXCL2 | CXCR2, DARC |
| CXCL3 | CXCL3 | CXCR2, DARC |
| CXCL4 | PF4 | CXCR3, CXCR3B, DARC |
| CXCL4L1 | PF4V1 | CXCR3, CXCR3B |
| CXCL5 | CXCL5 | CXCR2, DARC |
| CXCL6 | CXCL6 | CXCR1, CXCR2, DARC |
| CXCL7 | PPBP | CXCR1, CXCR2 |
| CXCL8 | IL-8 | CXCR1, CXCR2, DARC |
| CXCL9 | CXCL9 | CXCR3, CXCR3B, DARC |
| CXCL10 | CXCL10 | CXCR3, CXCR3B, DARC |
| CXCL11 | CXCL11 | CXCR3, CXCR3B, CXCR7, DARC |
| CXCL12 | CXCL12 | CXCR4, CXCR7 |
| CXCL13 | CXCL13 | CXCR3, CXCR5, DARC |
| CXCL14 | CXCL14 | Unknown |
| CXCL15 | | |
| CXCL16 | CXCL16 | CXCR6 |
| CXCL17 | CXCL17 | Unknown |
| LIX | | |

Growth factors generally refer to a substance capable of stimulating cellular growth, proliferation, healing, cellular differentiation, and the like. A growth factor may be a protein or a hormone (e.g., steroid hormone). In certain instances, cytokines may be categorized as growth factors. Growth factors may include, for example, erythropoietin, platelet-derived growth factor (PDGF), PDGF-AA, and vascular endothelial growth factor (VEGF).

In some embodiments, a method herein comprises measuring production by a cell of one or more cytokines and/or chemokines chosen from CCL2, CCL3, CCL4, CCL5, CCL11, CCL17, CCL20, CXCL1, CXCL5, CXCL8, CXCL9, CXCL10, CXCL11, IL-1RA, and IL-6. In some embodiments, a method herein comprises measuring production by a cell of one or more cytokines, chemokines and/or growth factors chosen from CCL2, CCL3, CCL4, CCL5, CCL11, CCL17, CCL20, CXCL1, CXCL5, CXCL8, CXCL9, CXCL10, CXCL11, IL-1RA, IL-6, erythropoietin, PDGF-AA, and VEGF. In some embodiments, a method herein comprises measuring production by a cell of one or more cytokines and/or chemokines chosen from CCL2, CCL3, CCL4, CCL5, CCL11, CXCL8, CXCL10, and IL-1RA. In some embodiments, a method herein comprises measuring production by a cell of one or more cytokines, chemokines, and/or growth factors chosen from CCL2, CCL3, CCL4, CCL5, CCL11, CXCL8, CXCL10, IL-1RA, erythropoietin, PDGF-AA, and VEGF. In some embodiments, a method herein comprises measuring production by a cell of CCL2. In some embodiments, a method herein comprises measuring production by a cell of CCL3. In some embodiments, a method herein comprises measuring production by a cell of CCL4. In some embodiments, a method herein comprises measuring production by a cell of CCL5. In some embodiments, a method herein comprises measuring production by a cell of CCL11. In some embodiments, a method herein comprises measuring production by a cell of CCL17. In some embodiments, a method herein comprises measuring production by a cell of CCL20. In some embodiments, a method herein comprises measuring production by a cell of CXCL1. In some embodiments, a method herein comprises measuring production by a cell of CXCL5. In some embodiments, a method herein comprises measuring production by a cell of CXCL8. In some embodiments, a method herein comprises measuring production by a cell of CXCL9. In some embodiments, a method herein comprises measuring production by a cell of CXCL10. In some embodiments, a method herein comprises measuring production by a cell of CXCL11. In some embodiments, a method herein comprises measuring production by a cell of IL-1RA. In some embodiments, a method herein comprises measuring production by a cell of IL-6. In some embodiments, a method herein comprises measuring production by a cell of erythropoietin. In some embodiments, a method herein comprises measuring production by a cell of PDGF-AA. In some embodiments, a method herein comprises measuring production by a cell of VEGF.

Cytokine, chemokine, and/or growth factor production may be measured using any suitable method, apparatus or machine for measuring protein secretion and/or DNA expression (e.g., mRNA). For example, cytokine, chemokine, and/or growth factor production may be measured by immunoassay (e.g., enzyme-linked immunosorbent assay (ELISA), protein immunoprecipitation, immunoelectrophoresis, Western blot, protein immunostaining), spectrometry (e.g., high-performance liquid chromatography (HPLC), liquid chromatography-mass spectrometry (LC/MS)), flow cytometry, quantitative polymerase chain reaction (qPCR), gel electrophoresis, a luminometer, a fluorometer, a spectrophotometer, a suitable gene-chip or microarray analysis, mass spectrometry, chromatography, cytofluorimetric analysis, fluorescence microscopy, a suitable fluorescence or digital imaging method, confocal laser scanning microscopy, laser scanning cytometry, affinity chromatography, manual batch mode separation, electric field suspension, a suitable nucleic acid sequencing method and/or nucleic acid sequencing apparatus, the like and combinations thereof. Example immunoassays include LEGEND MAX™ ELISA kits with pre-coated plates (BioLegend), Macrophage/Microglia LEGENDplex™ panels (BioLegend), and Chemokine Inflammatory LEGENDplex™ panels (BioLegend).

Methods for Assessing IL-40 Activity

Provided herein are methods for assessing IL-40 activity. Methods for assessing IL-40 activity generally are performed ex vivo (i.e., outside of an organism) or in vitro (i.e., performed or taking place in a test tube, culture dish, or other vessel outside of an organism). The terms ex vivo and in vitro may be used interchangeably, and typically are used in conjunction with methods performed in an artificial environment or artificial system. Methods herein generally include contacting a cell with IL-40 or IL-40 and a co-stimulant, and such contacting is typically performed ex vivo/in vitro (e.g., in cell culture).

In some embodiments, a method comprises contacting a cell with IL-40, measuring production of one or more cytokines, chemokines, and/or growth factors described herein, and detecting the activity of IL-40 according to the cytokine production. In some embodiments, detecting the activity of IL-40 comprises comparing the cytokine/chemokine/growth factor production under test conditions (IL-40 stimulation) to cytokine/chemokine/growth factor production under control conditions (no IL-40 stimulation). In some embodiments, detecting the activity of IL-40 comprises comparing cytokine/chemokine/growth factor production under test conditions to cytokine/chemokine/growth factor production in a standard curve (e.g., cytokine/chemokine/growth factor production measured for a plurality of different amounts of active IL-40). An active IL-40 may include an IL-40 standard (e.g., an unmodified full-length mature IL-40; a full-length mature IL-40 comprising activity-enhancing modifications). In some embodiments, detecting the activity of IL-40 comprises comparing cytokine/chemokine/growth factor production under test conditions to cytokine/chemokine/growth factor production measured for a control, thereby providing a comparison. A control may include, for example, cytokine/chemokine/growth factor production measured in the absence of IL-40. Typically, for a control, or for generating a standard curve, cytokine production is measured for the same cell (e.g., same cell-type, same cellular source, and/or same cell population) used for assessing IL-40 activity (test conditions). Typically, for a control, or for generating a standard curve, cytokine/chemokine/growth factor production can be a measured level of a cytokine/chemokine/growth factor, or measured levels of cytokines/chemokines/growth factors in a combination of cytokines, chemokines, growth factors; or cytokines and chemokines; or cytokines and growth factors; or chemokines and growth factors; or cytokines, chemokines and growth factors. Often, the level of the same cytokine/chemokine/growth factor, or the levels of the same cytokines, chemokines, or cytokines and chemokines, or cytokines and growth factors, or chemokines and growth factors, or cytokines, chemokines and growth factors in the same cytokine/chemokine/growth factor combination, is/are measured for test conditions and for control conditions or conditions for a standard curve.

In some embodiments, a method comprises contacting a cell with IL-40 and a co-stimulant (e.g., IFN-γ, GM-CSF, IFN-α, IL-1β, IL-4, IL-10, IL-13, M-CSF, TGF-β, TNF-α), measuring production of one or more cytokines, chemokines, and/or growth factors described herein, and detecting the activity of IL-40 according to the cytokine, chemokine, and/or growth factor production. In some embodiments, detecting the activity of IL-40 comprises comparing the cytokine/chemokine/growth factor production under test conditions (IL-40+co-stimulant) to cytokine/chemokine/ growth factor production under control conditions (no IL-40, no co-stimulant, or no IL-40+co-stimulant). In some embodiments, detecting the activity of IL-40 comprises comparing cytokine/chemokine/growth factor production under test conditions to cytokine/chemokine/growth factor production in a standard curve (e.g., cytokine/chemokine/growth factor production measured for a plurality of different amounts of active IL-40 or active IL-40+co-stimulant). An active IL-40 may include an IL-40 standard (e.g., an unmodified full-length mature IL-40; a full-length mature IL-40 comprising activity-enhancing modifications). In some embodiments, detecting the activity of IL-40 comprises comparing cytokine/chemokine/growth factor production under test conditions to cytokine/chemokine/growth factor production measured for a control, thereby providing a comparison. A control may include, for example, cytokine/chemokine/growth factor production measured in the absence of IL-40; cytokine/chemokine/growth factor production measured in the absence of a co-stimulant; cytokine/chemokine/growth factor production measured in the absence of IL-40 and a co-stimulant. Typically, for a control, or for generating a standard curve, cytokine/chemokine/growth factor production is measured for the same cell (e.g., same cell-type, same cellular source, and/or same cell population) used for assessing IL-40 activity (test conditions). Typically, for a control, or for generating a standard curve, cytokine/chemokine/growth factor production can be a measured level of a cytokine/chemokine/growth factor, or measured levels of cytokines/chemokines/growth factors in a combination of cytokines, chemokines, growth factors, or cytokines and chemokines, or cytokines and growth factors, or chemokines and growth factors, or cytokines, chemokines, and growth factors. Often, the level of the same cytokine/chemokine/growth factor, or the levels of the same cytokines, chemokines, growth factors, or cytokines and chemokines, or cytokines and growth factors, or chemokines and growth factors, or cytokines, chemokines, and growth factors, in the same cytokine/chemokine/growth factor combination, is/are measured for test conditions and for control conditions or conditions for a standard curve.

In some embodiments, the production of one or more cytokines, chemokines, and/or growth factors under test conditions (i.e., under IL-40 stimulation or under IL-40+co-stimulant stimulation) is increased compared to the production under control conditions (i.e., absence of IL-40 or IL-40+co-stimulant). In some embodiments, production of one or more cytokines, chemokines, and/or growth factors under test conditions is increased by at least about 10% compared to the production under control conditions. For example, production of one or more cytokines, chemokines, and/or growth factors under test conditions may be increased by at least about 10%, 20%, 30%, 40%, 50%, 60%, 70%, 80%, 90%, 100%, 200%, 500%, 1000% or more compared to the production under control conditions. In some embodiments, production of one or more cytokines, chemokines, and/or growth factors under test conditions is increased by at least about 2-fold compared to the production under control conditions. For example, production of one or more cytokines, chemokines, and/or growth factors under test conditions may be increased by at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold or more compared to the production under control conditions.

In some embodiments, a method comprises contacting a cell or population of cells with IL-40, detecting differentiation of the cell or differentiation of one or more cells in the population, and assessing the activity of IL-40 according to the differentiation. In some embodiments, a method comprises contacting a population of immune cells with IL-40, detecting differentiation of one or more immune cells in the population, and assessing the activity of IL-40 according to the differentiation. In some embodiments, a method comprises contacting a population of monocytes with IL-40, detecting monocyte to macrophage differentiation in the population, and assessing the activity of IL-40 according to the monocyte to macrophage differentiation. Macrophage differentiation may refer to any stage of macrophage differentiation including, but not limited to, M1, M2a, M2b, M2c, and M2d.

Monocyte to macrophage differentiation may be detected according to changes in cell morphology. For example, monocyte to macrophage differentiation may be characterized by attachment/adhesion to a culture plate, cells with a flattened and/or spreading appearance, cells with feelers/extensions/protrusions, and/or cells with irregular shape (compared to spherical or substantially spherical monocytes). In some embodiments, monocyte to macrophage differentiation under test conditions (i.e., under IL-40 stimulation or under IL-40+co-stimulant stimulation) is observed for a portion of cells in the population, compared to no or substantially no (e.g., less than 1%) monocyte to macrophage differentiation under control conditions (i.e., absence of IL-40 or IL-40+co-stimulant). For example, monocyte to macrophage differentiation under test conditions may be observed for at least about 5%, 10%, 20%, 30%, 40%, 50%, 60%, 70%, 80%, 90% or 100% of cells in the population. In some embodiments, monocyte to macrophage differentiation under IL-40 stimulation is observed for at least about 10% of cells in the population. In some embodiments, monocyte to macrophage differentiation under IL-40+co-stimulant stimulation is observed for at least about 30% of cells in the population.

Monocyte to macrophage differentiation may be detected according to changes in expression and/or production of one or more markers, cytokines, chemokines, and/or growth factors. In some embodiments, monocyte to macrophage differentiation is detected according to expression (presence or absence, increased, or decreased) of one or more markers (e.g., cell-surface markers). Expression of markers may be detected and/or quantified using any suitable method for detecting cell surface proteins (e.g., immunoassay (ELISA), flow cytometry) and/or mRNA expression (e.g., reverse transcriptase quantitative PCR). In some embodiments, monocyte to macrophage differentiation is detected according to production (presence or absence, increased, or decreased) of one or more cytokines, chemokines, and/or growth factors. Production of cytokines, chemokines, and/or growth factors may be detected and/or quantified using any suitable method for detecting secreted proteins (e.g., detection methods described herein). Presence, absence, increases, and decreases of markers, cytokines, chemokines, and/or growth factors may be determined by measuring levels of expression or production under test conditions (i.e., stimulation by IL-40 or stimulation by IL-40+co-stimulant) compared to levels of expression or production under control conditions (i.e., absence of IL-40 or absence of IL-40+co-stimulant).

Examples of markers useful for identifying monocyte to macrophage differentiation are provided in Table 3 below.

TABLE 3

| Markers for monocytes/macrophages | | |
| --- | --- | --- |
| Protein marker | Estimated expression level in monocytes | Estimated expression level in macrophages |
| CD14 | ++++/++ | ++ |
| Ly6C | ++++/++ | + |
| CD115 | ++++ | + |
| CD15s | ++ | + |
| CD33 | ++++ | ++ |
| CD44 | ++ | ++++ |
| CD81 | ++ | ++++ |
| CD49e | ++ | ++++ |
| CD18 | ++ | ++++ |
| CD11b | ++ | ++++ |
| CD54 (ICAM-1) | ++ | ++++ |
| CD11c | + | +++ |
| CD68 | ++ | ++++ |
| CD80 | ++ | ++++ |
| CD86 | ++ | ++++ |
| CD163 | ++ | ++++ |
| IL-1R | ++ | ++++ |
| CD200R | ++ | ++++ |

Examples of cytokines and chemokines useful for identifying monocyte to macrophage differentiation are provided in Table 4 below.

TABLE 4

| Chemokines and cytokines having increased secretion in macrophages | |
| --- | --- |
| Chemokines | Cytokines |
| CCL10 | TNF |
| CCL11 | IL-1 beta |
| CCL5 | IL-6 |
| CCL8 | IL-12 |
| CCL9 | IL-23 |
| CCL2 | IL-10 |
| CCL3 | TGF-beta |
| CCL4 | IL-1RA |
| CCL17 | IL-1 |
| CCL22 | TNF-alpha |
| CCL24 | IL-10 |
| CCL1 | |
| CCR2 | |
| CCL5 | |
| CXCL10 | |
| CXCL8 | |
| CXCL9 | |
| CXCL16 | |

In some embodiments, monocyte to macrophage differentiation is detected according to expression of one or more markers chosen from CD14, Ly6C, CD115, CD15s, CD33, CD44, CD81, CD49e, CD18, CD11b, CD54 (ICAM-1), CD11c, CD68, CD80, CD86, CD163, IL-1R, and CD200R. In some embodiments, monocyte to macrophage differentiation is detected according to increased expression of one or more markers chosen from CD44, CD81, CD49e, CD18, CD11b, CD54 (ICAM-1), CD11c, CD68, CD80, CD86, CD163, IL-1R, and CD200R. In some embodiments, monocyte to macrophage differentiation is detected according to decreased expression of one or more markers chosen from CD14, Ly6C, CD115, CD15s, and CD33. In some embodiments, monocyte to macrophage differentiation is detected according to increased production of one or more chemokines chosen from CCL10, CCL11, CCL5, CCL8, CCL9, CCL2, CCL3, CCL4, CCL17, CCL22, CCL24, CCL1, CCR2, CCL5, CXCL10, CXCL8, CXCL9, and CXCL16. In some embodiments, monocyte to macrophage differentiation is detected according to increased production of one or more cytokines chosen from TNF, IL-1 beta, IL-6, IL-12, IL-23, IL-10, TGF-beta, IL-1RA, IL-1, TNF-alpha, and IL-10.

Methods for Inducing Cell Differentiation

Certain methods herein include inducing cell differentiation. Cell differentiation may be induced ex vivo or in vitro according to methods herein. In some embodiments, cell differentiation is induced by contacting a cell or population of cells with IL-40. Certain methods herein include inducing immune cell differentiation. In some embodiments, immune cell differentiation is induced by contacting an immune cell or a population of immune cells with IL-40. Certain methods herein include inducing monocyte to macrophage differentiation. In some embodiments, monocyte to macrophage differentiation is induced by contacting a monocyte or a population of monocytes with IL-40. Macrophage differentiation may refer to any stage of macrophage differentiation including, but not limited to, M1, M2a, M2b, M2c, and M2d.

Monocyte to macrophage differentiation may be detected according to changes in cell morphology. Methods for assessing changes in cell morphology are described herein. Monocyte to macrophage differentiation may be detected according to changes in expression and/or production of one or more markers, cytokines, chemokines, and/or growth factors. Markers, cytokines, chemokines, and/or growth factors useful for detecting monocyte to macrophage differentiation, and methods for detecting/quantifying their expression/production, are described herein.

Kits

Provided in certain embodiments are kits. The kits may include any components and compositions described herein (e.g., IFN-γ, GM-CSF, IFN-α, IL-1β, IL-4, IL-10, IL-13, M-CSF, TGF-β, and/or TNF-α; one or more components for measuring cytokine, chemokine, and/or growth factor production, a cell or population of cells) useful for performing any of the methods described herein, in any suitable combination. In some embodiments, a kit further includes IL-40 (e.g., for use as a standard/control and/or for the user to generate a standard curve). IL-40 for testing may be provided by the user/purchaser of the kit. Kits may further include any reagents, buffers, or other components useful for carrying out any of the methods described herein. For example, a kit may include one or more binding molecules that immunospecifically bind to one or more cytokines, chemokines, and/or growth factors under binding conditions.

Components of a kit may be present in separate containers, or multiple components may be present in a single container. Suitable containers include a single tube (e.g., vial), a cell culture plate, one or more wells of a plate (e.g., a 6-well plate, a 12-well plate, a 24-well plate, a 96-well plate, a 384-well plate, and the like), and the like.

Kits may also comprise instructions for performing one or more methods described herein and/or a description of one or more components described herein. Instructions and/or descriptions may be in printed form and may be included in a kit insert. In some embodiments, instructions and/or descriptions are provided as an electronic storage data file present on a suitable computer readable storage medium, e.g., portable flash drive, DVD, CD-ROM, diskette, and the like. A kit also may include a written description of an internet location that provides such instructions or descriptions.

EXAMPLES

The examples set forth below illustrate certain embodiments and do not limit the technology.

Example 1: Production of Cytokines and Chemokines by THP-1 Cells and Changes in Cell Morphology Under IL-40 Stimulation In this Example, the production of certain cytokines and chemokines by THP-1 cells under IL-40 stimulation and IFN-γ+IL-40 co-stimulation was measured. Changes in cell morphology of THP-1 cells under IL-40 stimulation and IFN-γ+IL-40 co-stimulation also was observed.

Materials and Methods

Recombinants Proteins

The nucleic acid encoding the c17orf99 (chromosome 17 open reading frame 99) [Homo sapiens (human) NCBI Reference Sequence: NP_001156547], also known as IL-40, or UNQ464, was used to produce recombinant human protein IL-40 (rhIL-40). The protein contains an Fc fraction at the C terminus for recovery and purification purposes. The rhFc fraction from the IgG1 protein was used as a control. The recombinant proteins, rhFc, rhIL-40, IFN-γ (BioLegend cat #570202), IFN-α (BioLegend cat #592702), IL-4 (BioLegend cat #592702), IL-13 (BioLegend cat #571102), TGF-β (BioLegend cat #580704), M-CSF (BioLegend cat #574802), GM-CSF (BioLegend cat #572902), IL-10 (BioLegend cat #715602), TNF-α (BioLegend cat #570102), and IL-1β (BioLegend cat #579402) were obtained from BioLegend.

Cell Culture

The THP-1 cell line was cultured and maintained in RPMI-1640 medium supplemented with 10% fetal bovine serum (FBS), at 37° C. in a humidified atmosphere of 5% $CO_2$. To perform the stimulation experiments, THP-1 cells were cultured in RPM1-1640 medium supplemented with 1.1% FBS. 30,000 THP-1 cells were seeded in a 96-well plate, and stimulated with rhIL-40 (BioLegend, CA) or rhFc fraction (BioLegend, CA) at the same micromolar concentrations, in the presence or absence of IFN-γ (250 or 50 ng/mL), IFN-α, IL-4, Il-13, TGF-β, M-CSF, GM-CSF, IL-10, TNF-α, or IL-1β (50 ng/mL) for 24, 48, or 72 hours in a final volume of 200 μL.

Healthy human PBMCs were isolated from whole blood through density centrifugation. Cells were cultured in RPMI-1640 medium supplemented with 1.1% FBS. 30,000 PBMCs were seeded in a 96-well plate, and stimulated with rhIL-40 (BioLegend, CA) or rhFc fraction (control) at the same micromolar concentrations for 24 hours in a final volume of 200 μL.

Cytokines and Chemokines Quantification

The concentration of CCL2, CCL3, CCL4, CCL5, CCL11, CCL17, CCL20, CXCL1, CXCL5, CXCL8, CXCL9, CXCL10, CXCL11, IL-12p70, IL-12p40, TNF-α, IL-6, IL-4, IL-10, IL-1β, Arginase, IL-1RA and IL-23, were measured in the cell culture supernatant using LEGEND MAX ELISA kits with pre-coated plates, or human Macrophage/Microglia and Chemokine Inflammatory LEGENDplex panels. The protocols were followed as suggested by the provider.

Cell Phenotype

Changes in the morphology of THP-1 cells 24 hours after rhIL-40 stimulation were documented using a Keyence BZ-X700 microscope in a phase contrast mode and 10× lenses resolution.

Data Analysis

The effect of different stimuli was normalized. For this purpose, the value in pg/mL of each molecule was divided by the value obtained under control conditions (unstimulated cells).

To quantify the effect of rhIL-40 or rhIL40+IFN-γ in the THP-1 monocytes morphology, the total cell number and cells attached to the plate surface were counted in several fields. The percentage of cells with morphological changes was determined using the following calculation:

(attached cell number×100%)/total cell number.

Results

CXCL8 Production

Figure 1:
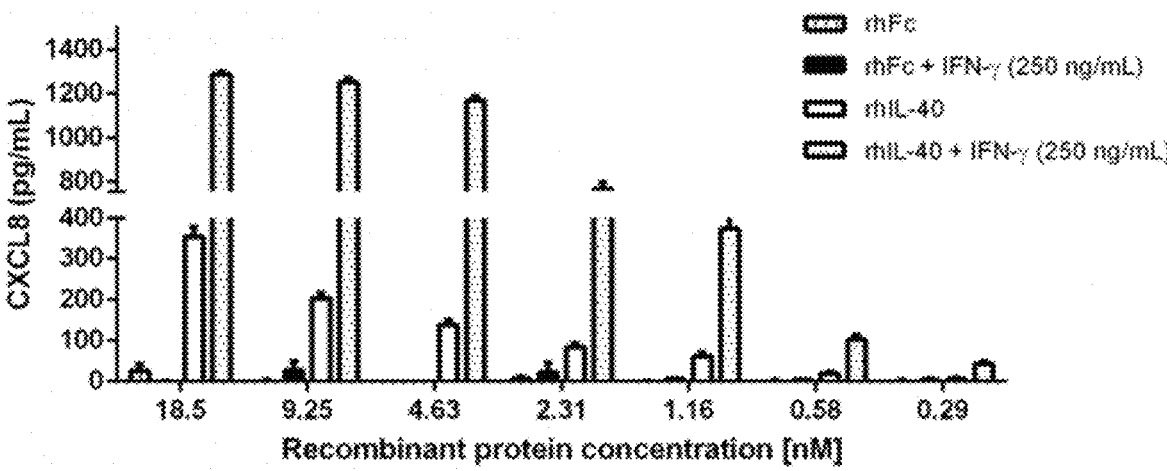
FIG. 1 shows an effect of rhIL-40 on the production of CXCL8 and its activity exacerbation by IFN-γ. Results are shown as the media±SEM, and stimuli are represented as follows: Fc fraction (dashed bars), Fc fraction plus IFN-γ (black bars), rhIL-40 (white bars), and rhIL-40 plus IFN-γ (dotted bars).

The production of CXCL8 was measured in cell supernatants from THP-1 cells stimulated with different concentrations of the recombinant proteins rhFc or rhIL-40 (0.29 μM, 0.58 μM, 1.16 μM, 2.31 μM, 4.63 μM, 9.25 μM, or 18.5 μM)±IFN-γ (250 ng/mL) for 24 hours, and the results are shown in FIG. 1. A dose dependent production of CXCL8 was observed when stimulating cells with rhIL-40 or rhIL-40+IFN-γ. A higher effect was observed after stimulation with rhIL-40+IFN-γ.

CXCL9 Production

Figure 2:
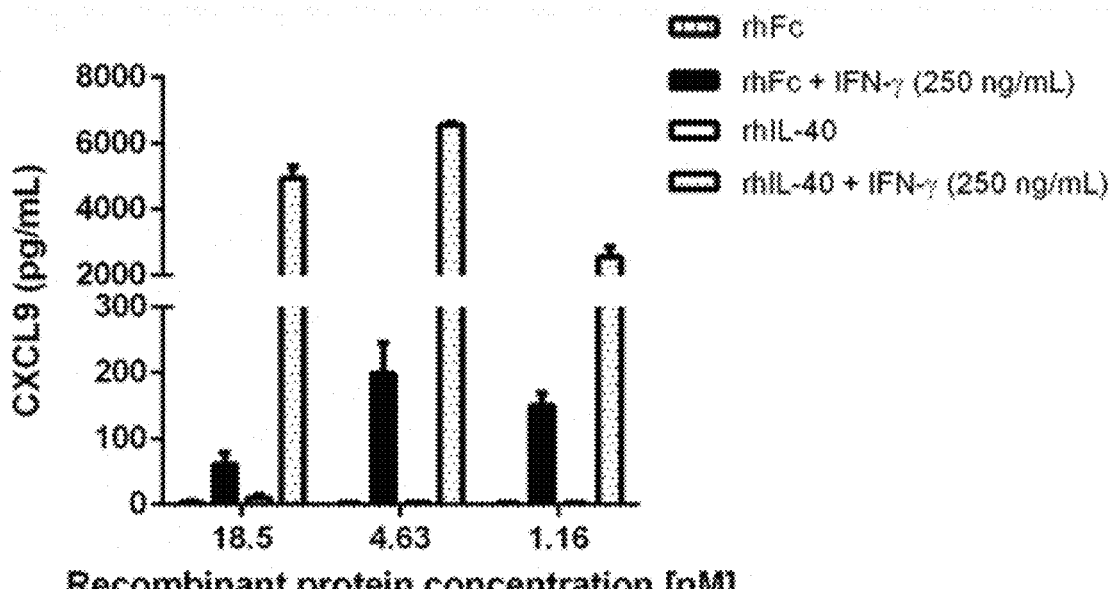
FIG. 2 shows an effect of rhIL-40 plus IFN-γ on the production of CXCL9. Results are shown as the media±SEM, and stimuli are represented as follows: Fc fraction (dashed bars), Fc fraction plus IFN-γ (black bars), rhIL-40 (white bars), and rhIL-40 plus IFN-γ (dotted bars).

The production of CXCL9 was measured in cell supernatants from THP-1 cells stimulated with different concentrations of the recombinant proteins rhFc or rhIL-40 (1.16 μM, 4.63 μM, or 18.5 μM)±IFN-γ (250 ng/mL) for 24 hours, and the results are shown in FIG. 2. A significant increase in production of CXCL9 was observed when stimulating THP-1 cells with rhIL-40+IFN-γ. A lower effect in the CXCL9 secretion also was observed in cells stimulated with rhFc+IFN-γ.

CCL2 Production

Figure 3:
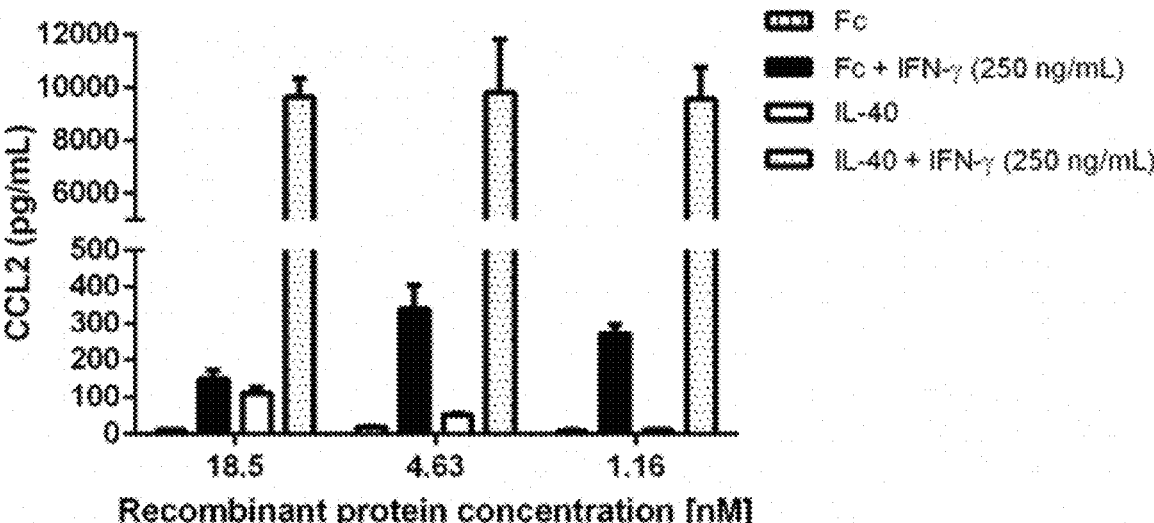
FIG. 3 shows an effect of rhIL-40 on the production of CCL2 and its activity exacerbation by IFN-γ. Results are shown as the media±SEM, and stimuli are represented as follows: Fc fraction (dashed bars), Fc fraction plus IFN-γ (black bars), rhIL-40 (white bars), and rhIL-40 plus IFN-γ (dotted bars).

The production of CCL2 was measured in cell supernatants from THP-1 cells stimulated with different concentrations of the recombinant proteins rhFc or rhIL-40 (1.16 μM, 4.63 μM, or 18.5 μM)±IFN-γ (250 ng/mL) for 24 hours, and the results are shown in FIG. 3. A dose dependent production of CCL2 was observed when stimulating with rhIL-40. Maximum detection level of CCL2 was reached when stimulating cells with rhIL-40+IFN-γ, independent of the rhIL-40 concentration. A lower effect in CCL2 secretion also was observed in cells stimulated with rhFc+IFN-γ.

CCL3 Production

Figure 4:
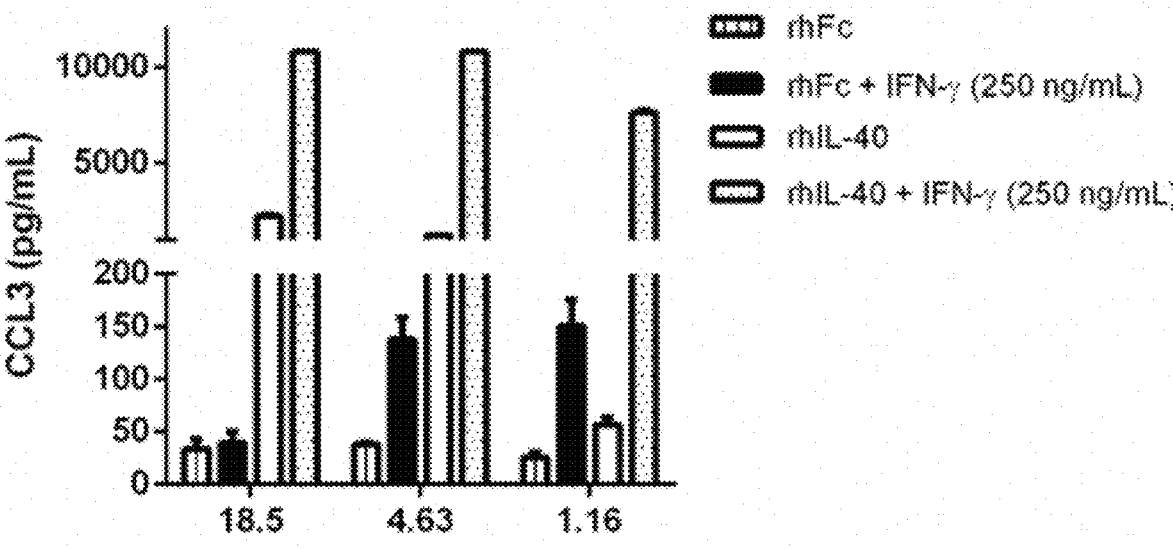
FIG. 4 shows an effect of rhIL-40 on the production of CCL3 and its activity exacerbation by IFN-γ. Results are shown as the media±SEM, and stimuli are represented as follows: Fc fraction (dashed bars), Fc fraction plus IFN-γ (black bars), rhIL-40 (white bars), and rhIL-40 plus IFN-γ (dotted bars).

The production of CCL3 was measured in cell supernatants from THP-1 cells stimulated with different concentrations of the recombinant proteins rhFc or rhIL-40 (1.16 μM, 4.63 μM, or 18.5 μM)±IFN-γ (250 ng/mL) for 24 hours, and the results are shown in FIG. 4. A dose dependent production of CCL3 was observed after stimulation with rhIL-40. A synergic effect was observed when stimulating with rhIL-40+IFN-γ. Similar effects were observed using the two top concentrations evaluated for rhIL-40. An effect in CCL3 secretion also was observed in cells stimulated with rhFc+IFN-γ.

CCL4 Production

Figure 5:
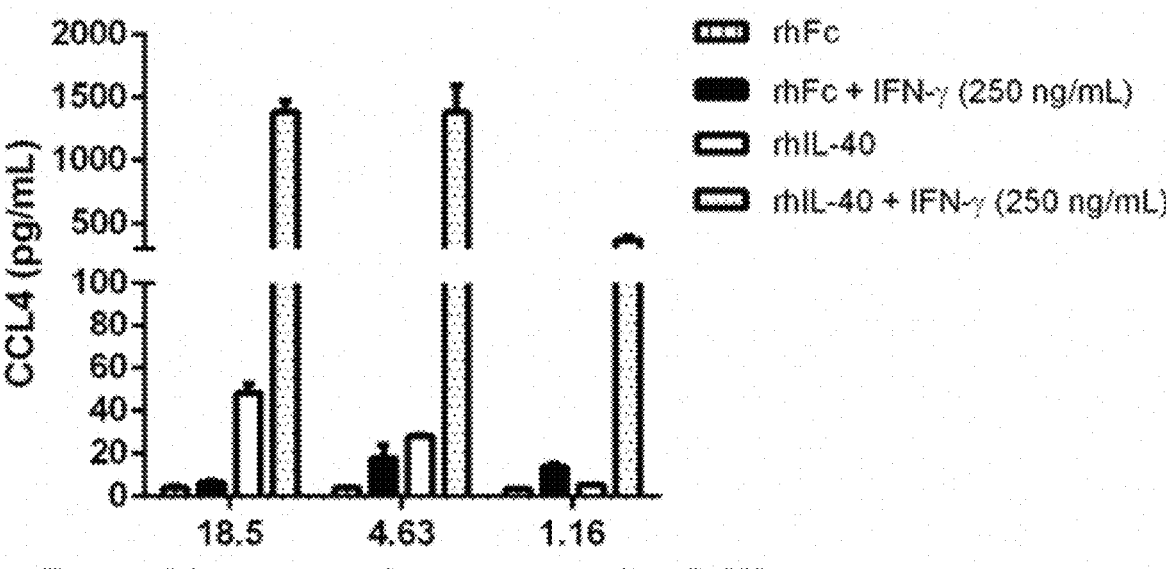
FIG. 5 shows an effect of rhIL-40 on the production of CCL4 and its activity exacerbation by IFN-γ. Results are shown as the media±SEM, and stimuli are represented as follows: Fc fraction (dashed bars), Fc fraction plus IFN-γ (black bars), rhIL-40 (white bars), and rhIL-40 plus IFN-γ (dotted bars).

The production of CCL4 was measured in cell supernatants from THP-1 cells stimulated with different concentrations of the recombinant proteins rhFc or rhIL-40 (1.16 μM, 4.63 μM, or 18.5 μM)±IFN-γ (250 ng/mL) for 24 hours, and the results are shown in FIG. 5. A dose dependent production of CCL4 was observed when stimulating with rhIL-40. A synergic effect was observed when stimulating with rhIL-40+IFN-γ. Similar effects were observed using the two top concentrations evaluated for rhIL-40. An effect in the CCL4 secretion also was observed in cells stimulated with rhFc+IFN-γ.

CCL5 Production

Figure 6:
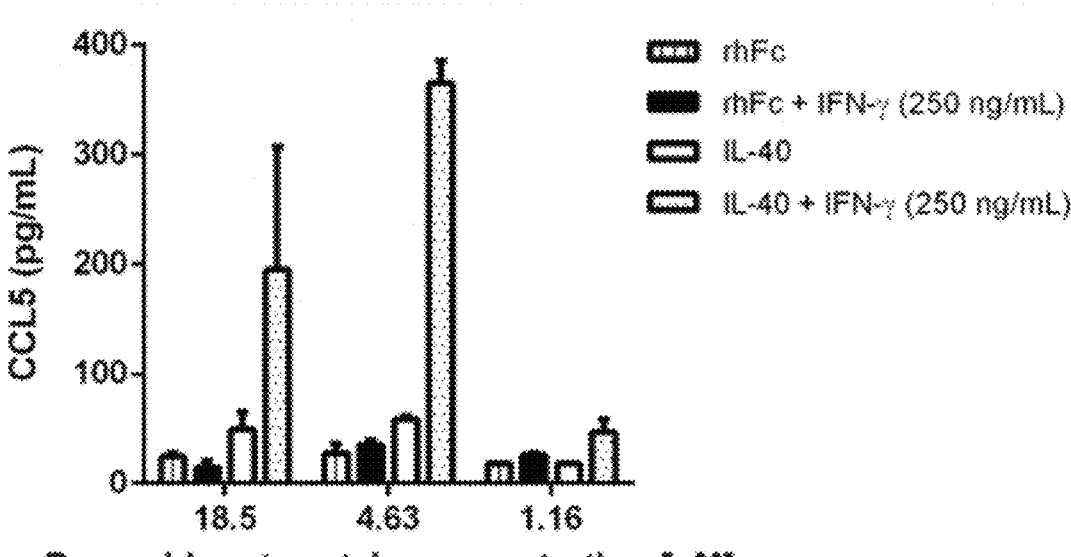
FIG. 6 shows an effect of rhIL-40 on the production of CCL5 and its activity exacerbation by IFN-γ. Results are shown as the media±SEM, and stimuli are represented as follows: Fc fraction (dashed bars), Fc fraction plus IFN-γ (black bars), rhIL-40 (white bars), and rhIL-40 plus IFN-γ (dotted bars).

The production of CCL5 was measured in cell supernatants from THP-1 cells stimulated with different concentrations of the recombinant proteins rhFc or rhIL-40 (1.16 μM, 4.63 μM, or 18.5 μM)±IFN-γ (250 ng/mL) for 24 hours, and the results are shown in FIG. 6. An increase in the production of CCL5 was observed when stimulating with rhIL-40 or rhIL-40+IFN-γ. An effect in CCL5 secretion also was observed in cells stimulated with rhFc and rhFc+IFN-γ.

CXCL10 Production

Figure 7:
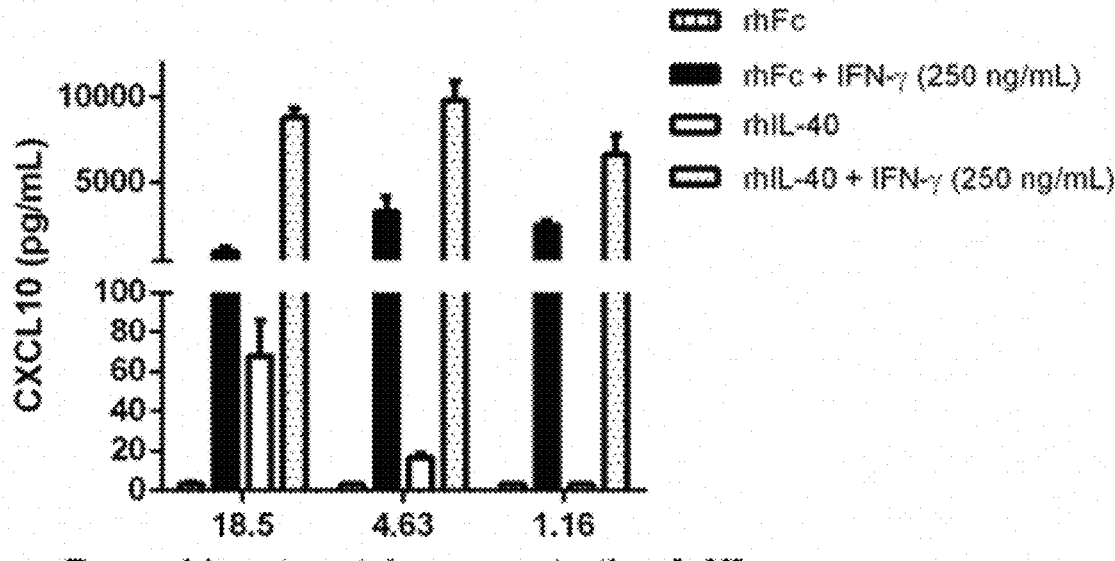
FIG. 7 shows an effect of rhIL-40 plus IFN-γ on the production of CXCL10. Results are shown as the media±SEM, and stimuli are represented as follows: Fc fraction (dashed bars), Fc fraction plus IFN-γ (black bars), rhIL-40 (white bars), and rhIL-40 plus IFN-γ (dotted bars).

The production of CXCL10 was measured in cell supernatants from THP-1 cells stimulated with different concentrations of the recombinant proteins rhFc or rhIL-40 (1.16 μM, 4.63 μM, or 18.5 μM)±IFN-γ (250 ng/mL) for 24 hours, and the results are shown in FIG. 7. A significant increased production of CXCL10 was observed when stimulating THP-1 cells with rhIL40, rhFc+IFN-γ, or rhIL-40+IFN-γ. rhIL-40 alone was able to induce the production of CXCL10. The production of CXCL10 was exacerbated in presence of IFN-γ, showing higher production when combined with rhIL-40.

IL1RA Production

Figure 8:
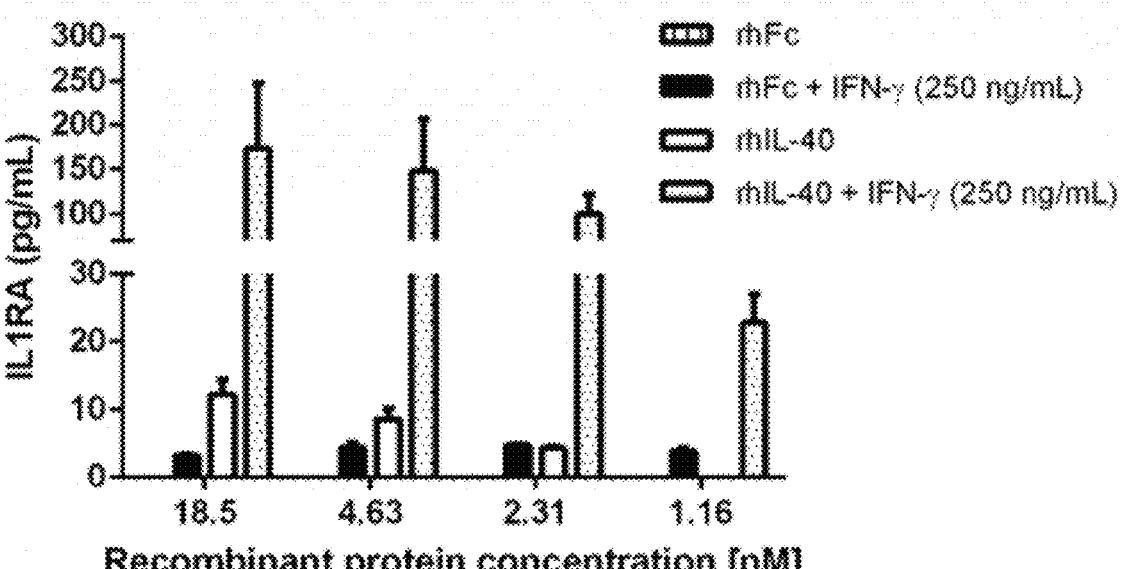
FIG. 8 shows an effect of rhIL-40 plus IFN-γ on the production of IL1RA. Results are shown as the media±SEM, and stimuli are represented as follows: Fc fraction (dashed bars), Fc fraction plus IFN-γ (black bars), rhIL-40 (white bars), and rhIL-40 plus IFN-γ (dotted bars).

The production of IL1RA was measured in cell supernatants from THP-1 cells stimulated with different concentrations of the recombinant proteins rhFc or rhIL-40 (0.58 μM, 2.31 μM, 4.63 μM, or 18.5 μM)±IFN-γ (250 ng/mL) for 24 hours, and the results are shown in FIG. 8. A dose dependent production of IL1RA was observed when stimulating with rhIL-40 or rhIL-40+IFN-γ. A synergic effect was observed when stimulating with rhIL-40+IFN-γ. An effect in IL1RA secretion also was observed in cells stimulated with rhFc+IFN-γ.

IL-6 Production

Figure 9:
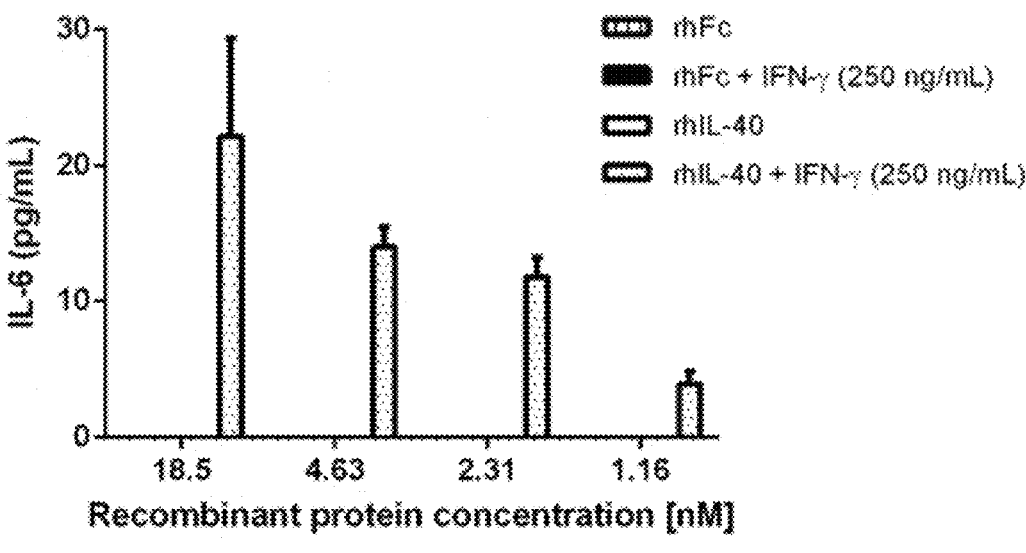
FIG. 9 shows an effect of rhIL-40 plus IFN-γ on the production of IL-6. Results are shown as the media±SEM, and stimuli are represented as follows: Fc fraction (dashed bars), Fc fraction plus IFN-γ (black bars), rhIL-40 (white bars), and rhIL-40 plus IFN-γ (dotted bars).

The production of IL-6 was measured in cell supernatants from THP-1 cells stimulated with different concentrations of the recombinant proteins rhFc or rhIL-40 (0.58 μM, 2.31 μM, 4.63 μM or 18.5 μM)±IFN-γ (250 ng/mL) for 24 hours, and the results are shown in FIG. 9. A significant increase in production of IL-6 was observed when stimulating THP-1 cells with rhIL-40+IFN-γ.

Similar to the effect in the production of chemokines and growth factors by THP-1 cells stimulated with rhIL40 and IFN-γ, an exacerbation in the production of several molecules was observed when cells were stimulated with rhIL40 and IL-10, GM-CSF, TNF-α, or IL-1β for 24 hours.

Erythropoietin Production

Figure 10:
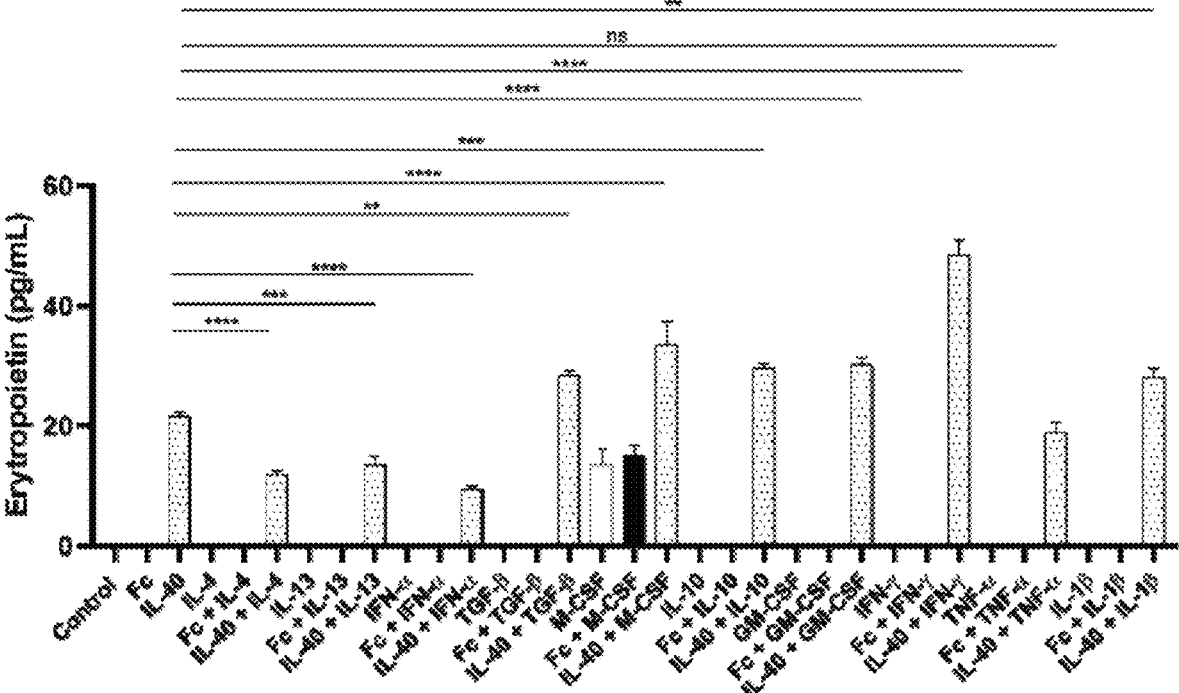
FIG. 10 shows an effect of rhIL40 on the production of erythropoietin and its activity exacerbation by TGF-β, M-CSF, IL-10, GM-CSF, IFN-γ, or IL-1β. Results are shown as the media±SEM, and stimuli are represented as follows: control or cytokine (white bars), Fc fraction or Fc fraction+ cytokine (black bars), rhIL40 or rhIL40+cytokine (dotted bars).

The production of erythropoietin was measured in cell supernatants from THP-1 cells stimulated with different concentrations of the recombinant proteins rhFc or rhIL-40 (4.63 μM μM)±50 ng/mL of IL-4, IL-13, IFN-α, TGF-β, M-CSF, IL-10, GM-CSF, IFN-γ, TNF-α, or IL-1β for 24 hours, and the results are shown in FIG. 10. A significant increase in production of erythropoietin was observed when stimulating THP-1 cells with rhIL-40, and its production was exacerbated when cells were co-stimulated with rhIL40 plus TGF-β, M-CSF, IL-10, GM-CSF, IFN-γ, or IL-1β.

PDGF-AA Production

Figures 11, 12:
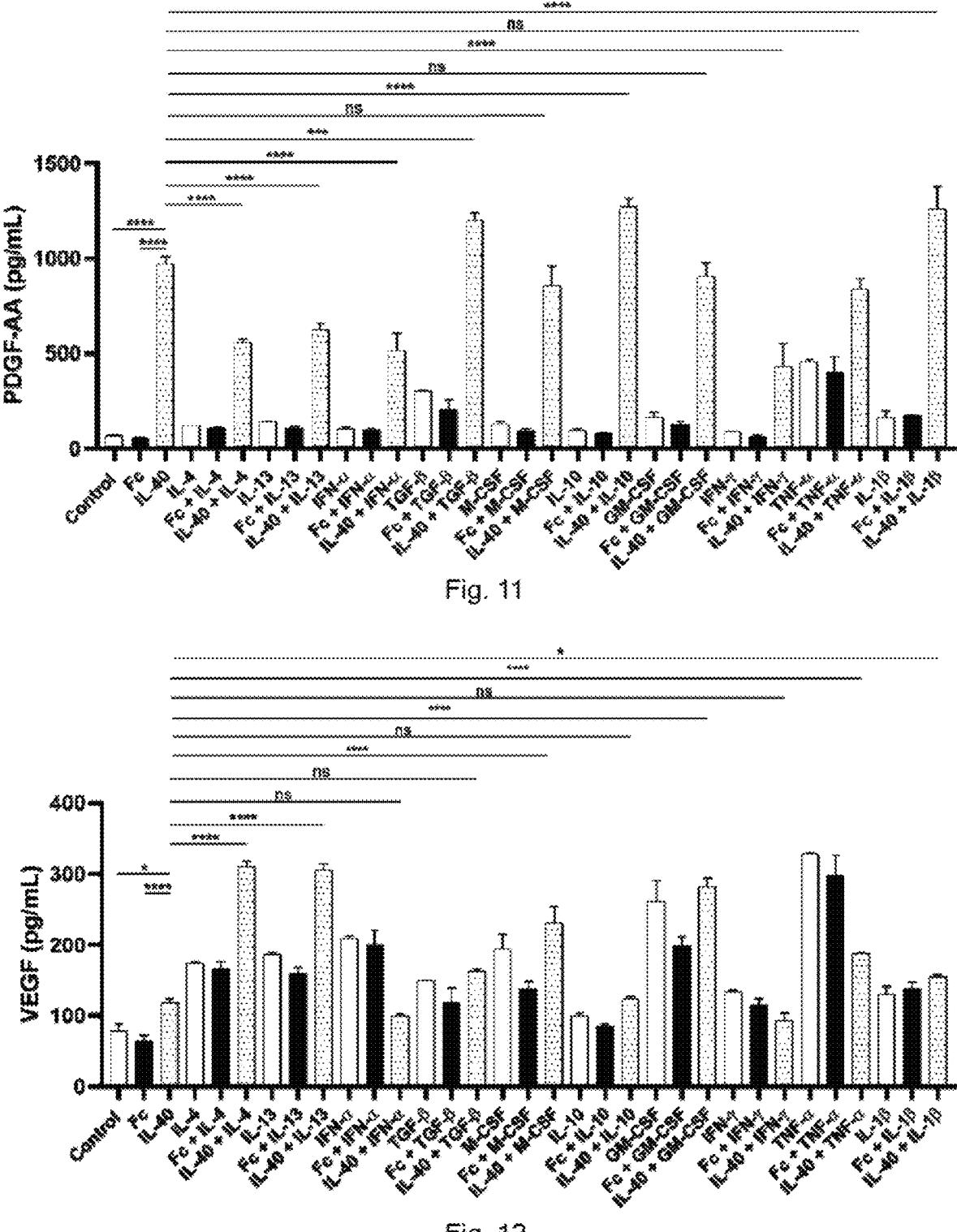
FIG. 11 shows an effect of rhIL40 on the production of PDGF-AA and its activity exacerbation by TGF-β, IL-10, or IL-1β. Results are shown as the media±SEM, and stimuli are represented as follows: control or cytokine (white bars), Fc fraction or Fc fraction+cytokine (black bars), rhIL40 or rhIL40+cytokine (dotted bars).
FIG. 12 shows an effect of rhIL40 on the production of VEGF and its activity exacerbation by IL-4, IL-13, M-CSF, GM-CSF, TNF-α, or IL-1β. Results are shown as the media±SEM, and stimuli are represented as follows: control or cytokine (white bars), Fc fraction or Fc fraction+cytokine (black bars), rhIL40 or rhIL40+cytokine (dotted bars).

The production of PDGF-AA was measured in cell supernatants from THP-1 cells stimulated with different concentrations of the recombinant proteins rhFc or rhIL40 (4.63 μM)±50 ng/mL of IL-4, Il-13, IFN-α, TGF-β, M-CSF, IL-10, GM-CSF, IFN-γ, TNF-α, or IL-1β for 24 hours, and the results are shown in FIG. 11. A significant increase in production of PDGF-AA was observed when stimulating THP-1 cells with rhIL-40, and its production is exacerbated when cells are co-stimulated with rhIL40 plus IFN-γ, TGF-β, IL-10, or IL-1β.

VEGF Production

The production of VEGF was measured in cell supernatants from THP-1 cells stimulated with different concentrations of the recombinant proteins rhFc or rhIL-40 (4.63 μM)±250 ng/mL of IL-4, IL-13, IFN-α, TGF-β, M-CSF, IL-10, GM-CSF, IFN-γ, TNF-α, or IL-1β for 24 hours, and the results are shown in FIG. 12. A significant increase in production of VEGF was observed when stimulating THP-1 cells with rhIL-40, and its production is exacerbated when cells are co-stimulated with rhIL40 plus IL-4, IL-13, M-CSF, GM-CSF, TNF-α, or IL-1β.

Production of Various Cytokines and Chemokines, and Growth Factors

THP-1 Cells

THP-1 cells were stimulated with the recombinant proteins rhFc or rhIL-40 (4.63 μM)±IFN-γ (250 ng/mL), IFN-γ alone or unstimulated (control) for 24 hours. Changes in the production of 23 cytokines, chemokines, or growth factors were evaluated in the supernatant through ELISA or flow cytometry using the multiplex technology (LEGENDplex). Differences were calculated by normalizing the mean value (pg/mL) of each stimulus with the value under control conditions. An increase in the secretion of CCL3, CXCL8, CCL4, CCL2, CXCL10, CCL11, CCL5, IL-1RA, erythropoietin, PDGF-AA, and VEGF was observed when the cells were stimulated with rhIL-40. Significant differences, compared with the rest of stimuli, were found in the secretion of CCL3, CXCL8, CCL4, CCL2, CXCL10, CCL11, CCL5, CXCL9, CXCL1, CXCL11, CXCL5, CCL20, CCL17, IL-1RA, IL-6, erythropoietin, and PDGF-AA when the cells were stimulated with rhIL-40+IFN-γ. IFN-γ and rhFc+IFN-γ also had an impact on several of the evaluated molecules. The results are presented in Table 5 below.

TABLE 5

Effect of rhIL-40, in the presence or absence of IFN-γ, on the production of chemokines and cytokines in THP-1 cells

| Molecule | Control | rhFc | rhIL-40 | IFN-γ | rhFc + IFNγ | rhIL-40 + IFN-γ |
|---|---|---|---|---|---|---|
| CCL3 | 1 | 1 | 41 | 7 | 11 | 362 |
| CXCL8 | 1 | 1 | 9 | 2 | 1 | 78 |
| CCL4 | 1 | 1 | 10 | 6 | 6 | 485 |
| CCL2 | 1 | 2 | 6 | 39 | 41 | 1380 |
| CXCL10 | 1 | 1 | 6 | 974 | 1237 | 3746 |
| CCL11 | 1 | 2 | 5 | 4 | 3 | 31 |
| CCL5 | 1 | 1 | 4 | 1 | 2 | 25 |
| CXCL9 | 1 | 1 | 1 | 78 | 98 | 3249 |
| CXCL1 | 1 | 1 | 1 | 3 | 3 | 390 |
| CXCL11 | 1 | 2 | 1 | 2 | 3 | 26 |
| CXCL5 | 1 | 1 | 1 | 2 | 1 | 8 |
| CCL20 | 1 | 2 | 1 | 2 | 2 | 5 |
| CCL17 | 1 | 1 | 1 | 1 | 1 | 3 |
| IL-1RA | 1 | 1 | 4 | 2 | 2 | 64 |
| IL-6 | 1 | 1 | 1 | 1 | 1 | 14 |
| IL-12p70 | 1 | 1 | 1 | 1 | 1 | 1 |
| IL-12p40 | 1 | 1 | 1 | 1 | 1 | 1 |
| TNF-α | 1 | 1 | 1 | 1 | 1 | 1 |
| IL-4 | 1 | 1 | 1 | 1 | 1 | 1 |
| IL-10 | 1 | 1 | 1 | 1 | 1 | 1 |

TABLE 5-continued

Effect of rhIL-40, in the presence or absence of IFN-γ, on the production of chemokines and cytokines in THP-1 cells

| Molecule | Control | rhFc | rhIL-40 | IFN-γ | rhFc + IFNγ | rhIL-40 + IFN-γ |
|---|---|---|---|---|---|---|
| IL-1β | 1 | 1 | 1 | 1 | 1 | 1 |
| Arginase | 1 | 1 | 1 | 1 | 1 | 1 |
| IL-23 | 1 | 1 | 1 | 1 | 1 | 1 |
| Erythropoietin | 1 | 1 | 20 | 1 | 1 | 48 |
| PDGF-AA | 1 | 1 | 8 | 1 | 1 | 15 |
| VEGF | 1 | 1 | 2 | 2 | 2 | 2 |

PBMCs

Figure 13:
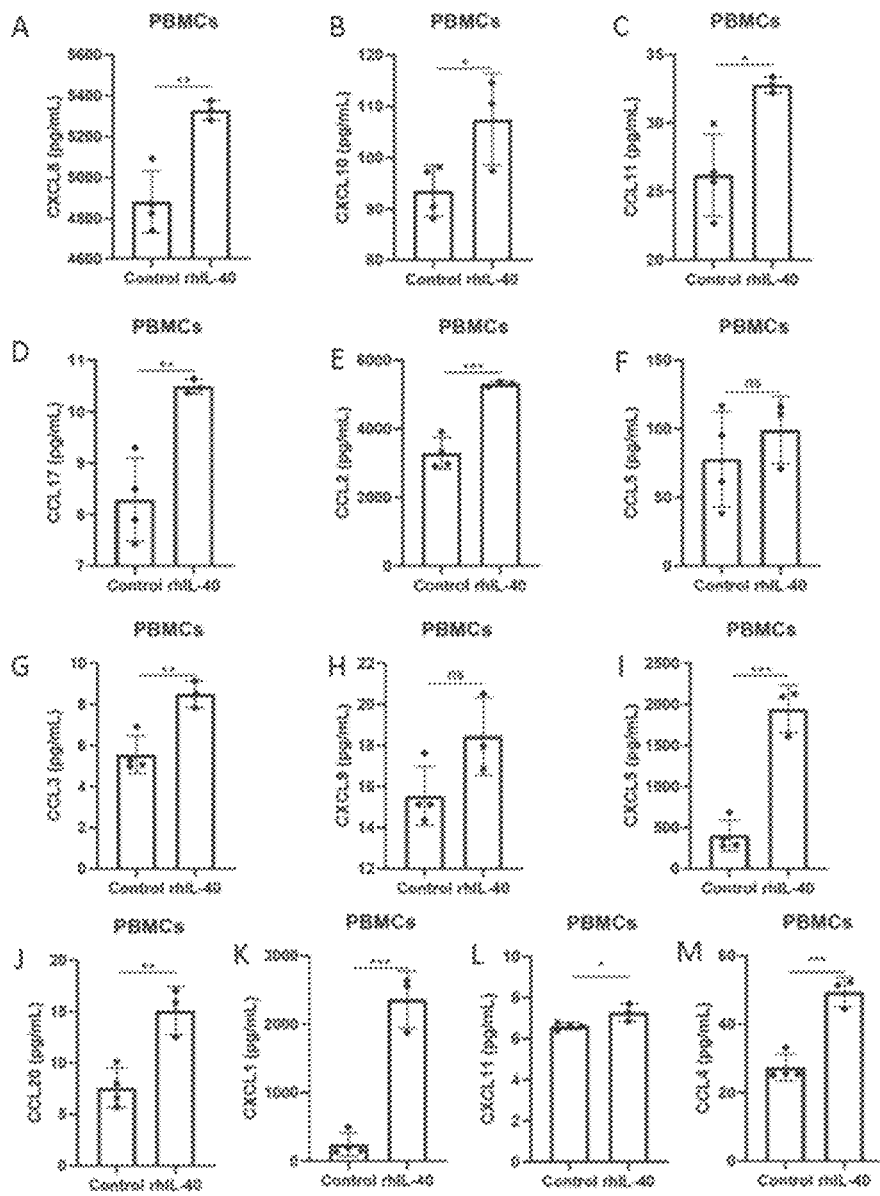
FIG. 13, Panels A-M, shows an effect of rhIL-40 on the production of chemokines in PBMCs. Statistically significant differences in the production of CXCL8 (Panel A), CXCL10 (Panel B), CCL11 (Panel C), CCL17 (Panel D), CCL2 (Panel E), CCL3 (Panel G), CXCL5 (Panel I), CCL20

PBMCs from healthy donor's samples were isolated and stimulated with rhFc or equimolar IL-40 polypeptide concentration for 24 hours, and the results are shown in FIG. 13. Changes in the production of 13 chemokines were evaluated in the supernatant through ELISA or flow cytometry using the multiplex technology (LEGENDplex). Differences were calculated by normalizing the mean value (pg/mL) of each stimulus vs the value under control conditions. A significant increase in the secretion of CXCL1, CXCL5, CXCL8, CCL2, CCL3, CCL4, CCL17 and CCL20 was observed when the cells were stimulated with rhIL-40.

Cell Morphology

Morphological changes in THP-1 cells induced by rhIL-40, in presence or absence of IFN-γ, were observed. THP-1 cells were stimulated with IFN-γ (250 ng/mL) (FIG. 14, panel B), rhFc (2.31 uM) (FIG. 14, panel C), rhFc+IFN-γ (FIG. 14, panel D), rhIL-40 (2.31 uM) (FIG. 14, panel E), rhIL-40+IFN-γ (FIG. 14, panel F) or unstimulated (FIG. 14, panel A) for 24 hours. Morphological changes were documented through light microscopy (Keyence BZ-X700) in a phase contrast mode (magnification10×). The percentage of cells with a morphological change was calculated counting the cells and using the following formula: (# of cells attached to the plate×100%)/total cell number. Differences in the cell shape and attachment to the plate were observed in FIG. 14, panel B (13%), FIG. 14, panel E (10%), and FIG. 14, panel F (35%). IFN-γ and IL-40 showed a synergistic effect. No changes in cell morphology were observed in FIG. 14, panel A, or FIG. 14, panel C.

Similarly, morphological changes in THP-1 cells induced by rhIL-40, in presence of IFN-γ were observed under co-stimulation with IL-10, TNF-α, and IL-1β. THP-1 cells were stimulated with each cytokine (50 ng/mL), rhFc (2.31 uM), rhFc+each cytokine, rhIL-40 (2.31 uM), rhIL-40+each cytokine or unstimulated cells for 24 hours. Morphological changes were documented through light microscopy (Keyence BZ-X700) in a phase contrast mode (magnification 10×). The number of macrophages/field is the average of 4 different fields under same conditions.

Cell Surface Molecules

THP-1 cells were stimulated with rhFc, rhIL-40, IFN-γ, IFN-γ+rhFc or IFN-γ+rh-IL-40, and the results are shown in FIG. 15. Stimulation of rhIL40 plus a co-stimulatory cytokine as IFN-γ induces the overexpression of co-stimulatory proteins as HLA-A, B, C (Panel A), CD40 (Panel B), and CD11b (Panel C).

Identification of IL-40 Receptor

IL-40 receptor expression was observed in THP-1 cells and CD11b+ cells from a healthy donor, and the results are shown in FIG. 16. Positive cells were identified incubating cells with the rhIL-40 polypeptide coupled to Fc tag for 30 minutes at 4° C., followed by incubation with a secondary antibody anti-tag couple to APC fluorophore for 15 min at 4° C., followed by flow cytometry analysis.

Example 2: Examples of Amino Acid and Nucleic
Acid Sequences

TABLE 6

| | | |
|---|---|---|
| | | amino acid sequences and nucleic acid sequences |

| Type | SEQ ID NO | Sequence |
|---|---|---|
| Human IL-40 amino acid sequence | 1 | MGLPGLFCLAVLAASSFSKAREEEITPVVSIAYKVLEVFPKGRWVLITCCAPQPP<br>PPITYSLCGTKNIKVAKKVVKTHEPASFNLNVTLKSSPDLLTYFCWASSTSGAHV<br>DSARLQMHVVELWSKPVSELRANFTLQDRGAGPRVEMICQASSGSPPITNSLIG<br>KDGQVHLQQRPCHRQPANFSFLPSQTSDWFWCQAANNANVQHSALTVVPPG<br>GDQKMEDWQGPLESPILALPLYRSTRRLSEEEFGGFRIGNGEVRGRKAAAM |
| Human IL-40 nucleic acid sequence (coding region underlined) | 2 | GCCAGGAACTAGGAGGTTCTCACTGCCCGAGCAGAGGCCCTACACCCACC<br>GAGGCATGGGGCTCCCTGGGCTGTTCTGCTTGGCCGTGCTGGCTGCCAGC<br>AGCTTCTCCAAGGCACGGGAGGAAGAAATTACCCCTGTGGTCTCCATTGCC<br>TACAAAGTCCTGGAAGTTTTCCCCAAAGGCCGCTGGGTGCTCATAACCTGC<br>TGTGCACCCCAGCCACCACCGCCCATCACCTATTCCCTCTGTGGAACCAAG<br>AACATCAAGGTGGCCAAGAAGGTGGTGAAGACCCACGAGCCGGCCTCCTT<br>CAACCTCAACGTCACACTCAAGTCCAGTCCAGACCTGCTCACCTACTTCTGC<br>TGGGCGTCCTCCACCTCAGGTGCCCATGTGGACAGTGCCAGGCTACAGAT<br>GCACTGGGAGCTGTGGTCCAAGCCAGTGTCTGAGCTGCGGGCAACTTCA<br>CTCTGCAGGACAGAGGGGCAGGCCCCAGGGTGGAGATGATCTGCCAGGC<br>GTCCTCGGGCAGCCCACCTATCACCAACAGCCTGATCGGGAAGGATGGGC<br>AGGTCCACCTGCAGCAGAGACCATGCCACAGGCAGCCTGCCAACTTCTCCT<br>TCCTGCCGAGCCAGACATCGGACTGGTTCTGGTGCCAGGCTGCAAACAAC<br>GCCAATGTCCAGCACAGCGCCCTCACAGTGGTGCCCCCAGGTGGTGACCA<br>GAAGATGGAGGACTGGCAGGGTCCCCTGGAGAGCCCCATCCTTGCCTTGC<br>CGCTCTACAGGAGCACCCGCCGTCTGAGTGAAGAGGAGTTTGGGGGGTTC<br>AGGATAGGGAATGGGGAGGTCAGAGGACGCAAAGCAGCAGCCATGTAGAA<br>TGAACCGTCCAGAGAGCCAAGCACGGCAGAGGACTGCAGGCCATCAGCGT<br>GCACTGTTCGTATTTGGAGTTCATGCAAAATGAGTGTGTTTTAGCTGCTCTT<br>GCCACAAAAAAAAAAAAAAAAAAAAAAAGGGTAACTATGAGAGATGGTGGATA<br>TGTTAACTTGCTTCGCTATAGGAACCTTTGTGCTATCTATATTATCTATATGA<br>ATCCCATCATATCAGGTTGTCTACCTTA |
| Mouse IL-40 amino acid sequence | 3 | MALLQLLLLFAMLAACGFSEEQTEGITIAYKVLEVYPQSRRVLITCDAPEASQPITY<br>SLLASRGILVAKKVVHDSVPASFNINITIKSSPDLLTYSCQATSNSGTYGPSSRLQ<br>MYQELWAKPVSQLQADFVLRHGDSGPTVELSCLASSGSPPITYRLVGNGGRVL<br>AQQRPLHGKPANFSLPLSQTTGWFQCEAENDVGVDSSARIPLPRAEARAKLVT<br>TLAGELPLTPTCILAGSLVSIAVIASRMLSSTGL |
| Mouse IL-40 nucleic acid sequence (coding region underlined) | 4 | TAGCTGCAGGCAGCCACCCGAGGAGCATCCAGGGGCCTTGGGGTGGAGA<br>GGCCAGACAGGAAGCTTTGGACAGCCTGAGCCATACACAGCCCCAACCTC<br>ACAGACGCATGGCGCTCCTTCAGCTGCTCCTCTTTGCCATGCTGGCTGCCT<br>GTGGCTTCTCAGAGGAGCAGACAGAAGGCATCACCATTGCCTACAAAGTAC<br>TGGAAGTTTATCCCCAAAGCCGGAGGGTGCTTATAACCTGCGATGCCCCTG<br>AGGCGTCCCAGCCCATCACATACTCTCTCCTGGCTAGCCGAGGTATCCTGG<br>TGGCAAAAAAGGTTGTGCATGACTCCGTGCCGGCCTCCTTCAACATCAATAT<br>CACCATCAAGTCCAGCCCAGACCTGCTCACCTACTCCTGCCAGGCAACCTC<br>GAACTCTGGCACCTATGGACCCAGCAGCAGGCTCCAGATGTACCAGGAACT<br>GTGGGCTAAGCCAGTGTCTCAGCTGCAGGCTGACTTCGTCCTACGCCATGG<br>GGACTCGGGCCCCACTGTGGAGCTGTCCTGCCTGGCATCCTCAGGCAGCC<br>CCCCCATCACCTACCGCTTGGTGGGGAATGGTGGGCGTGTTCTTGCACAG<br>CAAAGGCCACTTCATGGAAAACCAGCCAACTTCTCCCTCCCGCTGTCCCAG<br>ACCACTGGTTGGTTCCAGTGCGAAGCTGAAAACGATGTCGGTGTGGACAGC<br>AGTGCCCGCATCCCGCTGCCCCGAGCAGAGGCCCGAGCCAAGCTGGTGAC<br>CACCCTCGCAGGGGAGCTGCCCCTGACACCCACCTGTATTCTGGCTGGCA<br>GCCTCGTCTCCATAGCCGTTATTGCTTCCAGGATGCTGAGCTCGACCGGGT<br>TGTGACCGGAAGACAGAGCCATGGGCTTGCCTCCCTGCCCTGTACAAGAAC<br>CCACCAATGGAGCAAAAGAGAGCCTGAGGTGTGGGGGTAGAAAAGGGGGG<br>TTCAGGGCTGGAGAGATGGCTCAGTTACAGCACTGACTGTTCTTCCAGAGG<br>TCCCGAGTTCAATTCCCATAATGTACTTCTACACATAAAATAAATAATTCTTTT<br>TTTGTTTTGTT |
| Human IFN-γ amino acid sequence | 5 | MKYTSYILAFQLCIVLGSLGCYCQDPYVKEAENLKKYFNAGHSDVADNGTLFLGI<br>LKNWKEESDRKIMQSQIVSFYFKLFKNFKDDQSIQKSVETIKEDMNVKFFNSNK<br>KKRDDFEKLTNYSVTDLNVQRKAIHELIQVMAELSPAAKTGKRKRSQMLFRGR<br>RASQ |
| Human IFN-γ nucleic acid sequence (coding region underlined) | 6 | ACATTGTTCTGATCATCTGAAGATCAGCTATTAGAAGAGAAAGATCAGTTAA<br>GTCCTTTGGACCTGATCAGCTTGATACAAGAACTACTGATTTCAACTTCTTTG<br>GCTTAATTCTCTCGGAAACGATGAAATATACAAGTTATATCTTGGCTTTTCAG<br>CTCTGCATCGTTTTGGGTTCTCTTGGCTGTTACTGCCAGGACCCCATATGTAA<br>AGAAGCAGAAAACCTTAAGAAATATTTTAATGCAGGTCATTCAGATGTAGC<br>GGATAATGGAACTCTTTTCTTAGGCATTTTGAAGAATTGGAAAGAGGAGAGT<br>GACAGAAAAATAATGCAGAGCCAAATTGTCTCCTTTTACTTCAAACTTTTTAA<br>AAACTTTAAAGATGACCAGAGCATCCAAAAGAGTGTGGAGACCATCAAGGA<br>AGACATGAATGTCAAGTTTTTCAATAGCAACAAAAAGAAACGAGATGACTTC |

| Type | SEQ ID NO | Sequence |
|------|-----------|----------|
| | | GAAAAGCTGACTAATTATTCGGTAACTGACTTGAATGTCCAACGCAAAGCAA |
| | | TACATGAACTCATCCAAGTGATGGCTGAACTGTCGCCAGCAGCTAAAACAG |
| | | GGAAGCGAAAAAGGAGTCAGATGCTGTTTCGAGGTCGAAGAGCATCCCAGT |
| | | AATGGTTGTCCTGCCTGCAATATTTGAATTTTAAATCTAAATCTATTTATTAAT |
| | | ATTTAACATTATTTATATGGGGAATATATTTTTAGACTCATCAATCAAATAAGT |
| | | ATTTATAATAGCAACTTTTGTGTAATGAAAATGAATATCTATTAATATATGTAT |
| | | TATTTATAATTCCTATATCCTGTGACTGTCTCACTTAATCCTTTGTTTTCTGAC |
| | | TAATTAGGCAAGGCTATGTGATTACAAGGCTTTATCTCAGGGGCCAACTAGG |
| | | CAGCCAACCTAAGCAAGATCCCATGGGTTGTGTGTTTATTTCACTTGATGAT |
| | | ACAATGAACACTTATAAGTGAAGTGATACTATCCAGTTACTGCCGGTTTGAA |
| | | AATATGCCTGCAATCTGAGCCAGTGCTTTAATGGCATGTCAGACAGAACTTG |
| | | AATGTGTCAGGTGACCCTGATGAAAACATAGCATCTCAGGAGATTTCATGCC |
| | | TGGTGCTTCCAAATATTGTTGACAACTGTGACTGTACCCAAATGGAAAGTAA |
| | | CTCATTTGTTAAAATTATCAATATCTAATATATATGAATAAAGTGTAAGTTCAC |
| | | AACTA |
| Mouse IFN-γ amino acid sequence | 7 | MNATHCILALQLFLMAVSGCYCHGTVIESLESLNNYFNSSGIDVEEKSLFLDIWR NWQKDGDMKILQSQIISFYLRLFEVLKDNQAISNNISVIESHLITTFFSNSKAKKD AFMSIAKFEVNNPQVQRQAFNELIRVVHQLLPESSLRKRKRSRC |
| Mouse IFN-γ nucleic acid sequence (coding region underlined) | 8 | TATAGCTGCCATCGGCTGACCTAGAGAAGACACATCAGCTGATCCTTTGGA CCCTCTGACTTGAGACAGAAGTTCTGGGCTTCTCCTCCTGCGGCCTAGCTC TGAGACAATGAACGCTACACACTGCATCTTGGCTTTGCAGCTCTTCCTCATG GCTGTTTCTGGCTGTTACTGCCACGGCACAGTCATTGAAAGCCTAGAAAGT CTGAATAACTATTTTAACTCAAGTGGCATAGATGTGGAAGAAAAGAGTCTCT TCTTGGATATCTGGAGGAACTGGCAAAAGGATGGTGACATGAAAATCCTGC AGAGCCAGATTATCTCTTTCTACCTCAGACTCTTTGAAGTCTTGAAAGACAAT CAGGCCATCAGCAACAACATAAGCGTCATTGAATCACACCTGATTACTACCT TCTTCAGCAACAGCAAGGCGAAAAAGGATGCATTCATGAGTATTGCCAAGTT TGAGGTCAACAACCCACAGGTCCAGCGCCAAGCATTCAATGAGCTCATCCG AGTGGTCCACCAGCTGTTGCCGGAATCCAGCCTCAGGAAGCGGAAAAGGA GTCGCTGCTGATTCGGGGTGGGGAAGAGATTGTCCCAATAAGAATAATTCT GCCAGCACTATTTGAATTTTTAAATCTAAACCTATTTATTAATATTTAAAACTA TTTATATGGAGAATCTATTTTAGATGCATCAACCAAAGAAGTATTTATAGTAA CAACTTATATGTGATAAGAGTGAATTCCTATTAATATATGTGTTATTTTATAATT TCTGTCTCCTCAACTATTTCTCTTTGACCAATTAATTATTCTTTCTGACTAATT AGCCAAGACTGTGATTGCGGGGTTGTATCTGGGGGTGGGGGACAGCCAAG CGGCTGACTGAACTCAGATTGTAGCTTGTACCTTTACTTCACTGACCAATAA GAAACATTCAGAGCTGCAGTGACCCCGGGAGGTGCTGCTGATGGGAGGAG ATGTCTACACTCCGGGCCAGCGCTTTAACAGCAGGCCAGACAGCACTCGAA TGTGTCAGGTAGTAACAGGCTGTCCCTGAAAGAAAGCAGTGTCTCAAGAGA CTTGACACCTGGTGCTTCCCTATACAGCTGAAAACTGTGACTACACCCGAAT GACAAATAACTCGCTCATTTATAGTTTATCACTGTCTAATTGCATATGAATA AAGTATACCTTTGCAACCAA |
| rh IL-40-Fc amino acid sequence | 9 | LAREEEITPVVSIAYKVLEVFPKGRWVLITCCAPQPPPPITYSLCGTKNIKVAKKV VKTHEPASFNLNVTLKSSPDLLTYFCRASSTSGAHVDSARLQMHWELWSKPVS ELRANFTLQDRGAGPRVEMICQASSGSPPITNSLIGKDGQVHLQQRPCHRQPA NFSFLPSQTSDWFWCQAANNANVQHSALTVVPPGGDQKMEDWQGPLESPILA LPLYRSTRRLSEEEFGGFRIGNGEVRGRKAAAMSRIEGRMDPKSCDKTHTCPP CPAPELLGGPSVFLFPPKPKDTLMISRTPEVTCVVVDVSHEDPEVKFNWYVDG VEVHNAKTKPREEQYNSTYRVVSVLTVLHQDWLNGKEYKCKVSNKALPAPIEK TISKAKGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYTQKS LSLSPGK |
| rh IL-40-Fc nucleic acid sequence | 10 | ATGCCCCTGCTGCTGCTGCTGCCCCTGCTGTGGGCCGGCGCCCTGGCCCT GGCTCGGGAGGAAGAAATTACCCCTGTGGTCTCCATTGCCTACAAAGTCCT GGAAGTTTTCCCCAAAGGCCGCTGGGTGCTCATAACCTGCTGTGCACCCCA GCCACCACCGCCCATCACCTATTCCCTCTGTGGAACCAAGAACATCAAGGT GGCCAAGAAGGTGGTGAAGACCCACGAGCCGGCCTCCTTCAACCTCAACG TCACACTCAAGTCCAGTCCAGACCTGCTCACCTACTTCTGCCGGGCGTCCT CCACCTCAGGTGCCCATGTGGACAGTGCCAGGCTACAGATGCACTGGGAG CTGTGGTCCAAGCCAGTGTCTGAGCTGCGGGCCAACTTCACTCTGCAGGAC AGAGGGGCAGGCCCCAGGGTGGAGATGATCTGCCAGGCGTCCTCGGGCA GCCCACCTATCACCAACAGCCTGATCGGGAAGGATGGGCAGGTCCACCTG CAGCAGAGACCCATGCCACAGGCAGCCTGCCAACTTCTCCTTCCTGCCGAGC CAGACATCGGACTGGTTCTGGTGCCAGGCTGCAAACAACGCCAATGTCCAG CACAGCGCCCTCACAGTGGTGCCCCCAGGTGGTGACCAGAAGATGGAGGA CTGGCAGGGTCCCCTGGAGAGCCCCATCCTTGCCTTGCCGCTCTACAGGA GCACCCGCCGTCTGAGTGAAGAGGAGTTTGGGGGGTTCAGGATAGGGAAT GGGGAGGTCAGAGGACGCAAAGCAGCAGCCATGTCTAGAATCGAGGGCCG GATGGACCCCAAGTCCTGCGACAAGACTCACACATGCCCACCGTGCCCAG CACCTGAACTCCTGGGGGGACCGTCAGTCTTCCTCTTCCCCCCAAAACCCA AGGACACCCTCATGATCTCCCGGACCCCTGAGGTCACATGCGTGGTGGTG |

TABLE 6-continued

| | | |
|---|---|---| amino acid sequences and nucleic acid sequences

| Type | SEQ ID NO | Sequence |
|---|---|---|
| | | GACGTGAGCCACGAAGACCCTGAGGTCAAGTTCAACTGGTACGTGGACGG<br>CGTGGAGGTGCATAATGCCAAGACAAAGCCGCGGGAGGAGCAGTACAACA<br>GCACGTACCGTGTGGTCAGCGTCCTCACCGTCCTGCACCAGGACTGGCTG<br>AATGGCAAGGAGTACAAGTGCAAGGTCTCCAACAAAGCCCTCCCAGCCCCC<br>ATCGAGAAAACCATCTCCAAAGCCAAAGGGCAGCCCCGAGAACCACAGGT<br>GTACACCCTGCCCCCATCCCGGGATGAGCTGACCAAGAACCAGGTCAGCC<br>TGACCTGCCTGGTCAAAGGCTTCTATCCCAGCGACATCGCCGTGGAGTGG<br>GAGAGCAATGGGCAGCCGGAGAACAACTACAAGACCACGCCTCCCGTGTT<br>GGACTCCGACGGCTCCTTCTTCCTCTACAGCAAGCTCACCGTGGACAAGAG<br>CAGGTGGCAGCAGGGGAACGTCTTCTCATGCTCCGTGATGCATGAGGCTCT<br>GCACAACCACTACACGCAGAAGAGCCTCTCCCTGTCTCCCGGGAAATAATA<br>A |
| rh IgG1 constant region | 11 | ASTKGPSVFP LAPSSKSTSG GTAALGCLVK DYFPEPVTVS VVNSGALTSGV<br>HTFPAVLQSS GLYSLSSVVT VPSSSLGTQT YICNVNHKPS NTKVDKKVEP<br>KSCDKTHTCP PCPAPELLGG PSVFLFPPKP KDTLMISRTP EVTCVVVDVS<br>HEDPEVKFNW YVDGVEVHNA KTKPREEQYN STYRVVSVLT<br>VLHQDWLNGK EYKCKVSNKA LPAPIEKTIS KAKGQPREPQ VYTLPPSRDE<br>LTKNQVSLTC LVKGFYPSDI AVEWESNGQP ENNYKTTPPV LDSDGSFFLY<br>SKLTVDKSRW QQGNVFSCSV MHEALHNHYT QKSLSLSPGK |
| Human IL-4 amino acid sequence | 12 | MGLTSQLLPPLFFLLACAGNFVHGHKCDITLQEIIKTLNSLTEQKTLCTELTVTDIF<br>AASKNTTEKETFCRAATVLRQFYSHHEKDTRCLGATAQQFHRHKQLIRFLKRLD<br>RNLWGLAGLNSCPVKEANQSTLENFLERLKTIMREKYSKCSS |
| Human IL-4 nucleic acid sequence | 13 | ATGGGTCTCACCTCCCAACTGCTTCCCCCTCTGTTCTTCCTGCTAGCATGTG<br>CCGGCAACTTTGTCCACGGACACAAGTGCGATATCACCTTACAGGAGATCA<br>TCAAAACTTTGAACAGCCTCACAGAGCAGAAGACTCTGTGCACCGAGTTGA<br>CCGTAACAGACATCTTTGCTGCCTCCAAGAACACAACTGAGAAGGAAACCTT<br>CTGCAGGGCTGCGACTGTGCTCCGGCAGTTCTACAGCCACCATGAGAAGG<br>ACACTCGCTGCCTGGGTGCGACTGCACAGCAGTTCCACAGGCACAAGCAG<br>CTGATCCGATTCCTGAAACGGCTCGACAGGAACCTCTGGGGCCTGGCGGG<br>CTTGAATTCCTGTCCTGTGAAGGAAGCCAACCAGAGTACGTTGGAAAACTTC<br>TTGGAAAGGCTAAAGACGATCATGAGAGAGAAATATTCAAAGTGTTCGAGCT<br>GA |
| Mouse IL-4 amino acid sequence | 14 | MGLNPQLVVILLFFLECTRSHIHGCDKNHLREIIGILNEVTGEGTPCTEMDVPNVL<br>TATKNTTESELVCRASKVLRIFYLKHGKTPCLKKNSSVLMELQRLFRAFRCLDS<br>SISCTMNESKSTSLKDFLESLKSIMQMDYS |
| Mouse IL-4 nucleic acid sequence | 15 | ATGGGTCTCAACCCCCAGCTAGTTGTCATCCTGCTCTTCTTTCTCGAATGTA<br>CCAGGAGCCATATCCACGGATGCGACAAAAATCACTTGAGAGAGATCATCG<br>GCATTTTGAACGAGGTCACAGGAGAAGGGACGCCATGCACGGAGATGGAT<br>GTGCCAAACGTCCTCACAGCAACGAAGAACACCACAGAGAGTGAGCTCGTC<br>TGTAGGGCTTCCAAGGTGCTTCGCATATTTTATTTAAAACATGGGAAAACTC<br>CATGCTTGAAGAAGAACTCTAGTGTTCTCATGGAGCTGCAGAGACTCTTTCG<br>GGCTTTTCGATGCCTGGATTCATCGATAAGCTGCACCATGAATGAGTCCAA<br>GTCCACATCACTGAAAGACTTCCTGGAAAGCCTAAAGAGCATCATGCAAATG<br>GATTACTCGTAG |
| Human IL-10 amino acid sequence | 16 | MHSSALLCCLVLLTGVRASPGQGTQSENSCTHFPGNLPNMLRDLRDAFSRVKT<br>FFQMKDQLDNLLLKESLLEDFKGYLGCQALSEMIQFYLEEVMPQAENQDPDIKA<br>HVNSLGENLKTLRLRLRRCHRFLPCENKSKAVEQVKNAFNKLQEKGIYKAMSE<br>FDIFINYIEAYMTMKIRN |
| Human IL-10 nucleic acid sequence | 17 | ATGCACAGCTCAGCACTGCTCTGTTGCCTGGTCCTCCTGACTGGGGTGAGG<br>GCCAGCCCAGGCCAGGGCACCCAGTCTGAGAACAGCTGCACCCACTTCCC<br>AGGCAACCTGCCTAACATGCTTCGAGATCTCCGAGATGCCTTCAGCAGAGT<br>GAAGACTTTCTTTCAAATGAAGGATCAGCTGGACAACTTGTTGTTAAAGGAG<br>TCCTTGCTGGAGGACTTTAAGGGTTACCTGGGTTGCCAAGCCTTGTCTGAG<br>ATGATCCAGTTTTACCTGGAGGAGGTGATGCCCCAAGCTGAGAACCAAGAC<br>CCAGACATCAAGGCGCATGTGAACTCCCTGGGGGAGAACCTGAAGACCCT<br>CAGGCTGAGGCTACGGCGCTGTCATCGATTTCTTCCCTGTGAAAACAAGAG<br>CAAGGCCGTGGAGCAGGTGAAGAATGCCTTTAATAAGCTCCAAGAGAAAGG<br>CATCTACAAAGCCATGAGTGAGTTTGACATCTTCATCAACTACATAGAAGCC<br>TACATGACAATGAAGATACGAAACTGA |
| Mouse IL-10 amino acid sequence | 18 | MPGSALLCCLLLLTGMRISRGQYSREDNNCTHFPVGQSHMLLELRTAFSQVKT<br>FFQTKDQLDNILLTDSLMQDFKGYLGCQALSEMIQFYLVEVMPQAEKHGPEIKE<br>HLNSLGEKLKTLRMRLRRCHRFLPCENKSKAVEQVKSDFNKLQDQGVYKAMN<br>EFDIFINCIEAYMMIKMKS |

TABLE 6-continued amino acid sequences and nucleic acid sequences

| Type | SEQ ID NO | Sequence |
|------|-----------|----------|
| Mouse IL-10 nucleic acid sequence | 19 | ATGCCTGGCTCAGCACTGCTATGCTGCCTGCTCTTACTGACTGGCATGAGG<br>ATCAGCAGGGGCCAGTACAGCCGGGAAGACAATAACTGCACCCACTTCCCA<br>GTCGGCCAGAGCCACATGCTCCTAGAGCTGCGGACTGCCTTCAGCCAGGT<br>GAAGACTTTCTTTCAAACAAAGGACCAGCTGGACAACATACTGCTAACCGAC<br>TCCTTAATGCAGGACTTTAAGGGTTACTTGGGTTGCCAAGCCTTATCGGAAA<br>TGATCCAGTTTTACCTGGTAGAAGTGATGCCCCAGGCAGAGAAGCATGGCC<br>CAGAAATCAAGGAGCATTTGAATTCCCTGGGTGAGAAGCTGAAGACCCTCA<br>GGATGCGGCTGAGGCGCTGTCATCGATTTCTCCCCTGTGAAAATAAGAGCA<br>AGGCAGTGGAGCAGGTGAAGAGTGATTTTAATAAGCTCCAAGACCAAGGTG<br>TCTACAAGGCCATGAATGAATTTGACATCTTCATCAACTGCATAGAAGCATA<br>CATGATGATCAAAATGAAAAGCTAA |
| Human TGF-β amino acid sequence | 20 | MPPSGLRLLPLLLPLLWLLVLTPGRPAAGLSTCKTIDMELVKRKRIEAIRGQILSK<br>LRLASPPSQGEVPPGPLPEAVLALYNSTRDRVAGESAEPEPEPEADYYAKEVT<br>RVLMVETHNEIYDKFKQSTHSIYMFFNTSELREAVPEPVLLSRAELRLLRLKLKV<br>EQHVELYQKYSNNSWRYLSNRLLAPSDSPEWLSFDVTGVVRQWLSRGGEIEG<br>FRLSAHCSCDSRDNTLQVDINGFTTGRRGDLATIHGMNRPFLLLMATPLERAQ<br>HLQSSRHRRALDTNYCFSSTEKNCCVRQLYIDFRKDLGVVKWIHEPKGYHANFC<br>LGPCPYIWSLDTQYSKVLALYNQHNPGASAAPCCVPQALEPLPIVYYVGRKPKV<br>EQLSNMIVRSCKCS |
| Human TGF-β nucleic acid sequence | 21 | ATGCCGCCCTCCGGGCTGCGGCTGCTGCCGCTGCTGCTACCGCTGCTGTG<br>GCTACTGGTGCTGACGCCTGGCCGGCCGGCCGCGGGACTATCCACCTGCA<br>AGACTATCGACATGGAGCTGGTGAAGCGGAAGCGCATCGAGGCCCATCCGC<br>GGCCAGATCCTGTCCAAGCTGCGGCTCGCCAGCCCCCCGAGCCAGGGGG<br>AGGTGCCGCCCGGCCCGCTGCCCGAGGCCGTGCTCGCCCTGTACAACAG<br>CACCCGCGACCGGGTGGCCGGGGAGAGTGCAGAACCGGAGCCCGAGCCT<br>GAGGCCGACTACTACGCCAAGGAGGTCACCCGCGTGCTAATGGTGGAAAC<br>CCACAACGAAATCTATGACAAGTTCAAGCAGAGTACACACAGCATATATATG<br>TTCTTCAACACATCAGAGCTCCGAGAAGCGGTACCTGAACCCGTGTTGCTC<br>TCCCGGGCAGAGCTGCGTCTGCTGAGGCTCAAGTTAAAAGTGGAGCAGCA<br>CGTGGAGCTGTACCAGAAATACAGCAACAATTCCTGGCGATACCTCAGCAA<br>CCGGCTGCTGGCACCCAGCGACTCGCCAGAGTGGTTATCTTTTGATGTCAC<br>CGGAGTTGTGCGGCAGTGGTTGAGCCGTGGAGGGGAAATTGAGGGCTTTC<br>GCCTTAGCGCCCACTGCTCCTGTGACAGCAGGGATAACACACTGCAAGTGG<br>ACATCAACGGGTTCACTACCGGCCGCCGAGGTGACCTGGCCACCATTCATG<br>GCATGAACCGGCCTTTCCTGCTTCTCATGGCCACCCCGCTGGAGAGGGCC<br>CAGCATCTGCAAAGCTCCCGGCACCGCCGAGCCCTGGACACCAACTATTG<br>CTTCAGCTCCACGGAGAAGAACTGCTGCGTGCGGCAGCTGTACATTGACTT<br>CCGCAAGGACCTCGGCTGGAAGTGGATCCACGAGCCCAAGGGCTACCATG<br>CCAACTTCTGCCTCGGGCCCTGCCCCTACATTTGGAGCCTGGACACGCAGT<br>ACAGCAAGGTCCTGGCCCTGTACAACCAGCATAACCCGGGCGCCTCGGCG<br>GCGCCGTGCTGCGTGCCGCAGGCGCTGGAGCCGCTGCCCATCGTGTACTA<br>CGTGGGCCGCAAGCCCAAGGTGGAGCAGCTGTCCAACATGATCGTGCGCT<br>CCTGCAAGTGCAGCTGA |
| Mouse TGF-β amino acid sequence | 22 | MPPSGLRLLPLLLPLPWLLVLTPGRPAAGLSTCKTIDMELVKRKRIEAIRGQILSK<br>LRLASPPSQGEVPPGPLPEAVLALYNSTRDRVAGESADPEPEPEADYYAKEVT<br>RVLMVDRNNAIYEKTKDISHSIYMFFNTSDIREAVPEPPLLSRAELRLQRLKSSV<br>EQHVELYQKYSNNSWRYLGNRLLTPTDTPEWLSFDVTGVVRQWLNQGDGIQG<br>FRFSAHCSCDSKDNKLHVEINGISPKRRGDLGTIHDMNRPFLLLMATPLERAQH<br>LHSSRHRRALDTNYCFSSTEKNCCVRQLYIDFRKDLGWKWIHEPKGYHANFCL<br>GPCPYIWSLDTQYSKVLALYNQHNPGASASPCCVPQALEPLPIVYYVGRKPKV<br>EQLSNMIVRSCKCS |
| Mouse TGF-β nucleic acid sequence | 23 | ATGCCGCCCTCGGGGCTGCGGCTACTGCCGCTTCTGCTCCCACTCCCGTG<br>GCTTCTAGTGCTGACGCCCGGGAGGCCAGCCGCGGGACTCTCCACCTGCA<br>AGACCATCGACATGGAGCTGGTGAAACGGAAGCGCATCGAAGCCATCCGT<br>GGCCAGATCCTGTCCAAACTAAGGCTCGCCAGTCCCCCAAGCCAGGGGGA<br>GGTACCGCCCGGCCCGCTGCCCGAGGCGGTGCTCGCTTTGTACAACAGCA<br>CCCGCGACCGGGTGGCAGGCGAGAGCGCCGACCCAGAGCCGGAGCCCGA<br>AGCGGACTACTATGCTAAAGAGGTCACCCGCGTGCTAATGGTGGACCGCAA<br>CAACGCCATCTATGAGAAAACCAAAGACATCTCACACAGTATATATATGTTC<br>TTCAATACGTCAGACATTCGGGAAGCAGTGCCCGAACCCCCATTGCTGTCC<br>CGTGCAGAGCTGCGCTTGCAGAGATTAAAATCAAGTGTGGAGCAACATGTG<br>GAACTCTACCAGAAATATAGCAACAATTCCTGGCGTTACCTTGGTAACCGGC<br>TGCTGACCCCCACTGATACGCCTGAGTGGCTGTCTTTTGACGTCACTGGAG<br>TTGTACGGCAGTGGCTGAACCAAGGAGACGGAATACAGGGCTTTCGATTCA<br>GCGCTCACTGCTCTTGTGACAGCAAAGATAACAAACTCCACGTGGAAATCA<br>ACGGGATCAGCCCCAAACGTCGGGGCGACCTGGGCACCATCCATGACATG<br>AACCGGCCCTTCCTGCTCCTCATGGCCACCCCCCTGGAAAGGGCCCAGCA<br>CCTGCACAGCTCACGGCACCGGAGAGCCCTGGATACCAACTATTGCTTCAG<br>CTCCACAGAGAAGAACTGCTGTGTGCGGCAGCTGTACATTGACTTTAGGAA<br>GGACCTGGGTTGGAAGTGGATCCACGAGCCCAAGGGCTACCATGCCAACT |

TABLE 6-continued

| | amino acid sequences and nucleic acid sequences | |
|---|---|---|
| Type | SEQ ID NO | Sequence |

| | | TCTGTCTGGGACCCTGCCCCTATATTTGGAGCCTGGACACACAGTACAGCA AGGTCCTTGCCCTCTACAACCAACACAACCCGGGCGCTTCGGCGTCACCGT GCTGCGTGCCGCAGGCTTTGGAGCCACTGCCCATCGTCTACTACGTGGGT CGCAAGCCCAAGGTGGAGCAGTTGTCCAACATGATTGTGCGCTCCTGCAAG TGCAGCTGA |
| Human GM-CSF amino acid sequence | 24 | MWLQSLLLLGTVACSISAPARSPSPSTQPWEHVNAIQEARRLLNLSRDTAAEM NETVEVISEMFDLQEPTCLQTRLELYKQGLRGSLTKLKGPLTMMASHYKQHCP PTPETSCATQIITFESFKENLKDFLLVIPFDCWEPVQE |
| Human GM-CSF nucleic acid sequence | 25 | AGTACACAGAGAGAAAGGCTAAAGTTCTCTGGAGGATGTGGCTGCAGAGCC TGCTGCTCTTGGGCACTGTGGCCTGCAGCATCTCTGCACCCGCCCGCTCG CCCAGCCCCAGCACGCAGCCCTGGGAGCATGTGAATGCCATCCAGGAGGC CCGGCGTCTCCTGAACCTGAGTAGAGACACTGCTGCTGAGATGAATGAAAC AGTAGAAGTCATCTCAGAAATGTTTGACCTCCAGGAGCCGACCTGCCTACA GACCCGCCTGGAGCTGTACAAGCAGGGCCTGCGGGGCAGCCTCACCAAGC TCAAGGGCCCCTTGACCATGATGGCCAGCCACTACAAGCAGCACTGCCCTC CAACCCCGGGAAACTTCCTGTGCAACCCAGATTATCACCTTTGAAAGTTTCAA AGAGAACCTGAAGGACTTTCTGCTTGTCATCCCCTTTGACTGCTGGGAGCC AGTCCAGGAGTGAGACCGGCCAGATGAGGCTGGCCAAGCCGGGGAGCTG CTCTCTCATGAAACAAGAGCTAGAAACTCAGGATGGTCATCTTGGAGGGAC CAAGGGGTGGGCCACAGCCATGGTGGGAGTGGCCTGGACCTGCCCTGGG CCACACTGACCCTGATACAGGCATGGCAGAAGAATGGGAATATTTTATACTG ACAGAAATCAGTAATATTTATATATTTATATTTTTAAAATATTTATTTATTTATT TATTTAAGTTCATATTCCATATTTATTCAAGATGTTTTACCGTAATAATTATTAT TAAAAATATGCTTCTACTTG |
| Mouse GM-CSF amino acid sequence | 26 | MWLQNLLFLGIVVYSLSAPTRSPITVTRPWKHVEAIKEALNLLDDMPVTLNEEVE VVSNEFSFKKLTCVQTRLKIFEQGLRGNFTKLKGALNMTASYYQTYCPPTPETD CETQVTTYADFIDSLKTFLTDIPFECKKPGQK |
| Mouse GM-CSF nucleic acid sequence | 27 | ATGTGGCTGCAGAATTTACTTTTCCTGGGCATTGTGGTCTACAGCCTCTCAG CACCCACCCGCTCACCCATCACTGTCACCCGGCCTTGGAAGCATGTAGAGG CCATCAAAGAAGCCCTGAACCTCCTGGATGACATGCCTGTCACGTTGAATG AAGAGGTAGAAGTCGTCTCTAACGAGTTCTCCTTCAAGAAGCTAACATGTGT GCAGACCCGCCTGAAGATATTCGAGCAGGGTCTACGGGGCAATTTCACCAA ACTCAAGGGCGCCTTGAACATGACAGCCAGCTACTACCAGACATACTGCCC CCCAACTCCGGGAAACGGACTGTGAAACACAAGTTACCACCTATGCGGATTT CATAGACAGCCTTAAAACCTTTCTGACTGATATCCCCTTTGAATGCAAAAAA CCAGGCCAAAAATGA |
| Human M-CSF amino acid sequence | 28 | MTAPGAAGRCPPTTWLGSLLLLVCLLASRSITEEVSEYCSHMIGSGHLQSLQRL IDSQMETSCQITFEFVDQEQLKDPVCYLKKAFLLVQDIMEDTMRFRDNTPNAIAI VQLQELSLRLKSCFTKDYEEHDKACVRTFYETPLQLLEKVKNVFNETKNLLDKD WNIFSKNCNNSFAECSSQDVVTKPDCNCLYPKAIPSSDPASVSPHQPLAPSMA PVAGLTWEDSEGTEGSSLLPGEQPLHTVDPGSAKQRPPRSTCQSFEPPETPV VKDSTIGGSPQPRPSVGAFNPGMEDILDSAMGTNWVPEEASGEASEIPVPQGT ELSPSRPGGGSMQTEPARPSNFLSASSPLPASAKGQQPADVTGTALPRVGPV RPTGQDWNHTPQKTDHPSALLRDPPEPGSPRISSLRPQGLSNPSTLSAQPQLS RSHSSGSVLPLGELEGRRSTRDRRSPAEPEGGPASEGAARPLPRFNSVPLTDT GHERQSEGSFSPQLQESVFHLLVPSVILVLLAVGGLLFYRWRRRSHQEPQRAD SPLEQPEGSPLTQDDRQVELPV |
| Human M-CSF nucleic acid sequence | 29 | ATGACCGCGCCGGGCGCCGCCGGGCGCTGCCCTCCCACGACATGGCTGG GCTCCCTGCTGTTGTTGGTCTGTCTCCTGGCGAGCAGGAGTATCACCGAGG AGGTGTCGGAGTACTGTAGCCACATGATTGGGAGTGGACACCTGCAGTCTC TGCAGCGGCTGATTGACAGTCAGATGGAGACCTCGTGCCAAATTACATTTG AGTTTGTAGACCAGGAACAGTTGAAAGATCCAGTGTGCTACCTTAAGAAGG CATTTCTTCCTGGTACAAGACATAATGGAGGACACCATGCGCTTCAGAGATAA CACCCCCAATGCCATCGCCATTGTGCAGCTGCAGGAACTCTCTTTGAGGCT GAAGAGCTGCTTCACCAAGGATTATGAAGAGCATGACAAGGCCTGCGTCCG AACTTTCTATGAGACACCTCTCCAGTTGCTGGAGAAGGTCAAGAATGTCTTT AATGAAACAAAGAATCTCCTTGACAAGGACTGGAATATTTTCAGCAAGAACT GCAACAACAGCTTTGCTGAATGCTCCAGCCAAGATGTGGTGACCAAGCCTG ATTGCAACTGCCTGTACCCCAAAGCCATCCCTAGCAGTGACCCGGCCTCTG TCTCCCCTCATCAGCCCCTCGCCCCCTCCATGGCCCCTGTGGCTGGCTTGA CCTGGGAGGACTCTGAGGGAACTGAGGGCAGCTCCCTCTTGCCTGGTGAG CAGCCCCTGCACACAGTGGATCCAGGCAGTGCCAAGCAGCGGCCACCCAG GAGCACCTGCCAGAGCTTTGAGCCGCCAGAGACCCCAGTTGTCAAGGACA GCACCATCGGTGGCTCACCACAGCCTCGCCCCTCTGTCGGGGCCTTCAAC CCCGGGATGGAGGATATTCTTGACTCTGCAATGGGCACTAATTGGGTCCCA GAAGAAGCCTCTGGAGAGGCCAGTGAGATTCCCGTACCCCAAGGGACAGA GCTTTCCCCCTCCAGGCCAGGAGGGGGCAGCATGCAGACAGAGCCCGCCA GACCCAGCAACTTCCTCTCAGCATCTTCTCCACTCCCTGCATCAGCAAAGG GCCAACAGCCGGCAGATGTAACTGGTACCGCCTTGCCCAGGGTGGGCCCC |

TABLE 6-continued

| Type | SEQ ID NO | Sequence |
|------|-----------|----------|
| | | GTGAGGCCCACTGGCCAGGACTGGAATCACACCCCCCAGAAGACAGACCA TCCATCTGCCCTGCTCAGAGACCCCCCGGAGCCAGGCTCTCCCAGGATCT CATCACTGCGCCCCCAGGGCCTCAGCAACCCCTCCACCCTCTCTGCTCAGC CACAGCTTTCCAGAAGCCACTCCTCGGGCAGCGTGCTGCCCCTTGGGGAG CTGGAGGGCAGGAGGAGCACCAGGGATCGGAGGAGCCCCGCAGAGCCAG AAGGAGGACCAGCAAGTGAAGGGGCAGCCAGGCCCCTGCCCCGTTTTAAC TCCGTTCCTTTGACTGACACAGGCCATGAGAGGCAGTCCGAGGGATCCTTC AGCCCGCAGCTCCAGGAGTCTGTCTTCCACCTGCTGGTGCCCAGTGTCATC CTGGTCTTGCTGGCCGTCGGGAGGCCTCTTGTTCTACAGGTGGAGGCGGCG GAGCCATCAAGAGCCTCAGAGACGGATTCTCCCTTGGAGCAACCAGAGG GCAGCCCCTGACTCAGGATGACAGACAGGTGGAACTGCCAGTGTAG |
| Mouse M-CSF amino acid sequence | 30 | MTARGAAGRCPSSTWLGSRLLLVCLLMSRSIAKEVSEHCSHMIGNGHLKVLQQ LIDSQMETSCQIAFEFVDQEQLDDPVCYLKKAFFLVQDIIDETMRFKDNTPNANA TERLQELSNNLNSCFTKDYEEQNKACVRTFHETPLQLLEKIKNFFNETKNLLEK DWNIFTKNCNNSFAKCSSRDVVTKPDCNCLYPKATPSSDPASASPHQPPAPSM APLAGLAWDDSQRTEGSSLLPSELPLRIEDPGSAKQRPPRSTCQTLESTEQPN HGDRLTEDSQPHPSAGGPVPGVEDILESSLGTNWVLEEASGEASEGFLTQEAK FSPSTPVGGSIQAETDRPRALSASPFPKSTEDQKPVDITDRPLTEVNPMRPIGQ TQNNTPEKTDGTSTLREDHQEPGSPHIATPNPQRVSNSATPVAQLLLPKSHSW GIVLPLGELEGKRSTRDRRSPAELEGGSASEGAARPVARFNSIPLTDTGHVEQH EGSSDPQIPESVFHLLVPGIILVLLTVGGLLFYKWKWRSHRDPQTLDSSVGRPE DSSLTQDEDRQVELPV |
| Mouse M-CSF nucleic acid sequence | 31 | ATGACCGCGCGGGGCGCCGCGGGGCGCTGCCCTTCTTCGACATGGCTGG GCTCCCGGCTGCTGCTGGTCTGTCTCCTCATGAGCAGGAGTATTGCCAAGG AGGTGTCAGAACACTGTAGCCACATGATTGGGAATGGACACCTGAAGGTCC TGCAGCAGTTGATCGACAGTCAAATGGAGACTTCATGCCAGATTGCCTTTGA ATTTGTAGACCAGGAACAGCTGGATGATCCTGTTTGCTACCTAAAGAAGGC CTTTTTTCTGGTACAAGACATAATAGATGAGACCATGCGCTTTAAAGACAAC ACCCCCAATGCTAACGCCACCGAGAGGCTCCAGGAACTCTCCAATAACCTG AACAGCTGCTTCACCAAGGACTATGAGGAGCAGAACAAGGCCTGTGTCCGA ACTTTCCATGAGACTCCTCTCCAGCTGCTGGAGAAGATCAAGAACTTCTTTA ATGAAACAAAGAATCTCCTTGAAAAGGACTGGAACATTTTTACCAAGAACTG CAACAACAGCTTTGCTAAGTGCTCTAGCCGAGATGTGGTGACCAAGCCTGA TTGCAACTGCCTGTACCCTAAAGCCACCCCTAGCAGTGACCCGGCCTCTGC CTCCCCTCACCAGCCCCCGCCCCCTCCATGGCCCCTCTGGCTGGCTTGG CTTGGGATGATTCTCAGAGGACAGAGGGCAGCTCCCTCTTGCCCAGTGAGC TTCCCCTTCGCATAGAGGACCCAGGCAGTGCCAAGCAGCGACCACCCAGG AGTACCTGCCAGACCCTCGAGTCAACAGAGCAACCAAACCATGGGGACAGA CTCACTGAGGACTCACAACCTCATCCTTCTGCGGGGGGGGCCCGTCCCTGG GGTGGAAGACATTCTTGAATCTTCACTGGGCACTAACTGGGTCCTAGAAGA AGCTTCTGGAGAGGCTAGTGAGGGATTTTTGACCCAGGAAGCAAAGTTTTC CCCCTCCACGCCTGTAGGGGGCAGCATCCAGGCAGAGACTGACAGACCCA GGGCCCTCTCAGCATCTCCATTCCCTAAATCAACAGAGGACCAAAAGCCAG TGGATATAACAGACAGGCCGTTGACAGAGGTGAACCCTATGAGACCCATTG GCCAGACACAGAATAATACTCCTGAGAAGACTGATGGTACATCCACGCTGC GTGAAGACCACCAGGAGCCAGGCTCTCCCCATATTGCGACACCGAATCCCC AACGAGTCAGCAACTCAGCCACCCCCGTTGCTCAGTTACTGCTTCCCAAAA GCCACTCTTGGGGCATTGTGCTGCCCCTTGGGGAGCTTGAGGGCAAGAGA AGTACCAGGGATCGAAGGAGCCCCGCAGAGCTGGAAGGAGGATCAGCAAG TGAGGGGGCAGCCAGGCCTGTGGCCCGTTTTAATTCCATTCCTTTGACTGA CACAGGCCATGTGGAGCAGCATGAGGGATCCTCTGACCCCCAGATCCCTG AGTCTGTCTTCCACCTGCTGGTGCCGGGCATCATCCTAGTCTTGCTGACTG TTGGGGGGCCTCCTGTTCTACAAGTGGAAGTGGAGGAGCCATCGAGACCCT CAGACATTGGATTCTTCTGTGGGGCGACCAGAGGACAGCTCCCTGACCCAG GATGAGGACAGACAGGTGGAACTGCCAGTATAG |
| Human IFN-α amino acid sequence | 32 | MALTFALLVALLVLSCKSSCSVGCDLPQTHSLGSRRTLMLLAQMRRISLFSCLK DRHDFGFPQEEFGNQFQKAETIPVLHEMIQQIFNLFSTKDSSAAWDETLLDKFY TELYQQLNDLEACVIQGVGVTETPLMKEDSILAVRKYFQRITLYLKEKKYSPCAW EVVRAEIMRSFSLSTNLQESLRSKE |
| Human IFN-α nucleic acid sequence | 33 | ATGGCCTTGACCTTTGCTTTACTGGTGGCCCTCCTGGTGCTCAGCTGCAAG TCAAGCTGCTCTGTGGGCTGTGATCTGCCTCAAACCCACAGCCTGGGTAGC AGGAGGACCTTGATGCTCCTGGCACAGATGAGGAGAATCTCTCTTTTCTCC TGCTTGAAGGACAGACATGACTTTGGATTTCCCCAGGAGGAGTTTGGCAAC CAGTTCCAAAAGGCTGAAACCATCCCTGTCCTCCATGAGATGATCCAGCAG ATCTTCAATCTCTTCAGCACAAAGGACTCATCTGCTGCTTGGGATGAGACCC TCCTAGACAAATTCTACACTGAACTCTACCAGCAGCTGAATGACCTGGAAGC CTGTGTGATACAGGGGGTGGGGGTGACAGAGACTCCCCTGATGAAGGAGG ACTCCATTCTGGCTGTGAGGAAATACTTCCAAAGAATCACTCTCTATCTGAA AGAGAAGAAATACAGCCCTTGTGCCTGGGAGGTTGTCAGAGCAGAAATCAT GAGATCTTTTTCTTTGTCAACAAACTTGCAAGAAAGTTTAAGAAGTAAGGAAT GA |

TABLE 6-continued

| Type | SEQ ID NO | Sequence |
|---|---|---|
| Mouse IFN-α amino acid sequence | 34 | MARLCAFLMTLLVMSYWSTCSLGCDLPQTHNLRNKRALTLLVQMRRLSPLSCL KDRKDFRFPQEKVDAQQIQNAQAIPVLQELTQQVLNIFTSKDSSAAWDASLLDS FCNDLHQQLNDLKACVMQEVGVQEPPLTQEDYLLAVRTYFHRITVYLREKKHS PCAWEWRAEVWRAMSSSAKLLARLSEEKE |
| Mouse IFN-α nucleic acid sequence | 35 | ATGGCTAGGCTCTGTGCTTTCCTGATGACCCTGCTAGTGATGAGCTACTGG TCAACCTGCTCTCTAGGATGTGACCTGCCTCAGACTCATAACCTCAGGAACA AGAGAGCCTTGACCCTCCTGGTACAAATGAGGAGACTCTCCCCTCTCTCCT GCCTGAAGGACAGAAAGGACTTTAGATTCCCCCAGGAGAAGGTGGATGCC CAGCAGATCCAGAATGCTCAAGCCATCCCTGTCCTACAAGAGCTGACCCAG CAGGTCCTGAACATCTTCACATCAAAGGACTCATCTGCTGCTTGGGATGCAT CCCTCCTAGACTCATTCTGCAATGACCTCCATCAGCAGCTCAATGACCTCAA AGCCTGTGTGATGCAGGAGGTGGGGGTGCAGGAACCTCCCCTGACCCAGG AAGACTACCTGCTGGCTGTGAGGACATACTTCCACAGGATCACTGTGTACC TGAGAGAGAAGAAACACAGCCCCTGTGCCTGGGAGGTGGTCAGAGCAGAA GTCTGGAGAGCCATGTCTTCCTCAGCCAAGTTGCTGGCAAGACTGAGTGAG GAGAAGGAGTGA |
| Human IL-1β amino acid sequence | 36 | MAEVPELASEMMAYYSGNEDDLFFEADGPKQMKCSFQDLDLCPLDGGIQLRIS DHHYSKGFRQAASVVVAMDKLRKMLVPCPQTFQENDLSTFFPFIFEEEPIFFDT WDNEAYVHDAPVRSLNCTLRDSQQKSLVMSGPYELKALHLQGQDMEQQVVF SMSFVQGEESNDKIPVALGLKEKNLYLSCVLKDDKPTLQLESVDPKNYPKKKME KRFVFNKIEINNKLEFESAQFPNWYISTSQAENMPVFLGGTKGGQDITDFTMQF VSS |
| Human IL-1β nucleic acid sequence | 37 | ATGGCAGAAGTACCTGAGCTCGCCAGTGAAATGATGGCTTATTACAGTGGC AATGAGGATGACTTGTTCTTTGAAGCTGATGGCCCTAAACAGATGAAGTGCT CCTTCCAGGACCTGGACCTCTGCCCTCTGGATGGCGGCATCCAGCTACGAA TCTCCGACCACCACTACAGCAAGGGCTTCAGGCAGGCCGCGTCAGTTGTTG TGGCCATGGACAAGCTGAGGAAGATGCTGGTTCCCTGCCCACAGACCTTCC AGGAGAATGACCTGAGCACCTTCTTTCCCTTCATCTTTGAAGAAGAACCTAT CTTCTTCGACACATGGGATAACGAGGCTTATGTGCACGATGCACCTGTACG ATCACTGAACTGCACGCTCCGGGACTCACAGCAAAAAAGCTTGGTGATGTC TGGTCCATATGAACTGAAAGCTCTCCACCTCCAGGGACAGGATATGGAGCA ACAAGTGGTGTTCTCCATGTCCTTTGTACAAGGAGAAGAAAGTAATGACAAA ATACCTGTGGCCTTGGGCCTCAAGGAAAAGAATCTGTACCTGTCCTGCGTG TTGAAAGATGATAAGCCCACTCTACAGCTGGAGAGTGTAGATCCCAAAAATT ACCCAAAGAAGAAGATGGAAAAGCGATTTGTCTTCAACAAGATAGAAATCAA TAACAAGCTGGAATTTGAGTCTGCCCAGTTCCCCAACTGGTACATCAGCAC CTCTCAAGCAGAAAACATGCCCGTCTTCCTGGGAGGGACCAAAGGCGGCC AGGATATAACTGACTTCACCATGCAATTTGTGTCTTCCTAA |
| Mouse IL-1β amino acid sequence | 38 | MATVPELNCEMPPFDSDENDLFFEVDGPQKMKGCFQTFDLGCPDESIQLQISQ QHINKSFRQAVSLIVAVEKLWQLPVSFPWTFQDEDMSTFFSFIFEEEPILCDSW DDDDNLLVCDVPIRQLHYRLRDEQQKSLVLSDPYELKALHLNGQNINQQVIFSM SFVQGEPSNDKIPVALGLKGKNLYLSCVMKDGTPTLQLESVDPKQYPKKKMEK RFVFNKIEVKSKVEFESAEFPNWYISTSQAEHKPVFLGNNSGQDIIDFTMESVSS |
| Mouse IL-1β nucleic acid sequence | 39 | ATGGCAACTGTTCCTGAACTCAACTGTGAAATGCCACCTTTTGACAGTGATG AGAATGACCTGTTCTTTGAAGTTGACGGACCCCAAAAGATGAAGGGCTGCT TCCAAACCTTTGACCTGGGCTGTCCTGATGAGAGCATCCAGCTTCAAATCTC GCAGCAGCACATCAACAAGAGCTTCAGGCAGGCAGTATCACTCATTGTGGC TGTGGAGAAGCTGTGGCAGCTACCTGTGTCTTTCCCGTGGACCTTCCAGGA TGAGGACATGAGCACCTTCTTTTCCTTCATCTTTGAAGAAGAGCCCATCCTC TGTGACTCATGGGATGATGATGATAACCTGCTGGTGTGTGACGTTCCCATTA GACAACTGCACTACAGGCTCCGAGATGAACAACAAAAAAAGCCTCGTGCTGT CGGACCCATATGAGCTGAAAGCTCTCCACCTCAATGGACAGAATATCAACC AACAAGTGATATTCTCCATGAGCTTTGTACAAGGAGAACCAAGCAACGACAA AATACCTGTGGCCTTGGGCCTCAAAGGAAAGAATCTATACCTGTCCTGTGTA ATGAAAGACGGCACACCCACCCTGCAGCTGGAGAGTGTGGATCCCAAGCA ATACCCAAAGAAGAAGATGGAAAAAACGGTTTGTCTTCAACAAGATAGAAGTC AAGAGCAAAGTGGAGTTTGAGTCTGCAGAGTTCCCCAACTGGTACATCAGC ACCTCACAAGCAGAGCACAAGCCTGTCTTCCTGGGAAACAACAGTGGTCAG GACATAATTGACTTCACCATGGAATCCGTGTCTTCCTAA |
| Human IL-13 amino acid sequence | 40 | MHPLLNPLLLALGLMALLLTTVIALTCLGGFASPGPVPPSTALRELIEELVNITQN QKAPLCNGSMVWSINLTAGMYCAALESLINVSGCSAIEKTQRMLSGFCPHKVS AGQFSSLHVRDTKIEVAQFVKDLLLHLKKLFREGRFN |
| Human IL-13 nucleic acid sequence | 41 | ATGCATCCGCTCCTCAATCCTCTCCTGTTGGCACTGGGCCTCATGGCGCTT TTGTTGACCACGGTCATTGCTCTCACTTGCCTTGGCGGCTTTGCCTCCCCA GGCCCTGTGCCTCCCTCTACAGCCCTCAGGGAGCTCATTGAGGAGCTGGT CAACATCACCCAGAACCAGAAGGCTCCGCTCTGCAATGGCAGCATGGTATG GAGCATCAACCTGACAGCTGGCATGTACTGTGCAGCCCTGGAATCCCTGAT |

TABLE 6-continued amino acid sequences and nucleic acid sequences

| Type | SEQ ID NO | Sequence |
|------|-----------|----------|
| | | CAACGTGTCAGGCTGCAGTGCCATCGAGAAGACCCAGAGGATGCTGAGCG<br>GATTCTGCCCGCACAAGGTCTCAGCTGGGCAGTTTTCCAGCTTGCATGTCC<br>GAGACACCAAAATCGAGGTGGCCCAGTTTGTAAAGGACCTGCTCTTACATTT<br>AAAGAAACTTTTTCGCGAGGGACGGTTCAACTGA |
| Mouse IL-13 amino acid sequence | 42 | MALWVTAVLALACLGGLAAPGPVPRSVSLPLTLKELIEELSNITQDQTPLCNGS<br>MVWSVDLAAGGFCVALDSLTNISNCNAIYRTQRILHGLCNRKAPTTVSSLPDTKI<br>EVAHFITKLLSYTKQLFRHGPF |
| Mouse IL-13 nucleic acid sequence | 43 | ATGGCGCTCTGGGTGACTGCAGTCCTGGCTCTTGCTTGCCTTGGTGGTCTC<br>GCCGCCCCAGGGCCGGTGCCAAGATCTGTGTCTCTCCCTCTGACCCTTAAG<br>GAGCTTATTGAGGAGCTGAGCAACATCACACAAGACCAGACTCCCCTGTGC<br>AACGGCAGCATGGTATGGAGTGTGGACCTGGCCGCTGGCGGGTTCTGTGT<br>AGCCCTGGATTCCCTGACCAACATCTCCAATTGCAATGCCATCTACAGGAC<br>CCAGAGGATATTGCATGGCCTCTGTAACCGCAAGGCCCCCACTACGGTCTC<br>CAGCCTCCCCGATACCAAAATCGAAGTAGCCCACTTTATAACAAAACTGCTC<br>AGCTACACAAAGCAACTGTTTCGCCACGGCCCCTTCTAA |
| Human TNF-α amino acid sequence | 44 | MSTESMIRDVELAEEALPKKTGGPQGSRRCLFLSLFSFLIVAGATTLFCLLHFGV<br>IGPQREEFPRDLSLISPLAQAVRSSSRTPSDKPVAHVVANPQAEGQLQWLNRR<br>ANALLANGVELRDNQLVVPSEGLYLIYSQVLFKGQGCPSTHVLLTHTISRIAVSY<br>QTKVNLLSAIKSPCQRETPEGAEAKPWYEPIYLGGVFQLEKGDRLSAEINRPDY<br>LDFAESGQVYFGIIAL |
| Human TNF-α nucleic acid sequence | 45 | ATGAGCACTGAAAGCATGATCCGGGACGTGGAGCTGGCCGAGGAGGCGCT<br>CCCCAAGAAGACAGGGGGGCCCCAGGGCTCCAGGCGGTGCTTGTTCCTCA<br>GCCTCTTCTCCTTCCTGATCGTGGCAGGCGCCACCACGCTCTTCTGCCTGC<br>TGCACTTTGGAGTGATCGGCCCCCAGAGGGAAGAGTTCCCCAGGGACCTC<br>TCTCTAATCAGCCCTCTGGCCCAGGCAGTCAGATCATCTTCTCGAACCCCG<br>AGTGACAAGCCTGTAGCCCATGTTGTAGCAAACCCTCAAGCTGAGGGGCAG<br>CTCCAGTGGCTGAACCGCCGGGCCAATGCCCTCCTGGCCAATGGCGTGGA<br>GCTGAGAGATAACCAGCTGGTGGTGCCATCAGAGGGCCTGTACCTCATCTA<br>CTCCCAGGTCCTCTTCAAGGGCCAAGGCTGCCCCTCCACCCATGTGCTCCT<br>CACCCACACCATCAGCCGCATCGCCGTCTCCTACCAGACCAAGGTCAACCT<br>CCTCTCTGCCATCAAGAGCCCCTGCCAGAGGGGAGACCCCAGAGGGGGCTG<br>AGGCCAAGCCCTGGTATGAGCCCATCTATCTGGGAGGGGTCTTCCAGCTG<br>GAGAAGGGTGACCGACTCAGCGCTGAGATCAATCGGCCCGACTATCTCGA<br>CTTTGCCGAGTCTGGGCAGGTCTACTTTGGGATCATTGCCCTGTGA |
| Mouse TNF-α amino acid sequence | 46 | MSTESMIRDVELAEEALPQKMGGFQNSRRCLCLSLFSFLLVAGATTLFCLLNFG<br>VIGPQRDEKFPNGLPLISSMAQTLTLRSSSQNSSDKPVAHVVANHQVEEQLEW<br>LSQRANALLANGMDLKDNQLVVPADGLYLVYSQVLFKGQGCPDYVLLTHTVSR<br>FAISYQEKVNLLSAVKSPCPKDTPEGAELKPWYEPIYLGGVFQLEKGDQLSAEV<br>NLPKYLDFAESGQVYFGVIAL |
| Mouse TNF-α nucleic acid sequence | 47 | ATGAGCACAGAAAGCATGATCCGCGACGTGGAACTGGCAGAAGAGGCACT<br>CCCCCAAAAGATGGGGGGCTTCCAGAACTCCAGGCGGTGCCTATGTCTCA<br>GCCTCTTCTCATTCCTGCTTGTGGCAGGGGCCACCACGCTCTTCTGTCTAC<br>TGAACTTCGGGGTGATCGGTCCCCAAAGGGATGAGAAGTTCCCAAATGGCC<br>TCCCTCTCATCAGTTCTATGGCCCAGACCCTCACACTCAGATCATCTTCTCA<br>AAATTCGAGTGACAAGCCTGTAGCCCACGTCGTAGCAAACCACCAAGTGGA<br>GGAGCAGCTGGAGTGGCTGAGCCAGCGCGCCAACGCCCTCCTGGCCAAC<br>GGCATGGATCTCAAAGACAACCAACTAGTGGTGCCAGCCGATGGGTTGTAC<br>CTTGTCTACTCCCAGGTTCTCTTCAAGGGACAAGGCTGCCCCGACTACGTG<br>CTCCTCACCCACACCGTCAGCCGATTTGCTATCTCATACCAGGAGAAAGTC<br>AACCTCCTCTCTGCCGTCAAGAGCCCCTGCCCCAAGGACACCCCTGAGGG<br>GGCTGAGCTCAAACCCTGGTATGAGCCCATATACCTGGGAGGAGTCTTCCA<br>GCTGGAGAAGGGGGACCAACTCAGCGCTGAGGTCAATCTGCCCAAGTACT<br>TAGACTTTGCGGAGTCCGGGCAGGTCTACTTTGGAGTCATTGCTCTGTGA |

Example 3: Examples of Embodiments

The examples set forth below illustrate certain embodiments and do not limit the technology.

A1. A method for assessing activity of an IL-40 polypeptide comprising:

a) contacting a cell with a first composition comprising an IL-40 polypeptide;

b) measuring production by the cell of one or more cytokines and/or chemokines chosen from CCL2, CCL3, CCL4, CCL5, CCL11, CXCL8, CXCL10, and IL-1RA, thereby measuring cytokine production; and c) detecting the activity of the IL-40 polypeptide in the first composition according to the cytokine production measured in (b).

A2. The method of embodiment A1, wherein the production of the one or more cytokines and/or chemokines is increased compared to the production by a cell not contacted with the first composition.

A3. The method of embodiment A1 or A2, wherein (a) comprises contacting the cell with a second composition comprising a co-stimulant.

A4. The method of embodiment A3, wherein the co-stimulant comprises IFN-γ.

A5. The method of embodiment A3 or A4, wherein (a) comprises simultaneously contacting the cell with the first composition and the second composition.

A6. The method of embodiment A3 or A4, wherein (a) comprises contacting the cell with the second composition prior to contacting the cell with the first composition.

A7. The method of any one of embodiment A3 to A6, wherein the production of the one or more cytokines and/or chemokines is increased compared to the production by a cell not contacted with the first composition and the second composition.

A8. A method for assessing activity of an IL-40 polypeptide comprising:
  a) contacting a cell with a first composition comprising an IL-40 polypeptide and a second composition comprising a co-stimulant;
  b) measuring production by the cell of one or more cytokines and/or chemokines chosen from CCL2, CCL3, CCL4, CCL5, CCL11, CCL17, CCL20, CXCL1, CXCL5, CXCL8, CXCL9, CXCL10, CXCL11, IL-1RA, and IL-6, thereby measuring cytokine production; and
  c) detecting the activity of the IL-40 polypeptide in the first composition according to the cytokine production measured in (b).

A9. The method of embodiment A8, wherein the production of the one or more cytokines and/or chemokines is increased compared to the production by a cell not contacted with the first composition and the second composition.

A10. The method of embodiment A8 or A9, wherein the co-stimulant comprises IFN-γ.

A11. The method of any one of embodiments A8 to A10, wherein (a) comprises simultaneously contacting the cell with the first composition and the second composition.

A12. The method of any one of embodiments A8 to A10, wherein (a) comprises contacting the cell with the second composition prior to contacting the cell with the first composition.

A13. The method of any one of embodiments A1 to A12, wherein the cell is from a subject.

A14. The method of any one of embodiments A1 to A12, wherein the cell is from a cell line.

A15. The method of any one of embodiments A1 to A14, wherein the cell is an isolated cell.

A16. The method of any one of embodiments A1 to A15, wherein the cell is an immune cell.

A17. The method of embodiment A16, wherein the cell is a monocyte.

A18. The method of embodiment A16, wherein the cell is a macrophage.

A19. The method of any one of embodiments A1 to A15, wherein the cell is a non-immune cell.

A20. The method of embodiment A19, wherein the cell is a stromal cell or a cell derived from the central nervous system.

A21. The method of any one of embodiments A1 to A20, wherein the method is performed ex vivo or in vitro.

A22. The method of any one of embodiments A1 to A21, wherein the IL-40 polypeptide is a recombinant IL-40 polypeptide.

A23. The method of any one of embodiments A1 to A21, wherein the IL-40 polypeptide is a human IL-40 polypeptide.

A24. The method of embodiment A23, wherein the IL-40 polypeptide is a recombinant human IL-40 polypeptide.

A25. The method of embodiment A23 or A24, wherein the IL-40 polypeptide comprises the amino acid sequence of SEQ ID NO: 1.

A26. The method of embodiment A23 or A24, wherein the IL-40 polypeptide comprises amino acids 21-265 of SEQ ID NO: 1.

A27. The method of embodiment A23 or A24, wherein the IL-40 polypeptide comprises a fragment of the amino acid sequence of SEQ ID NO: 1.

A28. The method of embodiment A23 or A24, wherein the IL-40 polypeptide comprises one or more amino acid substitutions in the amino acid sequence of SEQ ID NO: 1.

A29. The method of embodiment A23 or A24, wherein the IL-40 polypeptide comprises a fragment comprising one or more amino acid substitutions in the amino acid sequence of SEQ ID NO: 1.

A30. The method of any one of embodiments A1 to A21, wherein the IL-40 polypeptide is a mouse IL-40 polypeptide.

A31. The method of embodiment A30, wherein the IL-40 polypeptide is a recombinant mouse IL-40 polypeptide.

A32. The method of embodiment A30 or A31, wherein the IL-40 polypeptide comprises the amino acid sequence of SEQ ID NO: 3.

A33. The method of embodiment A30 or A31, wherein the IL-40 polypeptide comprises amino acids 19-252 of SEQ ID NO: 3.

A34. The method of embodiment A30 or A31, wherein the IL-40 polypeptide comprises a fragment of the amino acid sequence of SEQ ID NO: 3.

A35. The method of embodiment A30 or A31, wherein the IL-40 polypeptide comprises one or more amino acid substitutions in the amino acid sequence of SEQ ID NO: 3.

A36. The method of embodiment A30 or A31, wherein the IL-40 polypeptide comprises a fragment comprising one or more amino acid substitutions in the amino acid sequence of SEQ ID NO: 3.

A37. The method of any one of embodiments A1 to A36, wherein the IL-40 polypeptide comprises one or more chemical modifications.

A38. The method of any one of embodiments A1 to A37, wherein the IL-40 polypeptide comprises a tag.

A39. The method of any one of embodiments A1 to A38, wherein the IL-40 polypeptide comprises a detectable label.

A40. The method of any one of embodiments A1 to A39, wherein the IL-40 polypeptide comprises a fused polypeptide.

B1. A method for assessing activity of an IL-40 polypeptide comprising:
  a) contacting a population of monocytes with a first composition comprising an IL-40 polypeptide;
  b) detecting monocyte to macrophage differentiation in the population; and
  c) assessing the activity of the IL-40 polypeptide in the first composition according to the monocyte to macrophage differentiation detected in (b).

B2. The method of embodiment B1, wherein the monocyte to macrophage differentiation is detected according to changes in cell morphology.

B3. The method of embodiment B2, wherein at least about 10% of the cells in the population show changes in cell morphology.

B4. The method of embodiment B1, wherein the monocyte to macrophage differentiation is detected according to expression of one or more markers chosen from CD14, Ly6C, CD115, CD15s, CD33, CD44, CD81, CD49e, CD18, CD11b, CD54 (ICAM-1), CD11c, CD68, CD80, CD86, CD163, IL-1R, and CD200R.

B4.1 The method of embodiment B1, wherein the monocyte to macrophage differentiation is detected according to increased expression of one or more markers chosen from CD44, CD81, CD49e, CD18, CD11b, CD54 (ICAM-1), CD11c, CD68, CD80, CD86, CD163, IL-1R, and CD200R.

B4.2 The method of embodiment B1, wherein the monocyte to macrophage differentiation is detected according to decreased expression of one or more markers chosen from CD14, Ly6C, CD115, CD15s, and CD33.

B5. The method of embodiment B1, wherein the monocyte to macrophage differentiation is detected according to increased production of one or more chemokines chosen from CCL10, CCL11, CCL5, CCL8, CCL9, CCL2, CCL3, CCL4, CCL17, CCL22, CCL24, CCL1, CCR2, CCL5, CXCL10, CXCL8, CXCL9, and CXCL16.

B5.1 The method of embodiment B1, wherein the monocyte to macrophage differentiation is detected according to increased production of one or more cytokines chosen from TNF, IL-1 beta, IL-6, IL-12, IL-23, IL-10, TGF-beta, IL-1RA, IL-1, TNF-alpha, and IL-10.

B6. The method of embodiment B1, wherein (a) comprises contacting the population of monocytes with a second composition comprising a co-stimulant.

B7. The method of embodiment B6, wherein the co-stimulant comprises IFN-γ.

B8. The method of embodiment B6 or B7, wherein (a) comprises simultaneously contacting the population of monocytes with the first composition and the second composition.

B9. The method of embodiment B6 or B7, wherein (a) comprises contacting the population of monocytes with the second composition prior to contacting the cell with the first composition.

B10. The method of any one of embodiments B6 to B9, wherein the monocyte to macrophage differentiation is detected according to changes in cell morphology.

B11. The method of embodiment B10, wherein at least about 30% of the cells in the population show changes in cell morphology.

B12. The method of any one of embodiments B6 to B9, wherein the monocyte to macrophage differentiation is detected according to expression of one or more markers chosen from CD14, Ly6C, CD115, CD15s, CD33, CD44, CD81, CD49e, CD18, CD11b, CD54 (ICAM-1), CD11c, CD68, CD80, CD86, CD163, IL-1R, and CD200R.

B12.1 The method of any one of embodiments B6 to B9, wherein the monocyte to macrophage differentiation is detected according to increased expression of one or more markers chosen from CD44, CD81, CD49e, CD18, CD11b, CD54 (ICAM-1), CD11c, CD68, CD80, CD86, CD163, IL-1R, and CD200R.

B12.2 The method of any one of embodiments B6 to B9, wherein the monocyte to macrophage differentiation is detected according to decreased expression of one or more markers chosen from CD14, Ly6C, CD115, CD15s, and CD33.

B13. The method of any one of embodiments B6 to B9, wherein the monocyte to macrophage differentiation is detected according to increased production of one or more chemokines chosen from CCL10, CCL11, CCL5, CCL8, CCL9, CCL2, CCL3, CCL4, CCL17, CCL22, CCL24, CCL1, CCR2, CCL5, CXCL10, CXCL8, CXCL9, and CXCL16.

B13.1 The method of any one of embodiments B6 to B9, wherein the monocyte to macrophage differentiation is detected according to increased production of one or more cytokines chosen from TNF, IL-1 beta, IL-6, IL-12, IL-23, IL-10, TGF-beta, IL-1RA, IL-1, TNF-alpha, and IL-10.

B14. The method of any one of embodiments B1 to B13.1, wherein the population of monocytes is from a subject.

B15. The method of any one of embodiments B1 to B13.1, wherein the population of monocytes is from a cell line.

B16. The method of any one of embodiments B1 to B15, wherein the population of monocytes comprises isolated monocytes.

B17. The method of any one of embodiments B1 to B16, wherein the method is performed ex vivo or in vitro.

B18. The method of any one of embodiments B1 to B17, wherein the IL-40 polypeptide is a recombinant IL-40 polypeptide.

B19. The method of any one of embodiments B1 to B17, wherein the IL-40 polypeptide is a human IL-40 polypeptide.

B20. The method of embodiment B19, wherein the IL-40 polypeptide is a recombinant human IL-40 polypeptide.

B21. The method of embodiment B19 or B20, wherein the IL-40 polypeptide comprises the amino acid sequence of SEQ ID NO: 1.

B22. The method of embodiment B19 or B20, wherein the IL-40 polypeptide comprises amino acids 21-265 of SEQ ID NO: 1.

B23. The method of embodiment B19 or B20, wherein the IL-40 polypeptide comprises a fragment of the amino acid sequence of SEQ ID NO: 1.

B24. The method of embodiment B19 or B20, wherein the IL-40 polypeptide comprises one or more amino acid substitutions in the amino acid sequence of SEQ ID NO: 1.

B25. The method of embodiment B19 or B20, wherein the IL-40 polypeptide comprises a fragment comprising one or more amino acid substitutions in the amino acid sequence of SEQ ID NO: 1.

B26. The method of any one of embodiments B1 to B17, wherein the IL-40 polypeptide is a mouse IL-40 polypeptide.

B27. The method of embodiment B26, wherein the IL-40 polypeptide is a recombinant mouse IL-40 polypeptide.

B28. The method of embodiment B26 or B27, wherein the IL-40 polypeptide comprises the amino acid sequence of SEQ ID NO: 3.

B29. The method of embodiment B26 or B27, wherein the IL-40 polypeptide comprises amino acids 19-252 of SEQ ID NO: 3.

B30. The method of embodiment B26 or B27, wherein the IL-40 polypeptide comprises a fragment of the amino acid sequence of SEQ ID NO: 3.

B31. The method of embodiment B26 or B27, wherein the IL-40 polypeptide comprises one or more amino acid substitutions in the amino acid sequence of SEQ ID NO: 3.

B32. The method of embodiment B26 or B27, wherein the IL-40 polypeptide comprises a fragment comprising one or more amino acid substitutions in the amino acid sequence of SEQ ID NO: 3.

B33. The method of any one of embodiments B1 to B32, wherein the IL-40 polypeptide comprises one or more chemical modifications.

B34. The method of any one of embodiments B1 to B33, wherein the IL-40 polypeptide comprises a tag.

B35. The method of any one of embodiments B1 to B34, wherein the IL-40 polypeptide comprises a detectable label.

B36. The method of any one of embodiments B1 to B35, wherein the IL-40 polypeptide comprises a fused polypeptide.

C1. A method for inducing differentiation of a monocyte to a macrophage, comprising contacting a monocyte with a first composition comprising an IL-40 polypeptide.

C2. The method of embodiment C1, wherein the differentiation of a monocyte to a macrophage is characterized by changes in cell morphology.

C3. The method of embodiment C2, wherein at least about 10% of cells in a population of monocytes show changes in cell morphology.

C4. The method of embodiment C1, wherein the differentiation of a monocyte to a macrophage is characterized by expression of one or more markers chosen from CD14, Ly6C, CD115, CD15s, CD33, CD44, CD81, CD49e, CD18, CD11b, CD54 (ICAM-1), CD11c, CD68, CD80, CD86, CD163, IL-1R, and CD200R.

C5. The method of embodiment C1, wherein the differentiation of a monocyte to a macrophage is characterized by increased expression of one or more markers chosen from CD44, CD81, CD49e, CD18, CD11b, CD54 (ICAM-1), CD11c, CD68, CD80, CD86, CD163, IL-1R, and CD200R.

C6. The method of embodiment C1, wherein the differentiation of a monocyte to a macrophage is characterized by decreased expression of one or more markers chosen from CD14, Ly6C, CD115, CD15s, and CD33.

C7. The method of embodiment C1, wherein the differentiation of a monocyte to a macrophage is characterized by increased production of one or more chemokines chosen from CCL10, CCL11, CCL5, CCL8, CCL9, CCL2, CCL3, CCL4, CCL17, CCL22, CCL24, CCL1, CCR2, CCL5, CXCL10, CXCL8, CXCL9, and CXCL16.

C8. The method of embodiment C1, wherein the differentiation of a monocyte to a macrophage is characterized by increased production of one or more cytokines chosen from TNF, IL-1 beta, IL-6, IL-12, IL-23, IL-10, TGF-beta, IL-1RA, IL-1, TNF-alpha, and IL-10.

C9. The method of embodiment C1, comprising contacting the monocyte with a second composition comprising a co-stimulant.

C10. The method of embodiment C9, wherein the co-stimulant comprises IFN-γ.

C11. The method of embodiment C9 or C10, comprising simultaneously contacting the monocyte with the first composition and the second composition.

C12. The method of embodiment C9 or C10, comprising contacting the monocyte with the second composition prior to contacting the monocyte with the first composition.

C13. The method of any one of embodiments C9 to C12, wherein the differentiation of a monocyte to a macrophage is characterized by changes in cell morphology.

C14. The method of embodiment C13, wherein at least about 30% of cells in a population of monocytes show changes in cell morphology.

C15. The method of any one of embodiments C9 to C12, wherein the differentiation of a monocyte to a macrophage is characterized by expression of one or more markers chosen from CD14, Ly6C, CD115, CD15s, CD33, CD44, CD81, CD49e, CD18, CD11b, CD54 (ICAM-1), CD11c, CD68, CD80, CD86, CD163, IL-1R, and CD200R.

C16. The method of any one of embodiments C9 to C12, wherein the differentiation of a monocyte to a macrophage is characterized by increased expression of one or more markers chosen from CD44, CD81, CD49e, CD18, CD11b, CD54 (ICAM-1), CD11c, CD68, CD80, CD86, CD163, IL-1R, and CD200R.

C17. The method of any one of embodiments C9 to C12, wherein the differentiation of a monocyte to a macrophage is characterized by decreased expression of one or more markers chosen from CD14, Ly6C, CD115, CD15s, and CD33.

C18. The method of any one of embodiments C9 to C12, wherein the differentiation of a monocyte to a macrophage is characterized by increased production of one or more chemokines chosen from CCL10, CCL11, CCL5, CCL8, CCL9, CCL2, CCL3, CCL4, CCL17, CCL22, CCL24, CCL1, CCR2, CCL5, CXCL10, CXCL8, CXCL9, and CXCL16.

C19. The method of any one of embodiments C9 to C12, wherein the differentiation of a monocyte to a macrophage is characterized by increased production of one or more cytokines chosen from TNF, IL-1 beta, IL-6, IL-12, IL-23, IL-10, TGF-beta, IL-1RA, IL-1, TNF-alpha, and IL-10.

C20. The method of any one of embodiments C1 to C19, wherein the monocyte is from a subject.

C21. The method of any one of embodiments C1 to C19, wherein the monocyte is from a cell line.

C22. The method of any one of embodiments C1 to C21, wherein the monocyte is an isolated monocyte.

C23. The method of any one of embodiments C1 to C22, wherein the method is performed ex vivo or in vitro.

C24. The method of any one of embodiments C1 to C23, wherein the IL-40 polypeptide is a recombinant IL-40 polypeptide.

C25. The method of any one of embodiments C1 to C23, wherein the IL-40 polypeptide is a human IL-40 polypeptide.

C26. The method of embodiment C25, wherein the IL-40 polypeptide is a recombinant human IL-40 polypeptide.

C27. The method of embodiment C25 or C26, wherein the IL-40 polypeptide comprises the amino acid sequence of SEQ ID NO: 1 or amino acids 21-265 of SEQ ID NO: 1; or a functional fragment thereof; or a modified polypeptide thereof; or a modified functional fragment thereof.

C28. The method of any one of embodiments C1 to C23, wherein the IL-40 polypeptide is a mouse IL-40 polypeptide.

C29. The method of embodiment C28, wherein the IL-40 polypeptide is a recombinant mouse IL-40 polypeptide.

C30. The method of embodiment C28 or C29, wherein the IL-40 polypeptide comprises the amino acid sequence of SEQ ID NO: 3 or amino acids 19-252 of SEQ ID NO: 3; or a functional fragment thereof; or a modified polypeptide thereof; or a modified functional fragment thereof.

D1. A kit, comprising:
  a) a first composition comprising an IFN-γ polypeptide;
  b) one or more components for measuring cytokine and/or chemokine production, wherein the cytokines and/or chemokines are chosen from one or more of CCL2, CCL3, CCL4, CCL5, CCL11, CCL17, CCL20, CXCL1, CXCL5, CXCL8, CXCL9, CXCL10, CXCL11, IL-1RA, and IL-6; and
  c) instructions for use.

D2. The kit of embodiment D1, further comprising a second composition comprising an IL-40 polypeptide.

D3. The kit of embodiment D2, wherein the IL-40 polypeptide is a recombinant IL-40 polypeptide.

D4. The kit of embodiment D2, wherein the IL-40 polypeptide is a human IL-40 polypeptide.

D5. The kit of embodiment D4, wherein the IL-40 polypeptide is a recombinant human IL-40 polypeptide.

D6. The kit of embodiment D4 or D5, wherein the IL-40 polypeptide comprises the amino acid sequence of SEQ ID NO: 1.

D7. The kit of embodiment D4 or D5, wherein the IL-40 polypeptide comprises amino acids 21-265 of SEQ ID NO: 1.

D8. The kit of embodiment D4 or D5, wherein the IL-40 polypeptide comprises a fragment of the amino acid sequence of SEQ ID NO: 1.

D9. The kit of embodiment D4 or D5, wherein the IL-40 polypeptide comprises one or more amino acid substitutions in the amino acid sequence of SEQ ID NO: 1.

D10. The kit of embodiment D4 or D5, wherein the IL-40 polypeptide comprises a fragment comprising one or more amino acid substitutions in the amino acid sequence of SEQ ID NO: 1.

D11. The kit of embodiment D2, wherein the IL-40 polypeptide is a mouse IL-40 polypeptide.

D12. The kit of embodiment D10, wherein the IL-40 polypeptide is a recombinant mouse IL-40 polypeptide.

D13. The kit of embodiment D11 or D12, wherein the IL-40 polypeptide comprises the amino acid sequence of SEQ ID NO: 3.

D14. The kit of embodiment D11 or D12, wherein the IL-40 polypeptide comprises amino acids 19-252 of SEQ ID NO: 3.

D15. The kit of embodiment D11 or D12, wherein the IL-40 polypeptide comprises a fragment of the amino acid sequence of SEQ ID NO: 3.

D16. The kit of embodiment D11 or D12, wherein the IL-40 polypeptide comprises one or more amino acid substitutions in the amino acid sequence of SEQ ID NO: 3.

D17. The kit of embodiment D11 or D12, wherein the IL-40 polypeptide comprises a fragment comprising one or more amino acid substitutions in the amino acid sequence of SEQ ID NO: 3.

D18. The kit of any one of embodiments D2 to D17, wherein the IL-40 polypeptide comprises one or more chemical modifications.

D19. The kit of any one of embodiments D2 to D18, wherein the IL-40 polypeptide comprises a tag.

D20. The kit of any one of embodiments D2 to D19, wherein the IL-40 polypeptide comprises a detectable label.

D21. The kit of any one of embodiments D2 to D20, wherein the IL-40 polypeptide comprises a fused polypeptide.

D22. The kit of any one of embodiments D1 to D21, wherein each of the one or more components for measuring cytokine and/or chemokine production comprises a binding molecule that immunospecifically binds to one of the cytokines and/or chemokines under binding conditions.

D23. The kit of any one of embodiments D1 to D22, further comprising a cell or a population of cells.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A method for assessing activity of an Interleukin 40 (IL-40) polypeptide in a sample comprising: a) disposing one or more cells on an immobilized support, wherein said immobilized support comprises analyte specific capture agents; b) incubating the one or more cells with a first composition comprising a recombinant IL-40 polypeptide or fragment thereof, under conditions to bind said first composition to its selective receptor on the cell; wherein the binding generates the production of one or more analytes, c) capturing said one or more analytes onto said capture agents, thereby generating one or more analyte/capture agent complexes; e) detecting the presence or absence of said analyte/ capture agent complexes; and f) measuring the activity of the IL-40 polypeptide according to the presence or absence of said analyte/capture agent complexes, wherein the one or more analytes comprises cytokines, chemokines, and/or growth factors and wherein the one or more cytokines, chemokines, and/or growth factors is selected from the group consisting of chemokine (C—C motif) ligand 2 (CCL2), chemokine (C—C motif) ligand 3 (CCL3), chemokine (C—C motif) ligand 4 (CCL4), chemokine (C—C motif) ligand 5 (CCL5), chemokine (C—C motif) ligand 11 (CCL11), chemokine (C—X—C motif) ligand 8 (CXCL8), chemokine (C—X—C motif) ligand 10 (CXCL10), interleukin-1 receptor antagonist (IL-IRA), erythropoietin, platelet derived growth factor AA (PDGF-AA) and vascular endothelial growth factor (VEGF).

2. The method of claim 1, wherein the incubating comprises contacting the one or more cells with a second composition comprising a co-stimulant.

3. The method of claim 2, wherein the co-stimulant comprises one or more polypeptides is selected from the group consisting of granulocyte-macrophage colony-stimulating factor (GM-CSF), interferon-alpha (IFN-a), interferon-gamma (IFN-y), interleukin 1 beta (IL-13), interleukin 4 (IL-4), interleukin 10 (IL-10), interleukin 13 (IL-13), tumor necrosis factor alpha (TNF-a), transforming growth factor beta (TGF-3), and macrophage colony-stimulating factor (M-CSF).

4. The method of claim 1, wherein the capture agents comprise a fusion tag or detectable label.

5. A method of assessing activity of an IL-40 polypeptide in a sample, comprising:
   a) contacting a population of monocytes with a first composition comprising an IL-40 polypeptide, wherein the contacting is performed in an analysis device comprising a surface;

b) measuring monocyte to macrophage differentiation in the population;
   c) calculating the presence or absence of activity of the IL-40 polypeptide based on the macrophage differentiation.

6. The method of claim 5, wherein the contacting comprises incubating the population of monocytes with a second composition comprising a co-stimulant.

7. The method of claim 6, wherein the co-stimulant comprises one or more polypeptides is selected from the group consisting of GM-CSF, IFN-a, IFN-y, IL-13, IL-4, IL-10, IL-13, TNF-a, TGF-3, and M-CSF.

8. The method of claim 5, wherein the measuring comprises (i) applying a light source to the sample; (ii) identifying the number of cells adhered to the surface of the analysis device; and (iii) calculating a percentage of the number of dividing the cells in (ii) between the total cell number.

9. The method of claim 5, wherein the presence of activity of the IL-40 polypeptide comprises at least at or about 5% of cells adhered to the surface.

10. The method of claim 6, wherein the presence of activity of the IL-40 polypeptide comprises at least at or about 30% of cells adhered to the surface.

11. The method of claim 5, wherein the presence of activity of the IL-40 polypeptide comprises detection of increased expression of one or more markers is selected from the group consisting of cluster of differentiation 44 (CD44), cluster of differentiation 81 (CD81), cluster of differentiation 49e (CD49e), cluster of differentiation 18 (CD18), cluster of differentiation 11b (CD11b), cluster of differentiation 54 (CD54), cluster of differentiation 11c (CD11c), cluster of differentiation 68 (CD68), cluster of differentiation 80 (CD80), cluster of differentiation 86 (CD86), cluster of differentiation 163 (CD163), interleukin 1 receptor (IL-1R), cluster of differentiation 200R (CD200R), chemokine (C—C motif) ligand 10 (CCL10), CCL11, chemokine (C—C motif) ligand 8 (CCL8), chemokine (C—C motif) ligand 9 (CCL9), CCL2, CCL3, CCL4, chemokine (C—C motif) ligand 17 (CCL17), chemokine (C—C motif) ligand 22 (CCL22), chemokine (C—C motif) ligand 24 (CCL24), chemokine (C—C motif) ligand 1 (CCL1), C—C chemokine receptor type 2 (CCR2), CXCL10, CXCL8, chemokine (C—X—C motif) ligand 9 (CXCL9), chemokine (C—X—C motif) ligand 16 (CXCL16), tumor necrosis factor (TNF), IL-1 beta, interleukin 6 (IL-6), interleukin 12 (IL-12), interleukin 23 (IL-23), IL-10, TGF-beta, IL-1RA, interleukin 1 (IL-1), TNF-alpha, and IL-10; and/or decreased expression of one or more of cluster of differentiation 14 (CD 14), lymphocyte antigen 6C (Ly6C), cluster of differentiation 115 (CD115), cluster of differentiation 15s (CD15s), and cluster of differentiation 33 (CD33).

12. The method of claim 1, wherein the cell is an isolated cell.

13. The method of claim 1, wherein the cell is an immune cell.

14. The method of claim 1, wherein the cell is a non-immune cell.

15. The method of claim 1, wherein the method is performed ex vivo or in vitro.

16. The method of claim 1, wherein the IL-40 polypeptide is a human IL-40 polypeptide.

17. The method of claim 1, wherein the IL-40 polypeptide is a mouse IL-40 polypeptide.

* * * * *

SEQUENCE LISTING

```
<160> NUMBER OF SEQ ID NOS: 56

<210> SEQ ID NO 1
<211> LENGTH: 265
<212> TYPE: PRT
<213> ORGANISM: Homo sapiens

<400> SEQUENCE: 1

Met Gly Leu Pro Gly Leu Phe Cys Leu Ala Val Leu Ala Ala Ser Ser
1               5                   10                  15
```

```
Phe Ser Lys Ala Arg Glu Glu Glu Ile Thr Pro Val Val Ser Ile Ala
        20                  25                  30

Tyr Lys Val Leu Glu Val Phe Pro Lys Gly Arg Trp Val Leu Ile Thr
        35                  40                  45

Cys Cys Ala Pro Gln Pro Pro Pro Ile Thr Tyr Ser Leu Cys Gly
        50                  55                  60

Thr Lys Asn Ile Lys Val Ala Lys Lys Val Val Lys Thr His Glu Pro
65                  70                  75                  80

Ala Ser Phe Asn Leu Asn Val Thr Leu Lys Ser Ser Pro Asp Leu Leu
                85                  90                  95

Thr Tyr Phe Cys Trp Ala Ser Ser Thr Ser Gly Ala His Val Asp Ser
            100                 105                 110

Ala Arg Leu Gln Met His Trp Glu Leu Trp Ser Lys Pro Val Ser Glu
        115                 120                 125

Leu Arg Ala Asn Phe Thr Leu Gln Asp Arg Gly Ala Gly Pro Arg Val
        130                 135                 140

Glu Met Ile Cys Gln Ala Ser Ser Gly Ser Pro Pro Ile Thr Asn Ser
145                 150                 155                 160

Leu Ile Gly Lys Asp Gly Gln Val His Leu Gln Gln Arg Pro Cys His
                165                 170                 175

Arg Gln Pro Ala Asn Phe Ser Phe Leu Pro Ser Gln Thr Ser Asp Trp
            180                 185                 190

Phe Trp Cys Gln Ala Ala Asn Asn Ala Asn Val Gln His Ser Ala Leu
            195                 200                 205

Thr Val Val Pro Pro Gly Gly Asp Gln Lys Met Glu Asp Trp Gln Gly
        210                 215                 220

Pro Leu Glu Ser Pro Ile Leu Ala Leu Pro Leu Tyr Arg Ser Thr Arg
225                 230                 235                 240

Arg Leu Ser Glu Glu Glu Phe Gly Gly Phe Arg Ile Gly Asn Gly Glu
                245                 250                 255

Val Arg Gly Arg Lys Ala Ala Ala Met
            260                 265

<210> SEQ ID NO 2
<211> LENGTH: 1090
<212> TYPE: DNA
<213> ORGANISM: Homo sapiens

<400> SEQUENCE: 2
gccaggaact aggaggttct cactgcccga gcagaggccc tacacccacc gaggcatggg      60
gctccctggg ctgttctgct tggccgtgct ggctgccagc agcttctcca aggcacggga     120
ggaagaaatt acccctgtgg tctccattgc ctacaaagtc ctggaagttt tccccaaagg     180
ccgctgggtg ctcataacct gctgtgcacc ccagccacca ccgcccatca cctattccct     240
ctgtggaacc aagaacatca aggtggccaa gaaggtggtg aagacccacg agccggcctc     300
cttcaacctc aacgtcacac tcaagtccag tccagacctg ctcacctact ctgctgggc      360 gtcctccacc tcaggtgccc atgtggacag tgccaggcta cagatgcact gggagctgtg     420
gtccaagcca gtgtctgagc tgcgggccaa cttcactctg caggacagag gggcaggccc     480
cagggtggag atgatctgcc aggcgtcctc gggcagccca cctatcacca acagcctgat     540
cgggaaggat gggcaggtcc acctgcagca gagaccatgc cacaggcagc ctgccaactt     600
ctccttcctg ccgagccaga catcggactg gttctggtgc caggctgcaa acaacgccaa     660
tgtccagcac agcgccctca cagtggtgcc cccaggtggt gaccagaaga tggaggactg     720
```

```
gcagggtccc ctggagagcc ccatccttgc cttgccgctc tacaggagca cccgccgtct      780
gagtgaagag gagtttgggg ggttcaggat agggaatggg gaggtcagag gacgcaaagc      840
agcagccatg tagaatgaac cgtccagaga gccaagcacg gcagaggact gcaggccatc      900
agcgtgcact gttcgtattt ggagttcatg caaaatgagt gtgttttagc tgctcttgcc      960
acaaaaaaaa aaaaaaaaaa aaaagggtaa ctatgagaga tggtggatat gttaacttgc     1020
ttcgctatag gaacctttgt gctatctata ttatctatat gaatcccatc atatcaggtt     1080
gtctacctta                                                            1090
```

<210> SEQ ID NO 3
<211> LENGTH: 252
<212> TYPE: PRT
<213> ORGANISM: Mus musculus

<400> SEQUENCE: 3

```
Met Ala Leu Leu Gln Leu Leu Leu Phe Ala Met Leu Ala Ala Cys Gly
1               5                   10                  15

Phe Ser Glu Glu Gln Thr Glu Gly Ile Thr Ile Ala Tyr Lys Val Leu
                20                  25                  30

Glu Val Tyr Pro Gln Ser Arg Arg Val Leu Ile Thr Cys Asp Ala Pro
            35                  40                  45

Glu Ala Ser Gln Pro Ile Thr Tyr Ser Leu Leu Ala Ser Arg Gly Ile
        50                  55                  60

Leu Val Ala Lys Lys Val Val His Asp Ser Val Pro Ala Ser Phe Asn
65                  70                  75                  80

Ile Asn Ile Thr Ile Lys Ser Ser Pro Asp Leu Leu Thr Tyr Ser Cys
                85                  90                  95

Gln Ala Thr Ser Asn Ser Gly Thr Tyr Gly Pro Ser Ser Arg Leu Gln
            100                 105                 110

Met Tyr Gln Glu Leu Trp Ala Lys Pro Val Ser Gln Leu Gln Ala Asp
        115                 120                 125

Phe Val Leu Arg His Gly Asp Ser Gly Pro Thr Val Glu Leu Ser Cys
    130                 135                 140

Leu Ala Ser Ser Gly Ser Pro Pro Ile Thr Tyr Arg Leu Val Gly Asn
145                 150                 155                 160

Gly Gly Arg Val Leu Ala Gln Gln Arg Pro Leu His Gly Lys Pro Ala
                165                 170                 175

Asn Phe Ser Leu Pro Leu Ser Gln Thr Thr Gly Trp Phe Gln Cys Glu
            180                 185                 190

Ala Glu Asn Asp Val Gly Val Asp Ser Ser Ala Arg Ile Pro Leu Pro
        195                 200                 205

Arg Ala Glu Ala Arg Ala Lys Leu Val Thr Thr Leu Ala Gly Glu Leu
    210                 215                 220

Pro Leu Thr Pro Thr Cys Ile Leu Ala Gly Ser Leu Val Ser Ile Ala
225                 230                 235                 240

Val Ile Ala Ser Arg Met Leu Ser Ser Thr Gly Leu
                245                 250
```

<210> SEQ ID NO 4
<211> LENGTH: 1078
<212> TYPE: DNA
<213> ORGANISM: Mus musculus

<400> SEQUENCE: 4

-continued

```
tagctgcagg cagccacccg aggagcatcc aggggccttg gggtggagag gccagacagg        60
aagctttgga cagcctgagc catacacagc cccaacctca cagacgcatg gcgctccttc       120
agctgctcct ctttgccatg ctggctgcct gtggcttctc agaggagcag acagaaggca       180
tcaccattgc ctacaaagta ctggaagttt atccccaaag ccggagggtg cttataacct       240
gcgatgcccc tgaggcgtcc cagcccatca catactctct cctggctagc cgaggtatcc       300
tggtggcaaa aaaggttgtg catgactccg tgccggcctc cttcaacatc aatatcacca       360
tcaagtccag cccagacctg ctcacctact cctgccaggc aacctcgaac tctggcacct       420
atggacccag cagcaggctc cagatgtacc aggaactgtg ggctaagcca gtgtctcagc       480
tgcaggctga cttcgtccta cgccatgggg actcgggccc cactgtggag ctgtcctgcc       540
tggcatcctc aggcagcccc cccatcacct accgcttggt ggggaatggt gggcgtgttc       600
ttgcacagca aaggccactt catggaaaac agccaacttc tccctcccg ctgtcccaga       660 ccactggttg gttccagtgc gaagctgaaa acgatgtcgg tgtggacagc agtgcccgca       720
tcccgctgcc ccgagcagag gcccgagcca agctggtgac caccctcgca ggggagctgc       780
ccctgacacc cacctgtatt ctggctggca gcctcgtctc catagccgtt attgcttcca       840
ggatgctgag ctcgaccggg ttgtgaccgg aagacagagc catgggcttg cctccctgcc       900
ctgtacaaga acccaccaat ggagcaaaag agagcctgag gtgtgggggt agaaaagggg       960
ggttcagggc tggagagatg gctcagttac agcactgact gttcttccag aggtcccgag      1020
ttcaattccc ataatgtact tctacacata aaataaataa ttcttttttt gttttgtt       1078
```

<210> SEQ ID NO 5
<211> LENGTH: 166
<212> TYPE: PRT
<213> ORGANISM: Homo sapiens
<400> SEQUENCE: 5

```
Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165
```

<210> SEQ ID NO 6

<211> LENGTH: 1211
<212> TYPE: DNA
<213> ORGANISM: Homo sapiens

<400> SEQUENCE: 6

```
acattgttct gatcatctga agatcagcta ttagaagaga aagatcagtt aagtcctttg        60
gacctgatca gcttgataca agaactactg atttcaactt ctttggctta attctctcgg       120
aaacgatgaa atatacaagt tatatcttgg cttttcagct ctgcatcgtt ttgggttctc       180
ttggctgtta ctgccaggac ccatatgtaa aagaagcaga aaaccttaag aaatatttta       240
atgcaggtca ttcagatgta gcggataatg gaactctttt cttaggcatt ttgaagaatt       300
ggaaagagga gagtgacaga aaaataatgc agagccaaat tgtctccttt tacttcaaac       360
tttttaaaaa ctttaaagat gaccagagca tccaaaagag tgtggagacc atcaaggaag       420
acatgaatgt caagtttttc aatagcaaca aaaagaaacg agatgacttc gaaaagctga       480
ctaattattc ggtaactgac ttgaatgtcc aacgcaaagc aatacatgaa ctcatccaag       540
tgatggctga actgtcgcca gcagctaaaa cagggaagca aaaaggagt cagatgctgt        600 ttcgaggtcg aagagcatcc cagtaatggt tgtcctgcct gcaatatttg aattttaaat       660
ctaaatctat ttattaatat ttaacattat ttatatgggg aatatatttt tagactcatc       720
aatcaaataa gtatttataa tagcaacttt tgtgtaatga aaatgaatat ctattaatat       780
atgtattatt tataattcct atatcctgtg actgtctcac ttaatccttt gttttctgac       840
taattaggca aggctatgtg attacaaggc tttatctcag gggccaacta ggcagccaac       900
ctaagcaaga tcccatgggt tgtgtgttta tttcacttga tgatacaatg aacacttata       960
agtgaagtga tactatccag ttactgccgg tttgaaaata tgcctgcaat ctgagccagt      1020
gctttaatgg catgtcagac agaacttgaa tgtgtcaggt gaccctgatg aaaacatagc      1080
atctcaggag atttcatgcc tggtgcttcc aaatattgtt gacaactgtg actgtaccca      1140
aatggaaagt aactcatttg ttaaaattat caatatctaa tatatatgaa taaagtgtaa      1200
gttcacaact a                                                          1211
```

<210> SEQ ID NO 7
<211> LENGTH: 155
<212> TYPE: PRT
<213> ORGANISM: Mus musculus

<400> SEQUENCE: 7

```
Met Asn Ala Thr His Cys Ile Leu Ala Leu Gln Leu Phe Leu Met Ala
1               5                   10                  15

Val Ser Gly Cys Tyr Cys His Gly Thr Val Ile Glu Ser Leu Glu Ser
            20                  25                  30

Leu Asn Asn Tyr Phe Asn Ser Ser Gly Ile Asp Val Glu Glu Lys Ser
        35                  40                  45

Leu Phe Leu Asp Ile Trp Arg Asn Trp Gln Lys Asp Gly Asp Met Lys
    50                  55                  60

Ile Leu Gln Ser Gln Ile Ile Ser Phe Tyr Leu Arg Leu Phe Glu Val
65                  70                  75                  80

Leu Lys Asp Asn Gln Ala Ile Ser Asn Asn Ile Ser Val Ile Glu Ser
                85                  90                  95

His Leu Ile Thr Thr Phe Phe Ser Asn Ser Lys Ala Lys Lys Asp Ala
            100                 105                 110

Phe Met Ser Ile Ala Lys Phe Glu Val Asn Asn Pro Gln Val Gln Arg
            115                 120                 125
```

```
Gln Ala Phe Asn Glu Leu Ile Arg Val Val His Gln Leu Leu Pro Glu
    130                 135                 140

Ser Ser Leu Arg Lys Arg Lys Arg Ser Arg Cys
145                 150                 155

<210> SEQ ID NO 8
<211> LENGTH: 1210
<212> TYPE: DNA
<213> ORGANISM: Mus musculus

<400> SEQUENCE: 8
tatagctgcc atcggctgac ctagagaaga cacatcagct gatcctttgg accctctgac      60
ttgagacaga agttctgggc ttctcctcct gcggcctagc tctgagacaa tgaacgctac     120
acactgcatc ttggctttgc agctcttcct catggctgtt tctggctgtt actgccacgg     180
cacagtcatt gaaagcctag aaagtctgaa taactatttt aactcaagtg gcatagatgt     240
ggaagaaaag agtctcttct tggatatctg gaggaactgg caaaaggatg gtgacatgaa     300
aatcctgcag agccagatta tctctttcta cctcagactc tttgaagtct tgaaagacaa     360
tcaggccatc agcaacaaca taagcgtcat tgaatcacac ctgattacta ccttcttcag     420
caacagcaag gcgaaaaagg atgcattcat gagtattgcc aagtttgagg tcaacaaccc     480
acaggtccag cgccaagcat tcaatgagct catccgagtg gtccaccagc tgttgccgga     540
atccagcctc aggaagcgga aaaggagtcg ctgctgattc ggggtgggga agagattgtc     600
ccaataagaa taattctgcc agcactattt gaattttaa atctaaacct atttattaat     660
atttaaaact atttatatgg agaatctatt ttagatgcat caaccaaaga agtatttata     720
gtaacaactt atatgtgata agagtgaatt cctattaata tatgtgttat ttataatttc     780
tgtctcctca actatttctc tttgaccaat taattattct ttctgactaa ttagccaaga     840
ctgtgattgc ggggttgtat ctgggggtgg gggacagcca agcggctgac tgaactcaga     900
ttgtagcttg tacctttact tcactgacca ataagaaaca ttcagagctg cagtgacccc     960
gggaggtgct gctgatggga ggagatgtct cacctccggg ccagcgcttt aacagcaggc    1020
cagacagcac tcgaatgtgt caggtagtaa caggctgtcc ctgaaagaaa gcagtgtctc    1080
aagagacttg acacctggtg cttccctata cagctgaaaa ctgtgactac acccgaatga    1140
caaataactc gctcatttat agtttatcac tgtctaattg catatgaata aagtatacct    1200
ttgcaaccaa                                                           1210

<210> SEQ ID NO 9
<211> LENGTH: 486
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Leu Ala Arg Glu Glu Glu Ile Thr Pro Val Val Ser Ile Ala Tyr Lys
1               5                   10                  15

Val Leu Glu Val Phe Pro Lys Gly Arg Trp Val Leu Ile Thr Cys Cys
                20                  25                  30

Ala Pro Gln Pro Pro Pro Ile Thr Tyr Ser Leu Cys Gly Thr Lys
        35                  40                  45

Asn Ile Lys Val Ala Lys Lys Val Val Lys Thr His Glu Pro Ala Ser
```

```
        50                  55                   60

Phe Asn Leu Asn Val Thr Leu Lys Ser Ser Pro Asp Leu Leu Thr Tyr
65                  70                  75                  80

Phe Cys Arg Ala Ser Ser Thr Ser Gly Ala His Val Asp Ser Ala Arg
                85                  90                  95

Leu Gln Met His Trp Glu Leu Trp Ser Lys Pro Val Ser Glu Leu Arg
                100                 105                 110

Ala Asn Phe Thr Leu Gln Asp Arg Gly Ala Gly Pro Arg Val Glu Met
            115                 120                 125

Ile Cys Gln Ala Ser Ser Gly Ser Pro Pro Ile Thr Asn Ser Leu Ile
        130                 135                 140

Gly Lys Asp Gly Gln Val His Leu Gln Gln Arg Pro Cys His Arg Gln
145                 150                 155                 160

Pro Ala Asn Phe Ser Phe Leu Pro Ser Gln Thr Ser Asp Trp Phe Trp
                165                 170                 175

Cys Gln Ala Ala Asn Asn Ala Asn Val Gln His Ser Ala Leu Thr Val
            180                 185                 190

Val Pro Pro Gly Gly Asp Gln Lys Met Glu Asp Trp Gln Gly Pro Leu
            195                 200                 205

Glu Ser Pro Ile Leu Ala Leu Pro Leu Tyr Arg Ser Thr Arg Arg Leu
    210                 215                 220

Ser Glu Glu Glu Phe Gly Gly Phe Arg Ile Gly Asn Gly Glu Val Arg
225                 230                 235                 240

Gly Arg Lys Ala Ala Ala Met Ser Arg Ile Glu Gly Arg Met Asp Pro
                245                 250                 255

Lys Ser Cys Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
            275                 280                 285

Thr Leu Met Ile Ser Arg Thr Pro Glu Val Thr Cys Val Val Val Asp
    290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
            355                 360                 365

Ala Pro Ile Glu Lys Thr Ile Ser Lys Ala Lys Gly Gln Pro Arg Glu
    370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
            405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Lys
            435                 440                 445

Leu Thr Val Asp Lys Ser Arg Trp Gln Gln Gly Asn Val Phe Ser Cys
    450                 455                 460

Ser Val Met His Glu Ala Leu His Asn His Tyr Thr Gln Lys Ser Leu
465                 470                 475                 480
```

Ser Leu Ser Pro Gly Lys
            485

<210> SEQ ID NO 10
<211> LENGTH: 1512
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10
atgcccctgc tgctgctgct gcccctgctg tgggccggcg ccctggccct ggctcgggag      60
gaagaaatta ccctgtggt ctccattgcc tacaaagtcc tggaagtttt ccccaaaggc     120
cgctgggtgc tcataacctg ctgtgcaccc cagccaccac cgcccatcac ctattccctc     180
tgtggaacca agaacatcaa ggtggccaag aaggtggtga agacccacga gccggcctcc     240
ttcaacctca acgtcacact caagtccagt ccagacctgc tcacctactt ctgccgggcg     300
tcctccacct caggtgccca tgtggacagt gccaggctac agatgcactg ggagctgtgg     360
tccaagccag tgtctgagct gcgggccaac ttcactctgc aggacagagg ggcaggcccc     420
agggtggaga tgatctgcca ggcgtcctcg ggcagcccac ctatcaccaa cagcctgatc     480
gggaaggatg ggcaggtcca cctgcagcag agaccatgcc acaggcagcc tgccaacttc     540
tccttcctgc cgagccagac atcggactgg ttctggtgcc aggctgcaaa caacgccaat     600
gtccagcaca gcgccctcac agtggtgccc ccaggtggtg accagaagat ggaggactgg     660
cagggtcccc tggagagccc catccttgcc ttgccgctct acaggagcac ccgccgtctg     720
agtgaagagg agtttggggg gttcaggata gggaatgggg aggtcagagg acgcaaagca     780
gcagccatgt ctagaatcga gggccggatg gaccccaagt cctgcgacaa gactcacaca     840
tgcccaccgt gcccagcacc tgaactcctg ggggaccgt cagtcttcct cttcccccca     900
aaacccaagg acaccctcat gatctcccgg acccctgagg tcacatgcgt ggtggtggac     960
gtgagccacg aagaccctga ggtcaagttc aactggtacg tggacggcgt ggaggtgcat    1020
aatgccaaga caaagccgcg ggaggagcag tacaacagca cgtaccgtgt ggtcagcgtc    1080
ctcaccgtcc tgcaccagga ctggctgaat ggcaaggagt acaagtgcaa ggtctccaac    1140
aaagccctcc cagcccccat cgagaaaacc atctccaaag ccaaagggca gccccgagaa    1200
ccacaggtgt acaccctgcc cccatcccgg gatgagctga ccaagaacca ggtcagcctg    1260
acctgcctgg tcaaaggctt ctatcccagc gacatcgccg tggagtggga gagcaatggg    1320
cagccggaga acaactacaa gaccacgcct cccgtgttgg actccgacgg ctccttcttc    1380
ctctacagca agctcaccgt ggacaagagc aggtggcagc aggggaacgt cttctcatgc    1440
tccgtgatgc atgaggctct gcacaaccac tacacgcaga gagcctctc cctgtctccc    1500 gggaataat aa                                                         1512

<210> SEQ ID NO 11
<211> LENGTH: 330
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

-continued

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 12
<211> LENGTH: 153
<212> TYPE: PRT
<213> ORGANISM: Homo sapiens

<400> SEQUENCE: 12
```

```
Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
```

-continued

```
              35                  40                  45
Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
                100                 105                 110

Asn Leu Trp Gly Leu Ala Gly Leu Asn Ser Cys Pro Val Lys Glu Ala
            115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150
```

```
<210> SEQ ID NO 13
<211> LENGTH: 462
<212> TYPE: DNA
<213> ORGANISM: Homo sapiens

<400> SEQUENCE: 13
atgggtctca cctcccaact gcttcccct ctgttcttcc tgctagcatg tgccggcaac      60
tttgtccacg acacaagtg cgatatcacc ttacaggaga tcatcaaaac tttgaacagc     120
ctcacagagc agaagactct gtgcaccgag ttgaccgtaa cagacatctt tgctgcctcc     180
aagaacacaa ctgagaagga aaccttctgc agggctgcga ctgtgctccg gcagttctac     240
agccaccatg agaaggacac tcgctgcctg ggtgcgactg cacagcagtt ccacaggcac     300
aagcagctga tccgattcct gaaacggctc gacaggaacc tctggggcct ggcgggcttg     360
aattcctgtc ctgtgaagga agccaaccag agtacgttgg aaaacttctt ggaaaggcta     420
aagacgatca tgagagagaa atattcaaag tgttcgagct ga                       462
```

```
<210> SEQ ID NO 14
<211> LENGTH: 140
<212> TYPE: PRT
<213> ORGANISM: Mus musculus

<400> SEQUENCE: 14
```

```
Met Gly Leu Asn Pro Gln Leu Val Val Ile Leu Leu Phe Phe Leu Glu
1                   5                   10                  15

Cys Thr Arg Ser His Ile His Gly Cys Asp Lys Asn His Leu Arg Glu
                20                  25                  30

Ile Ile Gly Ile Leu Asn Glu Val Thr Gly Glu Gly Thr Pro Cys Thr
            35                  40                  45

Glu Met Asp Val Pro Asn Val Leu Thr Ala Thr Lys Asn Thr Thr Glu
    50                  55                  60

Ser Glu Leu Val Cys Arg Ala Ser Lys Val Leu Arg Ile Phe Tyr Leu
65                  70                  75                  80

Lys His Gly Lys Thr Pro Cys Leu Lys Lys Asn Ser Ser Val Leu Met
                85                  90                  95

Glu Leu Gln Arg Leu Phe Arg Ala Phe Arg Cys Leu Asp Ser Ser Ile
                100                 105                 110

Ser Cys Thr Met Asn Glu Ser Lys Ser Thr Ser Leu Lys Asp Phe Leu
            115                 120                 125
```

-continued

```
Glu Ser Leu Lys Ser Ile Met Gln Met Asp Tyr Ser
    130                 135                 140

<210> SEQ ID NO 15
<211> LENGTH: 423
<212> TYPE: DNA
<213> ORGANISM: Mus musculus

<400> SEQUENCE: 15
atgggtctca accccagct agttgtcatc ctgctcttct ttctcgaatg taccaggagc        60
catatccacg gatgcgacaa aaatcacttg agagagatca tcggcatttt gaacgaggtc       120
acaggagaag ggacgccatg cacggagatg gatgtgccaa acgtcctcac agcaacgaag       180
aacaccacag agagtgagct cgtctgtagg gcttccaagg tgcttcgcat attttattta       240
aaacatggga aaactccatg cttgaagaag aactctagtg ttctcatgga gctgcagaga       300
ctctttcggg cttttcgatg cctggattca tcgataagct gcaccatgaa tgagtccaag       360
tccacatcac tgaaagactt cctggaaagc ctaaagagca tcatgcaaat ggattactcg       420
tag                                                                     423

<210> SEQ ID NO 16
<211> LENGTH: 178
<212> TYPE: PRT
<213> ORGANISM: Homo sapiens

<400> SEQUENCE: 16

Met His Ser Ser Ala Leu Leu Cys Cys Leu Val Leu Leu Thr Gly Val
1                 5                  10                  15

Arg Ala Ser Pro Gly Gln Gly Thr Gln Ser Glu Asn Ser Cys Thr His
                20                  25                  30

Phe Pro Gly Asn Leu Pro Asn Met Leu Arg Asp Leu Arg Asp Ala Phe
            35                  40                  45

Ser Arg Val Lys Thr Phe Phe Gln Met Lys Asp Gln Leu Asp Asn Leu
        50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 17
<211> LENGTH: 537
<212> TYPE: DNA
<213> ORGANISM: Homo sapiens

<400> SEQUENCE: 17
atgcacagct cagcactgct ctgttgcctg gtcctcctga ctggggtgag ggccagccca        60
```

-continued

```
ggccagggca cccagtctga gaacagctgc acccacttcc caggcaacct gcctaacatg      120
cttcgagatc tccgagatgc cttcagcaga gtgaagactt tctttcaaat gaaggatcag      180
ctggacaact tgttgttaaa ggagtccttg ctggaggact ttaagggtta cctgggttgc      240
caagccttgt ctgagatgat ccagtttttac ctggaggagg tgatgcccca agctgagaac     300
caagacccag acatcaaggc gcatgtgaac tccctggggg agaacctgaa gaccctcagg      360
ctgaggctac ggcgctgtca tcgatttctt ccctgtgaaa acaagagcaa ggccgtggag      420
caggtgaaga tgcctttaa taagctccaa gagaaaggca tctacaaagc catgagtgag      480
tttgacatct tcatcaacta catagaagcc tacatgacaa tgaagatacg aaactga        537
```

<210> SEQ ID NO 18
<211> LENGTH: 178
<212> TYPE: PRT
<213> ORGANISM: Mus musculus

<400> SEQUENCE: 18

```
Met Pro Gly Ser Ala Leu Leu Cys Cys Leu Leu Leu Leu Thr Gly Met
1               5                   10                  15

Arg Ile Ser Arg Gly Gln Tyr Ser Arg Glu Asp Asn Asn Cys Thr His
            20                  25                  30

Phe Pro Val Gly Gln Ser His Met Leu Leu Glu Leu Arg Thr Ala Phe
        35                  40                  45

Ser Gln Val Lys Thr Phe Phe Gln Thr Lys Asp Gln Leu Asp Asn Ile
    50                  55                  60

Leu Leu Thr Asp Ser Leu Met Gln Asp Phe Lys Gly Tyr Leu Gly Cys
65                  70                  75                  80

Gln Ala Leu Ser Glu Met Ile Gln Phe Tyr Leu Val Glu Val Met Pro
                85                  90                  95

Gln Ala Glu Lys His Gly Pro Glu Ile Lys Glu His Leu Asn Ser Leu
            100                 105                 110

Gly Glu Lys Leu Lys Thr Leu Arg Met Arg Leu Arg Arg Cys His Arg
        115                 120                 125

Phe Leu Pro Cys Glu Asn Lys Ser Lys Ala Val Glu Gln Val Lys Ser
    130                 135                 140

Asp Phe Asn Lys Leu Gln Asp Gln Gly Val Tyr Lys Ala Met Asn Glu
145                 150                 155                 160

Phe Asp Ile Phe Ile Asn Cys Ile Glu Ala Tyr Met Met Ile Lys Met
                165                 170                 175

Lys Ser
```

<210> SEQ ID NO 19
<211> LENGTH: 537
<212> TYPE: DNA
<213> ORGANISM: Mus musculus

<400> SEQUENCE: 19

```
atgcctggct cagcactgct atgctgcctg ctcttactga ctggcatgag gatcagcagg       60
ggccagtaca gccgggaaga caataactgc acccacttcc cagtcggcca gagccacatg      120
ctcctagagc tgcggactgc cttcagccag gtgaagactt tctttcaaac aaaggaccag      180
ctggacaaca tactgctaac cgactcctta atgcaggact ttaagggtta cttgggttgc      240
caagccttat cggaaatgat ccagtttttac ctggtagaag tgatgcccca ggcagagaag     300
catggcccag aaatcaagga gcatttgaat tccctgggtg agaagctgaa gaccctcagg      360
```

```
atgcggctga ggcgctgtca tcgatttctc ccctgtgaaa ataagagcaa ggcagtggag      420
caggtgaaga gtgattttaa taagctccaa gaccaaggtg tctacaaggc catgaatgaa      480
tttgacatct tcatcaactg catagaagca tacatgatga tcaaaatgaa aagctaa        537
```

```
<210> SEQ ID NO 20
<211> LENGTH: 390
<212> TYPE: PRT
<213> ORGANISM: Homo sapiens

<400> SEQUENCE: 20

Met Pro Pro Ser Gly Leu Arg Leu Leu Pro Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Arg Ile Glu Ala
        35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
            115                 120                 125

His Ser Ile Tyr Met Phe Phe Asn Thr Ser Glu Leu Arg Glu Ala Val
        130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
            180                 185                 190

Pro Glu Trp Leu Ser Phe Asp Val Thr Gly Val Val Arg Gln Trp Leu
            195                 200                 205

Ser Arg Gly Gly Glu Ile Glu Gly Phe Arg Leu Ser Ala His Cys Ser
    210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
                245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
        290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
            325                 330                 335

Ser Lys Val Leu Ala Leu Tyr Asn Gln His Asn Pro Gly Ala Ser Ala
```

-continued

```
                340               345               350
Ala Pro Cys Cys Val Pro Gln Ala Leu Glu Pro Leu Pro Ile Val Tyr
            355               360               365
Tyr Val Gly Arg Lys Pro Lys Val Glu Gln Leu Ser Asn Met Ile Val
        370               375               380
Arg Ser Cys Lys Cys Ser
385               390
```

```
<210> SEQ ID NO 21
<211> LENGTH: 1173
<212> TYPE: DNA
<213> ORGANISM: Homo sapiens

<400> SEQUENCE: 21
atgccgccct ccgggctgcg gctgctgccg ctgctgctac cgctgctgtg gctactggtg     60
ctgacgcctg gccggccggc cgcgggacta tccacctgca agactatcga catggagctg    120
gtgaagcgga agcgcatcga ggccatccgc ggccagatcc tgtccaagct gcggctcgcc    180
agccccccga gccagggga ggtgccgccc ggcccgctgc ccgaggccgt gctcgccctg    240
tacaacagca cccgcgaccg ggtggccggg gagagtgcag aaccggagcc cgagcctgag    300
gccgactact acgccaagga ggtcacccgc gtgctaatgg tggaaaccca caacgaaatc    360
tatgacaagt tcaagcagag tacacacagc atatatatgt tcttcaacac atcagagctc    420
cgagaagcgg tacctgaacc cgtgttgctc tcccgggcag agctgcgtct gctgaggctc    480
aagttaaaag tggagcagca cgtggagctg taccagaaat acagcaacaa ttcctggcga    540
tacctcagca accggctgct ggcacccagc gactcgccag agtggttatc ttttgatgtc    600
accggagttg tgcggcagtg gttgagccgt ggaggggaaa ttgagggctt cgccttagc    660 gcccactgct cctgtgacag cagggataac acactgcaag tggacatcaa cgggttcact    720
accggccgcc gaggtgacct ggccaccatt catggcatga accggccttt cctgcttctc    780
atggccaccc cgctggagag ggcccagcat ctgcaaagct cccggcaccg ccgagccctg    840
gacaccaact attgcttcag ctccacggag aagaactgct gcgtgcggca gctgtacatt    900
gacttccgca aggacctcgg ctggaagtgg atccacgagc ccaggggcta ccatgccaac    960
ttctgcctcg ggccctgccc ctacatttgg agcctggaca cgcagtacag caaggtcctg   1020
gccctgtaca accagcataa cccgggcgcc tcggcggcgc cgtgctgcgt gccgcaggcg   1080
ctggagccgc tgcccatcgt gtactacgtg ggccgcaagc ccaaggtgga gcagctgtcc   1140
aacatgatcg tgcgctcctg caagtgcagc tga                                1173
```

```
<210> SEQ ID NO 22
<211> LENGTH: 390
<212> TYPE: PRT
<213> ORGANISM: Mus musculus

<400> SEQUENCE: 22

Met Pro Pro Ser Gly Leu Arg Leu Leu Pro Leu Leu Leu Pro Leu Pro
1               5               10               15
Trp Leu Leu Val Leu Thr Pro Gly Arg Pro Ala Ala Gly Leu Ser Thr
            20               25               30
Cys Lys Thr Ile Asp Met Glu Leu Val Lys Arg Lys Arg Ile Glu Ala
        35               40               45
Ile Arg Gly Gln Ile Leu Ser Lys Leu Arg Leu Ala Ser Pro Pro Ser
    50               55               60
```

```
Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Asp Pro Glu
                85                  90                  95

Pro Glu Pro Glu Ala Asp Tyr Tyr Ala Lys Glu Val Thr Arg Val Leu
            100                 105                 110

Met Val Asp Arg Asn Asn Ala Ile Tyr Glu Lys Thr Lys Asp Ile Ser
        115                 120                 125

His Ser Ile Tyr Met Phe Phe Asn Thr Ser Asp Ile Arg Glu Ala Val
        130                 135                 140

Pro Glu Pro Pro Leu Leu Ser Arg Ala Glu Leu Arg Leu Gln Arg Leu
145                 150                 155                 160

Lys Ser Ser Val Glu Gln His Val Glu Leu Tyr Gln Lys Tyr Ser Asn
                165                 170                 175

Asn Ser Trp Arg Tyr Leu Gly Asn Arg Leu Leu Thr Pro Thr Asp Thr
            180                 185                 190

Pro Glu Trp Leu Ser Phe Asp Val Thr Gly Val Val Arg Gln Trp Leu
        195                 200                 205

Asn Gln Gly Asp Gly Ile Gln Gly Phe Arg Phe Ser Ala His Cys Ser
        210                 215                 220

Cys Asp Ser Lys Asp Asn Lys Leu His Val Glu Ile Asn Gly Ile Ser
225                 230                 235                 240

Pro Lys Arg Arg Gly Asp Leu Gly Thr Ile His Asp Met Asn Arg Pro
            245                 250                 255

Phe Leu Leu Leu Met Ala Thr Pro Leu Glu Arg Ala Gln His Leu His
        260                 265                 270

Ser Ser Arg His Arg Arg Ala Leu Asp Thr Asn Tyr Cys Phe Ser Ser
        275                 280                 285

Thr Glu Lys Asn Cys Cys Val Arg Gln Leu Tyr Ile Asp Phe Arg Lys
        290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
            325                 330                 335

Ser Lys Val Leu Ala Leu Tyr Asn Gln His Asn Pro Gly Ala Ser Ala
            340                 345                 350

Ser Pro Cys Cys Val Pro Gln Ala Leu Glu Pro Leu Pro Ile Val Tyr
        355                 360                 365

Tyr Val Gly Arg Lys Pro Lys Val Glu Gln Leu Ser Asn Met Ile Val
    370                 375                 380

Arg Ser Cys Lys Cys Ser
385                 390

<210> SEQ ID NO 23
<211> LENGTH: 1173
<212> TYPE: DNA
<213> ORGANISM: Mus musculus

<400> SEQUENCE: 23
atgccgccct cggggctgcg gctactgccg cttctgctcc cactcccgtg gcttctagtg      60
ctgacgcccg ggaggccagc cgcgggactc tccacctgca agaccatcga catggagctg     120
gtgaaacgga agcgcatcga agccatccgt ggccagatcc tgtccaaact aaggctcgcc     180
agtcccccaa gccagggggga ggtaccgccc ggcccgctgc ccgaggcggt gctcgctttg     240
```

-continued

| | | | | |
|---|---|---|---|---|
| tacaacagca | cccgcgaccg | ggtggcaggc | gagagcgccg | acccagagcc ggagcccgaa | 300 |
| gcggactact | atgctaaaga | ggtcacccgc | gtgctaatgg | tggaccgcaa caacgccatc | 360 |
| tatgagaaaa | ccaaagacat | ctcacacagt | atatatatgt | tcttcaatac gtcagacatt | 420 |
| cgggaagcag | tgcccgaacc | cccattgctg | tcccgtgcag | agctgcgctt gcagagatta | 480 |
| aaatcaagtg | tggagcaaca | tgtggaactc | taccagaaat | atagcaacaa ttcctggcgt | 540 |
| taccttggta | accggctgct | gaccccccact | gatacgcctg | agtggctgtc ttttgacgtc | 600 |
| actggagttg | tacggcagtg | gctgaaccaa | ggagacggaa | tacagggctt tcgattcagc | 660 |
| gctcactgct | cttgtgacag | caaagataac | aaactccacg | tggaaatcaa cgggatcagc | 720 |
| cccaaacgtc | ggggcgacct | gggcaccatc | catgacatga | accggccctt cctgctcctc | 780 |
| atggccaccc | ccctggaaag | ggcccagcac | ctgcacagct | cacggcaccg gagagccctg | 840 |
| gataccaact | attgcttcag | ctccacagag | aagaactgct | gtgtgcggca gctgtacatt | 900 |
| gactttagga | aggacctggg | ttggaagtgg | atccacgagc | ccaagggcta ccatgccaac | 960 |
| ttctgtctgg | accctgccc | ctatatttgg | agcctggaca | cacagtacag caaggtcctt | 1020 |
| gccctctaca | accaacacaa | cccgggcgct | tcggcgtcac | cgtgctgcgt gccgcaggct | 1080 |
| ttggagccac | tgcccatcgt | ctactacgtg | ggtcgcaagc | ccaaggtgga gcagttgtcc | 1140 |
| aacatgattg | tgcgctcctg | caagtgcagc | tga | | 1173 |

```
<210> SEQ ID NO 24
<211> LENGTH: 144
<212> TYPE: PRT
<213> ORGANISM: Homo sapiens

<400> SEQUENCE: 24

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
            85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 25
<211> LENGTH: 788
<212> TYPE: DNA
<213> ORGANISM: Homo sapiens

<400> SEQUENCE: 25
```

| | | | | |
|---|---|---|---|---|
| agtacacaga | gagaaaggct | aaagttctct | ggaggatgtg | gctgcagagc ctgctgctct | 60 |
| tgggcactgt | ggcctgcagc | atctctgcac | ccgcccgctc | gcccagcccc agcacgcagc | 120 |

-continued

```
cctgggagca tgtgaatgcc atccaggagg cccggcgtct cctgaacctg agtagagaca      180
ctgctgctga gatgaatgaa acagtagaag tcatctcaga aatgtttgac ctccaggagc      240
cgacctgcct acagacccgc ctggagctgt acaagcaggg cctgcggggc agcctcacca      300
agctcaaggg cccccttgacc atgatggcca gccactacaa gcagcactgc cctccaaccc      360
cggaaacttc ctgtgcaacc cagattatca cctttgaaag tttcaaagag aacctgaagg      420
actttctgct tgtcatcccc tttgactgct gggagccagt ccaggagtga gaccggccag      480
atgaggctgg ccaagccggg gagctgctct ctcatgaaac aagagctaga aactcaggat      540
ggtcatcttg gagggaccaa ggggtgggcc acagccatgg tgggagtggc ctggacctgc      600
cctgggccac actgaccctg atacaggcat ggcagaagaa tgggaatatt ttatactgac      660
agaaatcagt aatatttata tatttatatt tttaaaatat ttatttattt atttatttaa      720
gttcatattc catatttatt caagatgttt taccgtaata attattatta aaaatatgct      780
tctacttg                                                              788
```

```
<210> SEQ ID NO 26
<211> LENGTH: 141
<212> TYPE: PRT
<213> ORGANISM: Mus musculus

<400> SEQUENCE: 26

Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
            20                  25                  30

Val Glu Ala Ile Lys Glu Ala Leu Asn Leu Leu Asp Asp Met Pro Val
        35                  40                  45

Thr Leu Asn Glu Glu Val Glu Val Val Ser Asn Glu Phe Ser Phe Lys
    50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Ile Pro Phe Glu Cys Lys Lys Pro Gly Gln Lys
    130                 135                 140
```

```
<210> SEQ ID NO 27
<211> LENGTH: 426
<212> TYPE: DNA
<213> ORGANISM: Mus musculus

<400> SEQUENCE: 27
atgtggctgc agaatttact tttcctgggc attgtggtct acagcctctc agcacccacc       60
cgctcaccca tcactgtcac ccggccttgg aagcatgtag aggccatcaa agaagccctg      120
aacctcctgg atgacatgcc tgtcacgttg aatgaagagg tagaagtcgt ctctaacgag      180
ttctccttca gaagctaac atgtgtgcag acccgcctga gatattcga gcagggtcta       240 cggggcaatt tcaccaaact caagggcgcc ttgaacatga gccagcta ctaccagaca       300 tactgcccc caactccgga aacggactgt gaaacacaag ttaccaccta tgcggatttc      360
```

-continued atagacagcc ttaaaacctt tctgactgat atcccctttg aatgcaaaaa accaggccaa        420
aaatga                                                                   426

<210> SEQ ID NO 28
<211> LENGTH: 554
<212> TYPE: PRT
<213> ORGANISM: Homo sapiens

<400> SEQUENCE: 28

Met Thr Ala Pro Gly Ala Ala Gly Arg Cys Pro Pro Thr Thr Trp Leu
1               5                   10                  15

Gly Ser Leu Leu Leu Leu Val Cys Leu Leu Ala Ser Arg Ser Ile Thr
            20                  25                  30

Glu Glu Val Ser Glu Tyr Cys Ser His Met Ile Gly Ser Gly His Leu
        35                  40                  45

Gln Ser Leu Gln Arg Leu Ile Asp Ser Gln Met Glu Thr Ser Cys Gln
    50                  55                  60

Ile Thr Phe Glu Phe Val Asp Gln Glu Gln Leu Lys Asp Pro Val Cys
65                  70                  75                  80

Tyr Leu Lys Lys Ala Phe Leu Leu Val Gln Asp Ile Met Glu Asp Thr
                85                  90                  95

Met Arg Phe Arg Asp Asn Thr Pro Asn Ala Ile Ala Ile Val Gln Leu
            100                 105                 110

Gln Glu Leu Ser Leu Arg Leu Lys Ser Cys Phe Thr Lys Asp Tyr Glu
        115                 120                 125

Glu His Asp Lys Ala Cys Val Arg Thr Phe Tyr Glu Thr Pro Leu Gln
    130                 135                 140

Leu Leu Glu Lys Val Lys Asn Val Phe Asn Glu Thr Lys Asn Leu Leu
145                 150                 155                 160

Asp Lys Asp Trp Asn Ile Phe Ser Lys Asn Cys Asn Asn Ser Phe Ala
                165                 170                 175

Glu Cys Ser Ser Gln Asp Val Val Thr Lys Pro Asp Cys Asn Cys Leu
            180                 185                 190

Tyr Pro Lys Ala Ile Pro Ser Ser Asp Pro Ala Ser Val Ser Pro His
        195                 200                 205

Gln Pro Leu Ala Pro Ser Met Ala Pro Val Ala Gly Leu Thr Trp Glu
    210                 215                 220

Asp Ser Glu Gly Thr Glu Gly Ser Ser Leu Leu Pro Gly Glu Gln Pro
225                 230                 235                 240

Leu His Thr Val Asp Pro Gly Ser Ala Lys Gln Arg Pro Pro Arg Ser
                245                 250                 255

Thr Cys Gln Ser Phe Glu Pro Pro Glu Thr Pro Val Val Lys Asp Ser
            260                 265                 270

Thr Ile Gly Gly Ser Pro Gln Pro Arg Pro Ser Val Gly Ala Phe Asn
        275                 280                 285

Pro Gly Met Glu Asp Ile Leu Asp Ser Ala Met Gly Thr Asn Trp Val
    290                 295                 300

Pro Glu Glu Ala Ser Gly Glu Ala Ser Glu Ile Pro Val Pro Gln Gly
305                 310                 315                 320

Thr Glu Leu Ser Pro Ser Arg Pro Gly Gly Gly Ser Met Gln Thr Glu
                325                 330                 335

Pro Ala Arg Pro Ser Asn Phe Leu Ser Ala Ser Ser Pro Leu Pro Ala
            340                 345                 350

Ser Ala Lys Gly Gln Gln Pro Ala Asp Val Thr Gly Thr Ala Leu Pro

-continued

```
              355                 360                 365
Arg Val Gly Pro Val Arg Pro Thr Gly Gln Asp Trp Asn His Thr Pro
    370                 375                 380
Gln Lys Thr Asp His Pro Ser Ala Leu Leu Arg Asp Pro Pro Glu Pro
385                 390                 395                 400
Gly Ser Pro Arg Ile Ser Ser Leu Arg Pro Gln Gly Leu Ser Asn Pro
                405                 410                 415
Ser Thr Leu Ser Ala Gln Pro Gln Leu Ser Arg Ser His Ser Ser Gly
                420                 425                 430
Ser Val Leu Pro Leu Gly Glu Leu Glu Gly Arg Arg Ser Thr Arg Asp
                435                 440                 445
Arg Arg Ser Pro Ala Glu Pro Glu Gly Gly Pro Ala Ser Glu Gly Ala
    450                 455                 460
Ala Arg Pro Leu Pro Arg Phe Asn Ser Val Pro Leu Thr Asp Thr Gly
465                 470                 475                 480
His Glu Arg Gln Ser Glu Gly Ser Phe Ser Pro Gln Leu Gln Glu Ser
                485                 490                 495
Val Phe His Leu Leu Val Pro Ser Val Ile Leu Val Leu Leu Ala Val
                500                 505                 510
Gly Gly Leu Leu Phe Tyr Arg Trp Arg Arg Arg Ser His Gln Glu Pro
                515                 520                 525
Gln Arg Ala Asp Ser Pro Leu Glu Gln Pro Glu Gly Ser Pro Leu Thr
    530                 535                 540
Gln Asp Asp Arg Gln Val Glu Leu Pro Val
545                 550
```

```
<210> SEQ ID NO 29
<211> LENGTH: 1665
<212> TYPE: DNA
<213> ORGANISM: Homo sapiens

<400> SEQUENCE: 29
atgaccgcgc cgggcgccgc cgggcgctgc cctcccacga catggctggg ctccctgctg      60
ttgttggtct gtctcctggc gagcaggagt atcaccgagg aggtgtcgga gtactgtagc     120
cacatgattg ggagtggaca cctgcagtct ctgcagcggc tgattgacag tcagatggag     180
acctcgtgcc aaattacatt tgagtttgta gaccaggaac agttgaaaga tccagtgtgc     240
taccttaaga aggcatttct cctggtacaa gacataatgg aggacaccat cgcgcttcaga     300 gataacaccc ccaatgccat cgccattgtg cagctgcagg aactctcttt gaggctgaag     360
agctgcttca ccaaggatta tgaagagcat gacaaggcct gcgtccgaac tttctatgag     420
acacctctcc agttgctgga aaggtcaag aatgtcttta atgaaacaaa gaatctcctt     480
gacaaggact ggaatatttt cagcaagaac tgcaacaaca gctttgctga atgctccagc     540
caagatgtgg tgaccaagcc tgattgcaac tgcctgtacc ccaaagccat ccctagcagt     600
gacccggcct ctgtctcccc tcatcagccc ctcgcccct ccatggcccc tgtggctggc     660
ttgacctggg aggactctga gggaactgag ggcagctccc tcttgcctgg tgagcagccc     720
ctgcacacag tggatccagg cagtgccaag cagcggccac ccaggagcac ctgccagagc     780
tttgagccgc cagagacccc agttgtcaag gacagcacca tcggtggctc accacagcct     840 cgccctctg tcgggccctt caaccccggg atggaggata ttcttgactc tgcaatgggc     900
actaattggg tcccagaaga agcctctgga gaggccagtg agattcccgt accccaaggg     960
acagagcttt cccctccag gccaggaggg ggcagcatgc agacagagcc cgccagaccc    1020
```

```
agcaacttcc tctcagcatc ttctccactc cctgcatcag caaagggcca acagccggca    1080
gatgtaactg gtaccgcctt gcccagggtg ggccccgtga ggcccactgg ccaggactgg    1140
aatcacaccc cccagaagac agaccatcca tctgccctgc tcagagaccc cccggagcca    1200
ggctctccca ggatctcatc actgcgcccc cagggcctca gcaacccctc caccctctct    1260
gctcagccac agctttccag aagccactcc tcgggcagcg tgctgcccct tggggagctg    1320
gagggcagga ggagcaccag ggatcggagg agccccgcag agccagaagg aggaccagca    1380
agtgaagggg cagccaggcc cctgccccgt tttaactccg ttcctttgac tgacacaggc    1440
catgagaggc agtccgaggg atccttcagc ccgcagctcc aggagtctgt cttccacctg    1500
ctggtgccca gtgtcatcct ggtcttgctg ccgtcggag gcctcttgtt ctacaggtgg    1560
aggcggcgga gccatcaaga gcctcagaga gcggattctc ccttggagca accagagggc    1620
agccccctga ctcaggatga cagacaggtg gaactgccag tgtag                    1665
```

<210> SEQ ID NO 30
<211> LENGTH: 552
<212> TYPE: PRT
<213> ORGANISM: Mus musculus

<400> SEQUENCE: 30

```
Met Thr Ala Arg Gly Ala Ala Gly Arg Cys Pro Ser Ser Thr Trp Leu
1               5                   10                  15

Gly Ser Arg Leu Leu Leu Val Cys Leu Leu Met Ser Arg Ser Ile Ala
            20                  25                  30

Lys Glu Val Ser Glu His Cys Ser His Met Ile Gly Asn Gly His Leu
        35                  40                  45

Lys Val Leu Gln Gln Leu Ile Asp Ser Gln Met Glu Thr Ser Cys Gln
    50                  55                  60

Ile Ala Phe Glu Phe Val Asp Gln Glu Gln Leu Asp Asp Pro Val Cys
65                  70                  75                  80

Tyr Leu Lys Lys Ala Phe Phe Leu Val Gln Asp Ile Ile Asp Glu Thr
                85                  90                  95

Met Arg Phe Lys Asp Asn Thr Pro Asn Ala Asn Ala Thr Glu Arg Leu
            100                 105                 110

Gln Glu Leu Ser Asn Asn Leu Asn Ser Cys Phe Thr Lys Asp Tyr Glu
        115                 120                 125

Glu Gln Asn Lys Ala Cys Val Arg Thr Phe His Glu Thr Pro Leu Gln
    130                 135                 140

Leu Leu Glu Lys Ile Lys Asn Phe Phe Asn Glu Thr Lys Asn Leu Leu
145                 150                 155                 160

Glu Lys Asp Trp Asn Ile Phe Thr Lys Asn Cys Asn Asn Ser Phe Ala
                165                 170                 175

Lys Cys Ser Ser Arg Asp Val Val Thr Lys Pro Asp Cys Asn Cys Leu
            180                 185                 190

Tyr Pro Lys Ala Thr Pro Ser Ser Asp Pro Ala Ser Ala Ser Pro His
        195                 200                 205

Gln Pro Pro Ala Pro Ser Met Ala Pro Leu Ala Gly Leu Ala Trp Asp
    210                 215                 220

Asp Ser Gln Arg Thr Glu Gly Ser Ser Leu Leu Pro Ser Glu Leu Pro
225                 230                 235                 240

Leu Arg Ile Glu Asp Pro Gly Ser Ala Lys Gln Arg Pro Pro Arg Ser
                245                 250                 255
```

-continued

```
Thr Cys Gln Thr Leu Glu Ser Thr Glu Gln Pro Asn His Gly Asp Arg
            260                 265                 270

Leu Thr Glu Asp Ser Gln Pro His Pro Ser Ala Gly Gly Pro Val Pro
        275                 280                 285

Gly Val Glu Asp Ile Leu Glu Ser Ser Leu Gly Thr Asn Trp Val Leu
        290                 295                 300

Glu Glu Ala Ser Gly Glu Ala Ser Glu Gly Phe Leu Thr Gln Glu Ala
305                 310                 315                 320

Lys Phe Ser Pro Ser Thr Pro Val Gly Gly Ser Ile Gln Ala Glu Thr
                325                 330                 335

Asp Arg Pro Arg Ala Leu Ser Ala Ser Pro Phe Pro Lys Ser Thr Glu
            340                 345                 350

Asp Gln Lys Pro Val Asp Ile Thr Asp Arg Pro Leu Thr Glu Val Asn
        355                 360                 365

Pro Met Arg Pro Ile Gly Gln Thr Gln Asn Asn Thr Pro Glu Lys Thr
        370                 375                 380

Asp Gly Thr Ser Thr Leu Arg Glu Asp His Gln Glu Pro Gly Ser Pro
385                 390                 395                 400

His Ile Ala Thr Pro Asn Pro Gln Arg Val Ser Asn Ser Ala Thr Pro
                405                 410                 415

Val Ala Gln Leu Leu Leu Pro Lys Ser His Ser Trp Gly Ile Val Leu
            420                 425                 430

Pro Leu Gly Glu Leu Glu Gly Lys Arg Ser Thr Arg Asp Arg Arg Ser
        435                 440                 445

Pro Ala Glu Leu Glu Gly Gly Ser Ala Ser Glu Gly Ala Ala Arg Pro
        450                 455                 460

Val Ala Arg Phe Asn Ser Ile Pro Leu Thr Asp Thr Gly His Val Glu
465                 470                 475                 480

Gln His Glu Gly Ser Ser Asp Pro Gln Ile Pro Glu Ser Val Phe His
                485                 490                 495

Leu Leu Val Pro Gly Ile Ile Leu Val Leu Leu Thr Val Gly Gly Leu
            500                 505                 510

Leu Phe Tyr Lys Trp Lys Trp Arg Ser His Arg Asp Pro Gln Thr Leu
            515                 520                 525

Asp Ser Ser Val Gly Arg Pro Glu Asp Ser Ser Leu Thr Gln Asp Glu
        530                 535                 540

Asp Arg Gln Val Glu Leu Pro Val
545                 550

<210> SEQ ID NO 31
<211> LENGTH: 1659
<212> TYPE: DNA
<213> ORGANISM: Mus musculus

<400> SEQUENCE: 31
atgaccgcgc ggggcgccgc ggggcgctgc ccttcttcga catggctggg ctcccggctg      60
ctgctggtct gtctcctcat gagcaggagt attgccaagg aggtgtcaga acactgtagc     120
cacatgattg ggaatggaca cctgaaggtc ctgcagcagt tgatcgacag tcaaatggag     180
acttcatgcc agattgcctt tgaatttgta gaccaggaac agctggatga tcctgtttgc     240
tacctaaaga aggccttttt tctggtacaa gacataatag atgagaccat gcgctttaaa     300
gacaacaccc ccaatgctaa cgccaccgag aggctccagg aactctccaa taacctgaac     360
agctgcttca ccaaggacta tgaggagcag aacaaggcct gtgtccgaac tttccatgag     420
```

-continued

```
actcctctcc agctgctgga gaagatcaag aacttcttta atgaaacaaa gaatctcctt    480
gaaaaggact ggaacatttt taccaagaac tgcaacaaca gctttgctaa gtgctctagc    540
cgagatgtgg tgaccaagcc tgattgcaac tgcctgtacc ctaaagccac ccctagcagt    600 gaccggcct ctgcctcccc tcaccagccc ccgcccct ccatggcccc tctggctggc    660
ttggcttggg atgattctca gaggacagag ggcagctccc tcttgcccag tgagcttccc    720
cttcgcatag aggacccagg cagtgccaag cagcgaccac ccaggagtac ctgccagacc    780
ctcgagtcaa cagagcaacc aaaccatggg gacagactca ctgaggactc acaacctcat    840
ccttctgcgg gggggcccgt ccctggggtg gaagacattc ttgaatcttc actgggcact    900
aactgggtcc tagaagaagc ttctggagag gctagtgagg gatttttgac ccaggaagca    960
aagttttccc cctccacgcc tgtagggggc agcatccagg cagagactga cagacccagg   1020
gccctctcag catctccatt ccctaaatca acagaggacc aaaagccagt ggatataaca   1080
gacaggccgt tgacagaggt gaaccctatg agacccattg ccagacaca gaataatact   1140 cctgagaaga ctgatggtac atccacgctg cgtgaagacc accaggagcc aggctctccc   1200
catattgcga caccgaatcc ccaacgagtc agcaactcag ccacccccgt tgctcagtta   1260
ctgcttccca aaagccactc ttggggcatt gtgctgcccc ttggggagct tgagggcaag   1320
agaagtacca gggatcgaag gagccccgca gagctggaag gaggatcagc aagtgagggg   1380
gcagccaggc ctgtggcccg ttttaattcc attcctttga ctgacacagg ccatgtggag   1440
cagcatgagg gatcctctga cccccagatc cctgagtctg tcttccacct gctggtgccg   1500
ggcatcatcc tagtcttgct gactgttggg ggcctcctgt tctacaagtg gaagtggagg   1560
agccatcgag accctcagac attggattct tctgtggggc gaccagagga cagctccctg   1620
acccaggatg aggacagaca ggtggaactg ccagtatag                          1659
```

<210> SEQ ID NO 32
<211> LENGTH: 188
<212> TYPE: PRT
<213> ORGANISM: Homo sapiens

<400> SEQUENCE: 32

```
Met Ala Leu Thr Phe Ala Leu Leu Val Ala Leu Leu Val Leu Ser Cys
1               5                   10                  15

Lys Ser Ser Cys Ser Val Gly Cys Asp Leu Pro Gln Thr His Ser Leu
            20                  25                  30

Gly Ser Arg Arg Thr Leu Met Leu Leu Ala Gln Met Arg Arg Ile Ser
        35                  40                  45

Leu Phe Ser Cys Leu Lys Asp Arg His Asp Phe Gly Phe Pro Gln Glu
    50                  55                  60

Glu Phe Gly Asn Gln Phe Gln Lys Ala Glu Thr Ile Pro Val Leu His
65                  70                  75                  80

Glu Met Ile Gln Gln Ile Phe Asn Leu Phe Ser Thr Lys Asp Ser Ser
                85                  90                  95

Ala Ala Trp Asp Glu Thr Leu Leu Asp Lys Phe Tyr Thr Glu Leu Tyr
            100                 105                 110

Gln Gln Leu Asn Asp Leu Glu Ala Cys Val Ile Gln Gly Val Gly Val
        115                 120                 125

Thr Glu Thr Pro Leu Met Lys Glu Asp Ser Ile Leu Ala Val Arg Lys
    130                 135                 140

Tyr Phe Gln Arg Ile Thr Leu Tyr Leu Lys Glu Lys Lys Tyr Ser Pro
145                 150                 155                 160
```

```
Cys Ala Trp Glu Val Val Arg Ala Glu Ile Met Arg Ser Phe Ser Leu
                165                 170                 175

Ser Thr Asn Leu Gln Glu Ser Leu Arg Ser Lys Glu
            180                 185

<210> SEQ ID NO 33
<211> LENGTH: 567
<212> TYPE: DNA
<213> ORGANISM: Homo sapiens

<400> SEQUENCE: 33
atggccttga cctttgcttt actggtggcc ctcctggtgc tcagctgcaa gtcaagctgc     60
tctgtgggct gtgatctgcc tcaaacccac agcctgggta gcaggaggac cttgatgctc    120
ctggcacaga tgaggagaat ctctcttttc tcctgcttga aggacagaca tgactttgga    180
tttccccagg aggagtttgg caaccagttc caaaaggctg aaaccatccc tgtcctccat    240
gagatgatcc agcagatctt caatctcttc agcacaaagg actcatctgc tgcttgggat    300
gagaccctcc tagacaaatt ctacactgaa ctctaccagc agctgaatga cctggaagcc    360
tgtgtgatac agggggtggg ggtgacagag actcccctga tgaaggagga ctccattctg    420
gctgtgagga atacttcca aagaatcact ctctatctga agagaagaa atacagccct       480 tgtgcctggg aggttgtcag agcagaaatc atgagatctt tttctttgtc aacaaacttg     540
caagaaagtt taagaagtaa ggaatga                                        567

<210> SEQ ID NO 34
<211> LENGTH: 190
<212> TYPE: PRT
<213> ORGANISM: Mus musculus

<400> SEQUENCE: 34

Met Ala Arg Leu Cys Ala Phe Leu Met Thr Leu Leu Val Met Ser Tyr
1                5                  10                  15

Trp Ser Thr Cys Ser Leu Gly Cys Asp Leu Pro Gln Thr His Asn Leu
                20                  25                  30

Arg Asn Lys Arg Ala Leu Thr Leu Leu Val Gln Met Arg Arg Leu Ser
            35                  40                  45

Pro Leu Ser Cys Leu Lys Asp Arg Lys Asp Phe Arg Phe Pro Gln Glu
        50                  55                  60

Lys Val Asp Ala Gln Gln Ile Gln Asn Ala Gln Ala Ile Pro Val Leu
65                  70                  75                  80

Gln Glu Leu Thr Gln Gln Val Leu Asn Ile Phe Thr Ser Lys Asp Ser
                85                  90                  95

Ser Ala Ala Trp Asp Ala Ser Leu Leu Asp Ser Phe Cys Asn Asp Leu
                100                 105                 110

His Gln Gln Leu Asn Asp Leu Lys Ala Cys Val Met Gln Glu Val Gly
            115                 120                 125

Val Gln Glu Pro Pro Leu Thr Gln Glu Asp Tyr Leu Leu Ala Val Arg
        130                 135                 140

Thr Tyr Phe His Arg Ile Thr Val Tyr Leu Arg Glu Lys Lys His Ser
145                 150                 155                 160

Pro Cys Ala Trp Glu Val Val Arg Ala Glu Val Trp Arg Ala Met Ser
                165                 170                 175

Ser Ser Ala Lys Leu Leu Ala Arg Leu Ser Glu Glu Lys Glu
                180                 185                 190
```

-continued

```
<210> SEQ ID NO 35
<211> LENGTH: 573
<212> TYPE: DNA
<213> ORGANISM: Mus musculus

<400> SEQUENCE: 35
atggctaggc tctgtgcttt cctgatgacc ctgctagtga tgagctactg gtcaacctgc        60
tctctaggat gtgacctgcc tcagactcat aacctcagga acaagagagc cttgaccctc       120
ctggtacaaa tgaggagact ctcccctctc tcctgcctga aggacagaaa ggactttaga       180
ttcccccagg agaaggtgga tgcccagcag atccagaatg ctcaagccat ccctgtccta       240
caagagctga cccagcaggt cctgaacatc ttcacatcaa aggactcatc tgctgcttgg       300
gatgcatccc tcctagactc attctgcaat gacctccatc agcagctcaa tgacctcaaa       360
gcctgtgtga tgcaggaggt gggggtgcag gaacctcccc tgacccagga agactacctg       420
ctggctgtga ggacatactt ccacaggatc actgtgtacc tgagagagaa gaaacacagc       480
ccctgtgcct gggaggtggt cagagcagaa gtctggagag ccatgtcttc ctcagccaag       540
ttgctggcaa gactgagtga ggagaaggag tga                                   573

<210> SEQ ID NO 36
<211> LENGTH: 269
<212> TYPE: PRT
<213> ORGANISM: Homo sapiens

<400> SEQUENCE: 36

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
        50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
        130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
                180                 185                 190

Lys Pro Thr Leu Gln Leu Glu Ser Val Asp Pro Lys Asn Tyr Pro Lys
            195                 200                 205

Lys Lys Met Glu Lys Arg Phe Val Phe Asn Lys Ile Glu Ile Asn Asn
        210                 215                 220

Lys Leu Glu Phe Glu Ser Ala Gln Phe Pro Asn Trp Tyr Ile Ser Thr
```

-continued

```
                225                     230                     235                     240

Ser Gln Ala Glu Asn Met Pro Val Phe Leu Gly Gly Thr Lys Gly Gly
                        245                     250                     255

Gln Asp Ile Thr Asp Phe Thr Met Gln Phe Val Ser Ser
                260                     265

<210> SEQ ID NO 37
<211> LENGTH: 810
<212> TYPE: DNA
<213> ORGANISM: Homo sapiens

<400> SEQUENCE: 37
atggcagaag tacctgagct cgccagtgaa atgatggctt attacagtgg caatgaggat      60
gacttgttct ttgaagctga tggccctaaa cagatgaagt gctccttcca ggacctggac     120
ctctgccctc tggatggcgg catccagcta cgaatctccg accaccacta cagcaagggc     180
ttcaggcagg ccgcgtcagt tgttgtggcc atggacaagc tgaggaagat gctggttccc     240
tgcccacaga ccttccagga gaatgacctg agcaccttct ttcccttcat ctttgaagaa     300
gaacctatct tcttcgacac atgggataac gaggcttatg tgcacgatgc acctgtacga     360
tcactgaact gcacgctccg ggactcacag caaaaaagct tggtgatgtc tggtccatat     420
gaactgaaag ctctccacct ccagggacag gatatggagc aacaagtggt gttctccatg     480
tcctttgtac aaggagaaga aagtaatgac aaaatacctg tggccttggg cctcaaggaa     540
aagaatctgt acctgtcctg cgtgttgaaa gatgataagc ccactctaca gctggagagt     600
gtagatccca aaattaccc aaagaagaag atggaaaagc gatttgtctt caacaagata     660
gaaatcaata acaagctgga atttgagtct gcccagttcc ccaactggta catcagcacc     720
tctcaagcag aaaacatgcc cgtcttcctg ggagggacca aaggcggcca ggatataact     780
gacttcacca tgcaatttgt gtcttcctaa                                       810

<210> SEQ ID NO 38
<211> LENGTH: 269
<212> TYPE: PRT
<213> ORGANISM: Mus musculus

<400> SEQUENCE: 38

Met Ala Thr Val Pro Glu Leu Asn Cys Glu Met Pro Pro Phe Asp Ser
1               5                   10                  15

Asp Glu Asn Asp Leu Phe Phe Glu Val Asp Gly Pro Gln Lys Met Lys
                20                  25                  30

Gly Cys Phe Gln Thr Phe Asp Leu Gly Cys Pro Asp Glu Ser Ile Gln
            35                  40                  45

Leu Gln Ile Ser Gln Gln His Ile Asn Lys Ser Phe Arg Gln Ala Val
        50                  55                  60

Ser Leu Ile Val Ala Val Glu Lys Leu Trp Gln Leu Pro Val Ser Phe
65                  70                  75                  80

Pro Trp Thr Phe Gln Asp Glu Asp Met Ser Thr Phe Phe Ser Phe Ile
                85                  90                  95

Phe Glu Glu Glu Pro Ile Leu Cys Asp Ser Trp Asp Asp Asp Asn
                100                 105                 110

Leu Leu Val Cys Asp Val Pro Ile Arg Gln Leu His Tyr Arg Leu Arg
        115                 120                 125

Asp Glu Gln Gln Lys Ser Leu Val Leu Ser Asp Pro Tyr Glu Leu Lys
        130                 135                 140
```

-continued

```
Ala Leu His Leu Asn Gly Gln Asn Ile Asn Gln Gln Val Ile Phe Ser
145                 150                 155                 160

Met Ser Phe Val Gln Gly Glu Pro Ser Asn Asp Lys Ile Pro Val Ala
                165                 170                 175

Leu Gly Leu Lys Gly Lys Asn Leu Tyr Leu Ser Cys Val Met Lys Asp
                180                 185                 190

Gly Thr Pro Thr Leu Gln Leu Glu Ser Val Asp Pro Lys Gln Tyr Pro
            195                 200                 205

Lys Lys Lys Met Glu Lys Arg Phe Val Phe Asn Lys Ile Glu Val Lys
        210                 215                 220

Ser Lys Val Glu Phe Glu Ser Ala Glu Phe Pro Asn Trp Tyr Ile Ser
225                 230                 235                 240

Thr Ser Gln Ala Glu His Lys Pro Val Phe Leu Gly Asn Asn Ser Gly
                245                 250                 255

Gln Asp Ile Ile Asp Phe Thr Met Glu Ser Val Ser Ser
                260                 265
```

```
<210> SEQ ID NO 39
<211> LENGTH: 810
<212> TYPE: DNA
<213> ORGANISM: Mus musculus

<400> SEQUENCE: 39
atggcaactg ttcctgaact caactgtgaa atgccacctt ttgacagtga tgagaatgac    60
ctgttctttg aagttgacgg accccaaaag atgaagggct gcttccaaac ctttgacctg   120
ggctgtcctg atgagagcat ccagcttcaa atctcgcagc agcacatcaa caagagcttc   180
aggcaggcag tatcactcat tgtggctgtg agaagctgt ggcagctacc tgtgtctttc   240
ccgtggacct tccaggatga ggacatgagc accttctttt ccttcatctt tgaagaagag   300
cccatcctct gtgactcatg ggatgatgat gataacctgc tggtgtgtga cgttcccatt   360
agacaactgc actacaggct ccgagatgaa caacaaaaaa gcctcgtgct gtcggaccca   420
tatgagctga agctctcca cctcaatgga cagaatatca accaacaagt gatattctcc   480
atgagctttg tacaaggaga accaagcaac gacaaaatac ctgtggcctt gggcctcaaa   540
ggaaagaatc tatacctgtc ctgtgtaatg aaagacggca cacccaccct gcagctggag   600
agtgtggatc ccaagcaata cccaaagaag aagatggaaa aacggtttgt cttcaacaag   660
atagaagtca gagcaaagt ggagtttgag tctgcagagt ccccaactg gtacatcagc   720 acctcacaag cagagcacaa gcctgtcttc ctgggaaaca acagtggtca ggacataatt   780
gacttcacca tggaatccgt gtcttcctaa                                     810
```

```
<210> SEQ ID NO 40
<211> LENGTH: 146
<212> TYPE: PRT
<213> ORGANISM: Homo sapiens

<400> SEQUENCE: 40

Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
                20                  25                  30

Ser Pro Gly Pro Val Pro Pro Ser Thr Ala Leu Arg Glu Leu Ile Glu
            35                  40                  45

Glu Leu Val Asn Ile Thr Gln Asn Gln Lys Ala Pro Leu Cys Asn Gly
        50                  55                  60
```

```
Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala Gln Phe
            115                 120                 125

Val Lys Asp Leu Leu Leu His Leu Lys Lys Leu Phe Arg Glu Gly Arg
    130                 135                 140

Phe Asn
145

<210> SEQ ID NO 41
<211> LENGTH: 441
<212> TYPE: DNA
<213> ORGANISM: Homo sapiens

<400> SEQUENCE: 41
atgcatccgc tcctcaatcc tctcctgttg gcactgggcc tcatggcgct tttgttgacc      60
acggtcattg ctctcacttg ccttggcggc tttgcctccc caggccctgt gcctccctct     120
acagccctca gggagctcat tgaggagctg gtcaacatca cccagaacca gaaggctccg     180
ctctgcaatg gcagcatggt atggagcatc aacctgacag ctggcatgta ctgtgcagcc     240
ctggaatccc tgatcaacgt gtcaggctgc agtgccatcg agaagaccca gaggatgctg     300
agcggattct gcccgcacaa ggtctcagct gggcagtttt ccagcttgca tgtccgagac     360
accaaaatcg aggtggccca gtttgtaaag gacctgctct acatttaaa gaaactttt      420 cgcgagggac ggttcaactg a                                             441

<210> SEQ ID NO 42
<211> LENGTH: 131
<212> TYPE: PRT
<213> ORGANISM: Mus musculus

<400> SEQUENCE: 42

Met Ala Leu Trp Val Thr Ala Val Leu Ala Leu Ala Cys Leu Gly Gly
1               5                   10                  15

Leu Ala Ala Pro Gly Pro Val Pro Arg Ser Val Ser Leu Pro Leu Thr
            20                  25                  30

Leu Lys Glu Leu Ile Glu Glu Leu Ser Asn Ile Thr Gln Asp Gln Thr
            35                  40                  45

Pro Leu Cys Asn Gly Ser Met Val Trp Ser Val Asp Leu Ala Ala Gly
    50                  55                  60

Gly Phe Cys Val Ala Leu Asp Ser Leu Thr Asn Ile Ser Asn Cys Asn
65                  70                  75                  80

Ala Ile Tyr Arg Thr Gln Arg Ile Leu His Gly Leu Cys Asn Arg Lys
                85                  90                  95

Ala Pro Thr Thr Val Ser Ser Leu Pro Asp Thr Lys Ile Glu Val Ala
            100                 105                 110

His Phe Ile Thr Lys Leu Leu Ser Tyr Thr Lys Gln Leu Phe Arg His
            115                 120                 125

Gly Pro Phe
    130
```

-continued

<210> SEQ ID NO 43
<211> LENGTH: 396
<212> TYPE: DNA
<213> ORGANISM: Mus musculus

<400> SEQUENCE: 43
atggcgctct gggtgactgc agtcctggct cttgcttgcc ttggtggtct cgccgcccca        60
gggccggtgc caagatctgt gtctctccct ctgacccctta aggagcttat tgaggagctg       120
agcaacatca cacaagacca gactcccctg tgcaacggca gcatggtatg gagtgtggac       180
ctggccgctg gcgggttctg tgtagccctg gattccctga ccaacatctc caattgcaat       240
gccatctaca ggacccagag gatattgcat ggcctctgta accgcaaggc ccccactacg       300
gtctccagcc tccccgatac caaaatcgaa gtagcccact ttataacaaa actgctcagc       360
tacacaaagc aactgtttcg ccacggcccc ttctaa                                  396

<210> SEQ ID NO 44
<211> LENGTH: 233
<212> TYPE: PRT
<213> ORGANISM: Homo sapiens

<400> SEQUENCE: 44

Met Ser Thr Glu Ser Met Ile Arg Asp Val Glu Leu Ala Glu Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 45
<211> LENGTH: 702
<212> TYPE: DNA
<213> ORGANISM: Homo sapiens

<400> SEQUENCE: 45
atgagcactg aaagcatgat ccgggacgtg gagctggccg aggaggcgct ccccaagaag        60 acagggggc cccagggctc caggcggtgc ttgttcctca gcctcttctc cttcctgatc        120
gtggcaggcg ccaccacgct cttctgcctg ctgcactttg gagtgatcgg cccccagagg        180
gaagagttcc ccagggacct ctctctaatc agccctctgg cccaggcagt cagatcatct        240
tctcgaaccc cgagtgacaa gcctgtagcc atgttgtag caaaccctca agctgagggg        300
cagctccagt ggctgaaccg ccgggccaat gccctcctgg ccaatggcgt ggagctgaga        360
gataaccagc tggtggtgcc atcagagggc ctgtacctca tctactccca ggtcctcttc        420
aagggccaag gctgcccctc acccatgtg ctcctcaccc acaccatcag ccgcatcgcc        480
gtctcctacc agaccaaggt caacctcctc tctgccatca gagcccctg ccagagggag        540 accccagagg gggctgaggc caagccctgg tatgagccca tctatctggg aggggtcttc        600
cagctggaga aggtgaccg actcagcgct gagatcaatc ggcccgacta tctcgacttt        660
gccgagtctg ggcaggtcta ctttgggatc attgccctgt ga                          702

<210> SEQ ID NO 46
<211> LENGTH: 235
<212> TYPE: PRT
<213> ORGANISM: Mus musculus

<400> SEQUENCE: 46

Met Ser Thr Glu Ser Met Ile Arg Asp Val Glu Leu Ala Glu Glu Ala
1               5                   10                  15

Leu Pro Gln Lys Met Gly Gly Phe Gln Asn Ser Arg Arg Cys Leu Cys
                20                  25                  30

Leu Ser Leu Phe Ser Phe Leu Leu Val Ala Gly Ala Thr Thr Leu Phe
            35                  40                  45

Cys Leu Leu Asn Phe Gly Val Ile Gly Pro Gln Arg Asp Glu Lys Phe
        50                  55                  60

Pro Asn Gly Leu Pro Leu Ile Ser Ser Met Ala Gln Thr Leu Thr Leu
65                  70                  75                  80

Arg Ser Ser Ser Gln Asn Ser Ser Asp Lys Pro Val Ala His Val Val
                85                  90                  95

Ala Asn His Gln Val Glu Glu Gln Leu Glu Trp Leu Ser Gln Arg Ala
            100                 105                 110

Asn Ala Leu Leu Ala Asn Gly Met Asp Leu Lys Asp Asn Gln Leu Val
        115                 120                 125

Val Pro Ala Asp Gly Leu Tyr Leu Val Tyr Ser Gln Val Leu Phe Lys
    130                 135                 140

Gly Gln Gly Cys Pro Asp Tyr Val Leu Leu Thr His Thr Val Ser Arg
145                 150                 155                 160

Phe Ala Ile Ser Tyr Gln Glu Lys Val Asn Leu Leu Ser Ala Val Lys
                165                 170                 175

Ser Pro Cys Pro Lys Asp Thr Pro Glu Gly Ala Glu Leu Lys Pro Trp
            180                 185                 190

Tyr Glu Pro Ile Tyr Leu Gly Gly Val Phe Gln Leu Glu Lys Gly Asp
        195                 200                 205

Gln Leu Ser Ala Glu Val Asn Leu Pro Lys Tyr Leu Asp Phe Ala Glu
    210                 215                 220

Ser Gly Gln Val Tyr Phe Gly Val Ile Ala Leu
225                 230                 235

-continued

```
<210> SEQ ID NO 47
<211> LENGTH: 708
<212> TYPE: DNA
<213> ORGANISM: Mus musculus

<400> SEQUENCE: 47
atgagcacag aaagcatgat ccgcgacgtg gaactggcag aagaggcact cccccaaaag        60
atggggggct tccagaactc caggcggtgc ctatgtctca gcctcttctc attcctgctt       120
gtggcagggg ccaccacgct cttctgtcta ctgaacttcg gggtgatcgg tccccaaagg       180
gatgagaagt tcccaaatgg cctccctctc atcagttcta tggcccagac cctcacactc       240
agatcatctt ctcaaaattc gagtgacaag cctgtagccc acgtcgtagc aaaccaccaa       300
gtggaggagc agctggagtg gctgagccag cgcgccaacg ccctcctggc caacggcatg       360
gatctcaaag acaaccaact agtggtgcca gccgatgggt tgtaccttgt ctactcccag       420
gttctcttca agggacaagg ctgccccgac tacgtgctcc tcacccacac cgtcagccga       480
tttgctatct cataccagga gaaagtcaac ctcctctctg ccgtcaagag cccctgcccc       540
aaggacaccc ctgaggggggc tgagctcaaa ccctggtatg agcccatata cctgggagga       600
gtcttccagc tggagaaggg ggaccaactc agcgctgagg tcaatctgcc caagtactta       660
gactttgcgg agtccgggca ggtctacttt ggagtcattg ctctgtga                    708

<210> SEQ ID NO 48
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Asp Tyr Lys Asp Asp Asp Asp Lys Gly
1               5

<210> SEQ ID NO 49
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Gly Lys Pro Ile Pro Asn Pro Leu Leu Gly Leu Asp Ser Thr
1               5                   10

<210> SEQ ID NO 50
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Glu Gln Lys Leu Ile Ser Glu Glu Asp Leu
1               5                   10
```

```
<210> SEQ ID NO 51
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

Gln Pro Glu Leu Ala Pro Glu Asp Pro Glu Asp
1               5               10

<210> SEQ ID NO 52
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Tyr Pro Tyr Asp Val Pro Asp Tyr Ala
1               5

<210> SEQ ID NO 53
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Tyr Thr Asp Ile Glu Met Asn Arg Leu Gly Lys
1               5               10

<210> SEQ ID NO 54
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 54

His His His His His His
1               5

<210> SEQ ID NO 55
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(5)
<223> OTHER INFORMATION: Any amino acid
<220> FEATURE:
<221> NAME/KEY: SITE
<222> LOCATION: (3)..(5)
<223> OTHER INFORMATION: /note="This region may encompass 1-3 residues"

<400> SEQUENCE: 55
```

-continued

```
Cys Cys Xaa Xaa Xaa Cys Cys
1               5

<210> SEQ ID NO 56
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Cys Cys Pro Gly Cys Cys
1               5
```